(12) United States Patent
Chou et al.

(10) Patent No.: US 11,719,618 B2
(45) Date of Patent: Aug. 8, 2023

(54) ASSAY ACCURACY IMPROVEMENT

(71) Applicant: Essenlix Corporation, Monmouth Junction, NJ (US)

(72) Inventors: Stephen Y. Chou, Princeton, NJ (US); Wei Ding, Princeton, NJ (US); Wu Chou, Basking Ridge, NJ (US); Jun Tian, Belle Mead, NJ (US); Yuecheng Zhang, Yardley, PA (US); Mingquan Wu, Princeton Junction, NJ (US); Xing Li, Metuchen, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/268,847

(22) PCT Filed: Aug. 28, 2019

(86) PCT No.: PCT/US2019/048678
§ 371 (c)(1),
(2) Date: Feb. 16, 2021

(87) PCT Pub. No.: WO2020/047177
PCT Pub. Date: Mar. 5, 2020

(65) Prior Publication Data
US 2021/0270722 A1 Sep. 2, 2021

Related U.S. Application Data

(60) Provisional application No. 62/742,247, filed on Oct. 5, 2018, provisional application No. 62/724,025, filed on Aug. 28, 2018.

(51) Int. Cl.
*G01N 15/14* (2006.01)
*G02B 21/34* (2006.01)
(Continued)

(52) U.S. Cl.
CPC ......... *G01N 15/1475* (2013.01); *G02B 21/34* (2013.01); *G06F 18/24143* (2023.01);
(Continued)

(58) Field of Classification Search
CPC ....... G01N 15/1475; G01N 2015/1006; G02B 21/34; G06K 9/6274; G06T 7/0012;
(Continued)

(56) References Cited

U.S. PATENT DOCUMENTS

2006/0171572 A1 8/2006 Breeuwer et al.
2011/0206251 A1 8/2011 Ramsay et al.
(Continued)

FOREIGN PATENT DOCUMENTS

CN 102567744 A 7/2012

OTHER PUBLICATIONS

Written Opinion of the International Searching Authority for PCT/US2019/048678 established by the ISA/US and dated Dec. 30, 2019.

*Primary Examiner* — Nay A Maung
*Assistant Examiner* — Jose M Torres

(57) ABSTRACT

One aspect of the present invention is to provide systems and methods that improve the accuracy of an assay that comprise at least one or more parameters each having a random error.

46 Claims, 16 Drawing Sheets

(51) Int. Cl.
*G06T 7/00* (2017.01)
*G06V 10/34* (2022.01)
*G06V 10/44* (2022.01)
*G06V 20/69* (2022.01)
*G06F 18/2413* (2023.01)
*G06V 10/764* (2022.01)
*G06V 10/82* (2022.01)
*G01N 15/10* (2006.01)

(52) U.S. Cl.
CPC ............ *G06T 7/0012* (2013.01); *G06V 10/34* (2022.01); *G06V 10/44* (2022.01); *G06V 10/454* (2022.01); *G06V 10/764* (2022.01); *G06V 10/82* (2022.01); *G06V 20/69* (2022.01); *G01N 2015/1006* (2013.01); *G06T 2207/30004* (2013.01)

(58) Field of Classification Search
CPC .......... G06T 2207/30004; G06V 10/34; G06V 10/44; G06V 10/454; G06V 10/764; G06V 10/82; G06V 20/69; G16H 30/40; G16H 40/60; B01L 2200/143; B01L 2200/148; B01L 2300/0822; B01L 2300/0893
See application file for complete search history.

(56) References Cited

U.S. PATENT DOCUMENTS

| | | |
|---|---|---|
| 2013/0282609 A1 | 10/2013 | Au et al. |
| 2016/0282279 A1 | 9/2016 | Ribnick et al. |
| 2017/0323435 A1 | 11/2017 | Minekawa et al. |
| 2018/0156775 A1 | 6/2018 | Chou et al. |
| 2018/0322327 A1* | 11/2018 | Smith .................. G06V 10/764 |
| 2018/0322941 A1* | 11/2018 | Krishnan ............... G16H 40/63 |
| 2021/0210205 A1* | 7/2021 | Drake .................... G06N 20/20 |

* cited by examiner

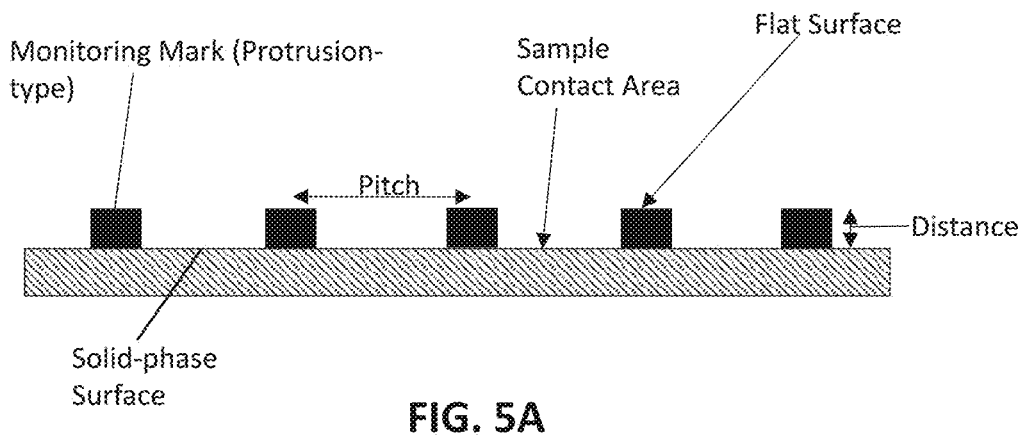

FIG. 5A

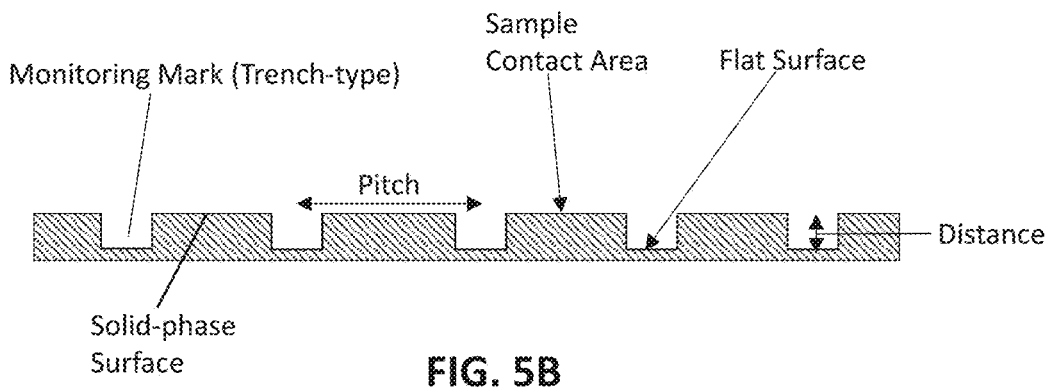

FIG. 5B

FIGs. 5A and 5B show cross-sectional views of the device for use in an imaging-based assay. FIG. 5A illustrates a solid-phase surface with protrusion-type monitoring marks. FIG. 5B illustrates a solid-phase surface with trench-type monitoring marks. Characteristics corresponding to the monitoring marks, e.g., pitch and distance, can be used, in an algorithm, to determine a property of an analyte in a sample.

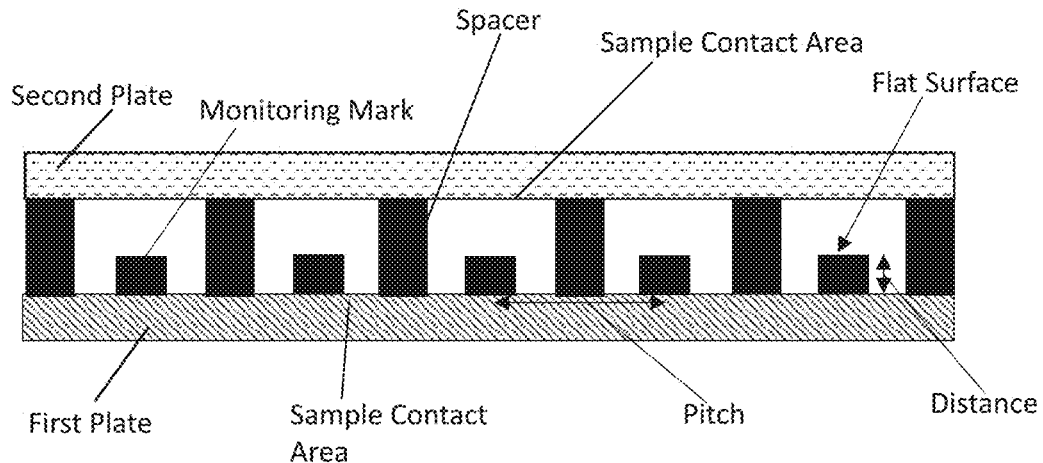

FIG. 6A

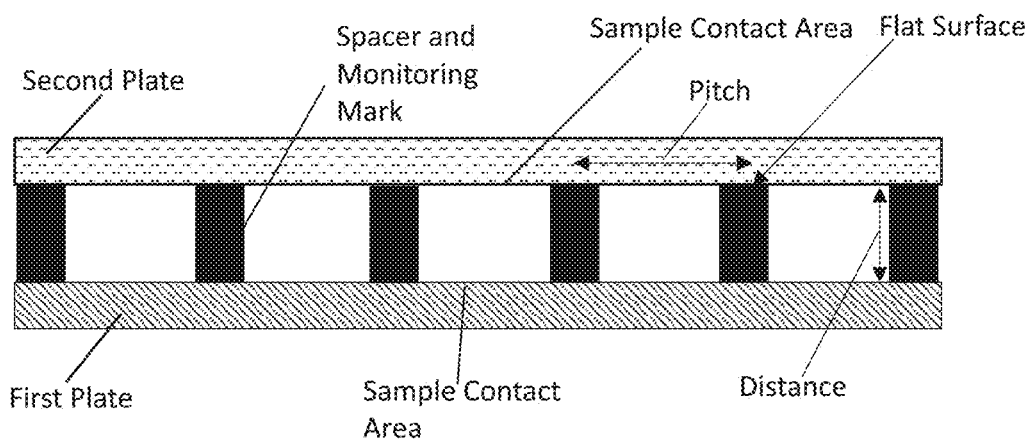

FIG. 6B

FIGs. 6A and 6B show cross-sectional views of the device for use in an imaging-based assay. FIGs. 6A illustrates how the monitoring marks (e.g., protrusion-type) can be separate structures from the spacers. FIG. 6B illustrates how the monitoring marks can be the same structures as the spacers. Characteristics corresponding to the monitoring marks can be used, in an algorithm, to determine a property of an analyte in a sample.

FIG. 6C shows a cross-sectional view of the device for use in an imaging-based assay. FIGs. 6C illustrates how the monitoring marks (e.g., trench-type) can be separate structures from the spacers. Characteristics corresponding to the monitoring marks can be used, in an algorithm, to determine a property of an analyte in a sample.

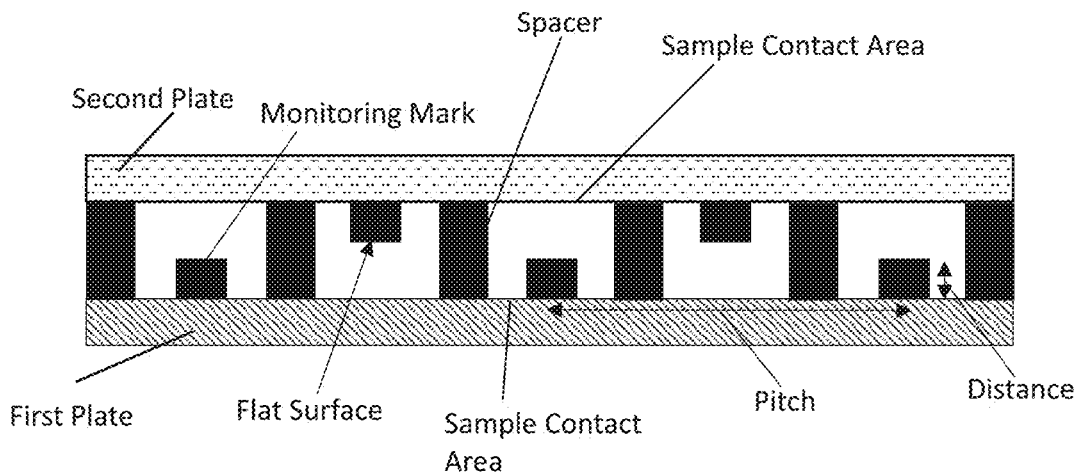

FIG. 6D

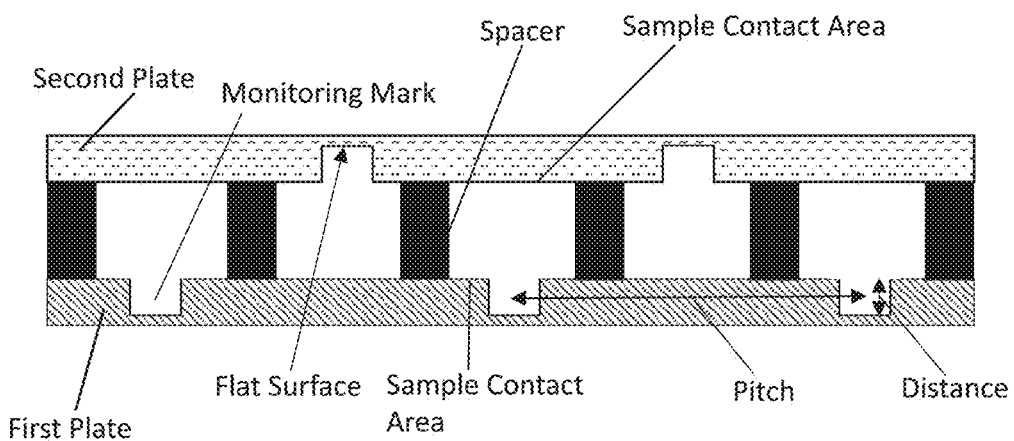

FIG. 6E

FIGs. 6D and 6E show cross-sectional views of the device for use in an imaging-based assay. FIGs. 6D and 6E illustrate how the monitoring marks can be separate structures from the spacers and disposed on both sample contact areas of the device. Characteristics corresponding to the monitoring marks can be used, in an algorithm, to determine a property of an analyte in a sample.

ASSAY ACCURACY IMPROVEMENT

CROSS-REFERENCE TO RELATED APPLICATIONS

This application is a National Stage entry (§ 371) application of International Application No. PCT/US2019/048678, filed on Aug. 28, 2019, which claims the benefit of priority of U.S. Provisional Patent Application No. 62/724,025, filed on Aug. 28, 2018, and U.S. Provisional Patent Application No. 62/742,247, filed on Oct. 5, 2018, the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays, particularly related to how to improve the accuracy and reliability of the assays when the assays are performed using simple devices and limited resource settings.

BACKGROUND

In assaying a biomarker in a sample from a subject (e.g. human) for diagnostic a disorder or diseases, the accuracy of the assay is essential. A wrong result can be harmful to the subject. Traditionally, an accuracy of an assay is achieved by a "perfect protocol paradigm"—namely, performing everything, including a sample handling, precisely. Such approach needs a complex machines, professional operation, ideal environments, etc. to ensure a "perfect" assay device and "perfect" assay performance and operation. However, there are a great need to develop systems and methods that improve the accuracy of an assay that comprising at least one parameters each having a random error.

SUMMARY

The following brief summary is not intended to include all features and aspects of the present invention.

One aspect of the present invention is to provide systems and methods that improve the accuracy of an assay that comprising at least one parameters each having a random error. The accuracy improvement is made by checking the trustworthy of the assay in addition to the assay biochemistry measurement of an analyte in a sample.

Another aspect of the present invention is to provide systems and methods that improve the accuracy of an assay that comprising at least one parameters each having a random error, by using monitoring structures that are distributed inside of the sample.

Another aspect of the present invention is to provide systems and methods that improve the accuracy of an assay that comprising at least one parameters each having a random error, by using monitoring the trustworthy of a sample used in the assay.

In some embodiments, as illustrated in FIG. 1, the present invention provides a method for improving accuracy of an assay in detecting an analyte in or suspected of being in a sample, wherein a device or an operation of the assay has one or more parameters each having a random variation, the method comprising: (a) detecting, using the assay, the analyte in the sample that contains or is suspected of containing the analyte, wherein the detecting comprises: (i) placing the sample into the assay device; and (ii) using the assay device to detect the analyte, generating a detection result; and (b) determining trustworthiness of the detection result in step (a), comprising: (i) taking, using an imager, one or more images of at least a part of the sample and/or at least part of the assay device, wherein the images substantially represent the conditions under which the at least a part of the sample is measured in generating the detection result in step (a); and (ii) determining a trustworthiness of the detection result in step (a) by using an algorithm to analyze the images and generating a trustworthy score, wherein the algorithm comprises a comparison of the one or more images with training data, and wherein the training data comprises a random variation of one of the one or more parameters and/or a statistical response of the accuracy of the assay to a random variation of the one or more parameters; and (c) reporting the detection result and the trustworthy score.

In some embodiments, the present invention provides a method for improving accuracy of an assay in detecting an analyte in or suspected of being in a sample, wherein a device or an operation of the assay has one or more parameters each having a random variation, the method comprising: (a) placing the sample into the assay device; (b) taking, using an imager, one or more images of at least a part of the sample and at least part of the assay device; (c) analyzing the one or more images to detect the analyte in the sample, and generating a detection result; and (d) determining trustworthiness of the detection result using an algorithm to analyze the one or more images and generating a trustworthy score, wherein the algorithm comprises a comparison of the one or more images with training data, and wherein the training data comprises a random variation of one of the one or more parameters and/or a statistical response of the accuracy of the assay to a random variation of the one or more parameters; and (e) reporting the detection result and the trustworthy score.

In some embodiments, as illustrated in FIG. 2, the present invention provides a method for improving accuracy of an assay in detecting an analyte in or suspected of being in a sample, wherein a device or an operation of the assay has one or more parameters each having a random variation, the method comprising: (a) placing the sample into the assay device, wherein the assay device has at least one sample contact area for contacting the sample and wherein the at least one sample contact area comprises one or more monitoring structures; (b) taking, using an imager, one or more images of at least a part of the sample and at least a part of the monitoring structures; (c) analyzing the one or more images to detect the analyte in the sample, and generating a detection result; and (d) determining trustworthiness of the detection result using an algorithm to analyze the one or more images and generating a trustworthy score, wherein the algorithm comprises a comparison of the one or more images with training data, and wherein the training data comprises a random variation of one of the one or more parameters, a monitoring structure, and/or a statistical response of the accuracy of the assay to a random variation of the one or more parameters; and (e) reporting the detection result and the trustworthy score; wherein the monitoring structures comprises a structure of an optical property that is used to monitor the operation and/or assay device quality of the assay.

In some embodiments, the present invention provides a method for improving accuracy of an assay in detecting an analyte in or suspected of being in a sample, wherein a device or an operation of the assay has one or more parameters each having a random variation, the method comprising: (a) detecting, using the assay, the analyte in the sample that contains or is suspected of containing the analyte, wherein the detecting comprises: (i) placing the sample into the assay device; and (ii) using the assay device to detect the analyte, generating a detection result; and (b) determining trustworthiness of the detection result in step (a), comprising: (i) taking, using an imager, one or more images of at least a part of the sample and/or at least part of the assay device, wherein the images substantially represent the conditions under which the at least a part of the sample is measured in generating the detection result in step (a); and (ii) determining a trustworthiness of the detection result in step (a) by using a first algorithm to analyze the images and generating a trustworthy score, wherein the first algorithm comprises a comparison of the one or more images with training data, and wherein the training data comprises a random variation of one of the one or more parameters and/or a statistical response of the accuracy of the assay to a random variation of the one or more parameters; and (c) reporting the detection result if the trustworthy score passes a threshold, otherwise go to the step (d); (d) using a different assay device repeat steps (a), (b), and (c) if the trustworthy score passes the threshold and report the detection result; otherwise go to the step (e); (e) determining an average detection result and an average trustworthy score by using a second algorithm to analyze all the detection results and all the images generated before step (e) to generate an average detection result and an average trustworthy score, wherein the second algorithm comprises a comparison of the one or more images with training data, and wherein the training data comprises a random variation of one of the one or more parameters and/or a statistical response of the accuracy of the assay to a random variation of the one or more parameters; and (f) reporting the detection result if the average trustworthy score passes the threshold, otherwise go to the step (d).

In some embodiments, the algorithm is machine learning. as illustrated in FIG. 3, In some embodiments, the assay device has at least one sample contact area for contacting the sample and wherein the at least one sample contact area comprises one or more monitoring structures; wherein the monitoring structures comprises a structure of an optical property that is used to monitor the operation and/or assay device quality of the assay, and wherein the training data comprising the monitoring structure.

In some embodiments, the sample comprises at least one of parameters that has a random variation.

In some embodiments, the sample comprises at least one of parameters that has a random variation, wherein the parameter comprises having dusts, air bubble, non-sample materials, or any combination of thereof.

In some embodiments, the sample comprises at least one of parameters that has a random variation, wherein the parameter comprises having dusts, air bubble, non-sample materials, or any combination of thereof.

In some embodiments, the method further comprises a step of keep or reject the detection result using the trustworthy score.

In some embodiments, the assay is a device that uses a chemical reaction to detect the analyte.

In some embodiments, the assay is an immunoassay, nucleic acid assay, colorimetric assay, luminescence assay, or any combination of thereof.

In some embodiments, the assay device comprises two plates facing each other with a gap, wherein at least a part of the sample is inside of the gap.

In some embodiments, the assay device comprises a QMAX, comprising two plates movable to each other and spacers that regulate the spacing between the plates.

In some embodiments, some of the monitoring structures are periodically arranged.

In some embodiments, the sample is selected from cells, tissues, bodily fluids, and stool.

In some embodiments, the sample is amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine, or exhaled breath condensate.

In some embodiments, the analyte comprising a molecule (e.g., a protein, peptides, DNA, RNA, nucleic acid, or other molecule), a cell, a tissues, a virus, and a nanoparticle.

In some embodiments, the samples are the samples that are non-flowable but deformable.

In some embodiments, the method further comprises a step of discarding the detection result generated in step (a), if the worthiness determined in the step (b) is below a threshold. In some embodiments, the method further comprises a step of revising the detection result generated in step (a), if the worthiness determined in the step (b) is below a threshold.

In some embodiments, the present invention provides an apparatus for improving accuracy of an assay that has one or more operation conditions unpredictable and random, comprising: (1) a detection device that detects an analyte in a sample to generate a detection result, wherein the sample contains or is suspected of containing the analyte; (2) a checking device that checks trustworthiness of a particular detection result generated by the detection device, comprising: (i) an imager that is capable of taking one or more images of (1) a portion of the sample and/or (2) a portion of the detection instrument that is surrounded the portion of the sample, wherein the images substantially represent the conditions that the portion of the sample is measured in generating detection result in step (a); and (ii) a computing unit with an algorithm that is capable of analyzing the features in the images taken in step (b)(i) to determine a trustworthiness of the detection result; (c) discarding the detection result generated in step (a), if the step (b) determines the detection result is untrustworthy; wherein the step (a) has one or more operation conditions that is unpredictable and random.

In some embodiments, the algorithm is machine learning, artificial intelligence, statistical methods, or a combination of thereof.

In some embodiments, the present invention provides a method for assaying a sample with one or more operation conditions \having a random variation, comprising: (a) providing a sample that contains or is suspected of containing an analyte; (b) depositing the sample onto a solid surface; (c) measuring, after step (b), the sample to detect the analyte and generate a result of the detection, wherein the result can be effected by one more operation conditions in performing the assaying, and wherein the operation conditions are random and unpredictable; (d) imaging a portion of the sample area/volume where the analyte in the sample is measured in step (c); and (e) determining the error-risk-probability of the result measured in step (c) by analyzing the one or more operation conditions shown in one or more images generated in step (d).

In some embodiments, if step (e) determines that the result measured in step (c) has a high error risk probability, the result will be discarded.

In some embodiments, the present invention provides a device for assaying an analyte present in a sample under one or more operational variables, comprising: (a) a solid surface having a sample contact area for receiving a thin layer of a sample, the sample containing an analyte to be measured; (b) an imager configured to image a portion of the sample contact area where the analyte is measured; and (c) a non-transitory computer readable medium having an instruction that, when executed, it performs the determination of trustworthy of the assay result by analyzing the operational variables displayed in the image of the portion of the sample.

In some embodiments, the present invention provides a method for assaying a sample with one or more operational variables, comprising: (a) depositing a sample containing an analyte between a first plate and a second plate; wherein the sample is sandwiched between the first plate and the second plate which are substantially in parallel; (b) measuring the analyte contained in the sample to generate a result, wherein the measuring involving one more operational variables that are random and unpredictable; (c) imaging an area portion of the first plate and the second plate to generate an image, where the area portion contains the sample and the analyte contained in the sample is measured; and (d) determining if the result measured in step (b) is trustworthy by analyzing the operational variables shown in the image of the area portion containing the sample.

In some embodiments, if the analysis in step (d) determines that the result measured in step (b) is not trustworthy, the result is discarded.

In some embodiments, the present invention provides a method for assaying a sample with one or more operational variables, comprising: (a) depositing a sample that contains or suspected to contain an analyte between a first plate and a second plate, wherein the sample is sandwiched between the first plate and the second plate that are movable relative to each other into a first configuration or a second configuration; (b) measuring the analyte in the sample to generate a result, wherein the measuring involving one more operational variables that are random and unpredictable; and (c) imaging an area portion of the sample where the analyte is measured; and (d) determining if the result measured in step (b) is trustworthy by analyzing the operational variables shown in the image of the area portion, wherein the first configurations is an open configuration, in which the two plates are partially or completely separated apart, the spacing between the plates is not regulated by the spacers, and the sample is deposited on one or both of the plates, and wherein the second configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

In some embodiments, if step (d) determines that the result measured in step (b) is not trustworthy, the result is discarded.

In some embodiments, the present invention provides a method for assaying a sample with one or more operational variables, comprising: (a) depositing a sample that contains or is suspected to contain an analyte, wherein the sample is deposited in an area in the device of any embodiment described in the disclosure; (b) measuring the analyte in the sample, wherein the measuring involving one more operational variables that are random and unpredictable; and (c) imaging a portion of the sample area wherein the portion is where the analyte is measured; and (d) determining if the result measured in step (b) is trustworthy by analyzing the operational variables shown in the image of the portion of the sample.

In some embodiments, if the analysis in step (d) determines that the result measured in step (b) is not trustworthy, the result is discarded.

In some embodiments, the multiple assay devices are used to perform the assaying, wherein the assay has a step of using an image analysis to check if an assay result is trustworthy, and wherein if a first assay device is found to be not trustworthy, a second assay device is used, until the assay result is found to be trustworthy.

In some embodiments, the sample is a biological or chemical sample.

In some embodiments, in step (d), the analysis uses machine learning with a training set to determine if a result is trustworthy, wherein the training set uses an operational variable with an analyte in the sample.

In some embodiments, the in step (d), the analysis uses a lookup table to determine if a result is trustworthy, wherein the lookup table contains an operational variable with an analyte in the sample.

In some embodiments, the in step (d), the analysis uses a neural network to determine if a result trustworthy, wherein the neural network is trained using an operational variable with an analyte in the sample.

In some embodiments, the in step (d), the analysis uses a threshold for the operational variable to determine if a result is trustworthy.

In some embodiments, in step (d), the analysis uses machine learning, lookup table or neural work to determine if a result is trustworthy, wherein the operational variables include a condition of air bubble and/or dust in the image of the portion of the sample.

In some embodiments, in step (d), the analysis uses machine learning, that determines if a result is trustworthy, use machine learning, lookup table or neural network to determine the operational variables of air bubble and/or dust in the image of the portion of the sample.

In some embodiments, in step (b) of measuring the analyte, the measuring uses imaging.

In some embodiments, in step (b) of measuring the analyte, the measuring uses imaging, and the same image used for analyte measurement is used for the trustworthy determination in step (d).

In some embodiments, in step (b) of measuring the analyte, the measuring uses imaging, and the same imager used for analyte measurement is used for the trustworthy determination in step (d).

In some embodiments, the device used in any prior device claim further comprises a monitoring mark.

In some embodiments, the monitoring mark is used as a parameter together with an imaging processing method in an algorithm that (i) adjusting the imagine, (ii) processing an image of the sample, (iii) determining a property related to the micro-feature, or (iv) any combination of the above.

In some embodiments, the monitoring mark is used as a parameter together with step (b).

In some embodiments, the spacers are the monitoring mark, wherein the spacers have a substantially uniform height that is equal to or less than 200 microns, and a fixed inter-spacer-distance (ISD).

In some embodiments, the monitoring mark is used for estimating the TLD (true-lateral-dimension) and true volume estimation.

In some embodiments, step (b) further comprises an image segmentation for image-based assay.

In some embodiments, step (b) further comprises a focus checking in image-based assay.

In some embodiments, step (b) further comprises an Evenness of analyte distribution in the sample.

In some embodiments, step (b) further comprises an analyze and detection for aggregated analytes in the sample.

In some embodiments, step (b) further comprises an analyze for Dry-texture in the image of the sample in the sample.

In some embodiments, step (b) further comprises an analyze for Defects in the sample.

In some embodiments, step (b) further comprises a correction of camera parameters and conditions as distortion removal, temperature correction, brightness correction, contrast correction.

In some embodiments, step (b) further comprises methods and operations with Histogram-based operations, Mathematics-based operations, Convolution-based operations, Smoothing operations, Derivative-based operations, Morphology-based operations.

In some embodiments, the present invention provides a system for assaying a sample with one or more operation conditions un, comprising: (a) load the sample to a sample holding device, e.g. a QMAX device, whose gap is in proportion to the size of the analyte to be analyzed or the analytes form a mono-layer between the gap; (b) take an image of the sample in the sample holding device on the area-of-interest (AoI) for assaying with an imager; (c) segment the image of the sample taken by the said imager from (b) into equal-sized and non-overlapping sub-image patches (e.g, 8×8 equal-sized small image patches); (d) perform machine learning based inference with a trained machine learning model for analyte detection and segmentation on each image patch—to determine and not limited to the analyte count and concentration thereof; (e) sort the analyte concentration of the constructed sub-image patches in ascending order and determine the 25% quantile Q1 and 75% quantile Q3 thereof; (f) determine the uniformity of the analytes in the image of the sample with an inter-quantile-range based confidence measure: confidence-IQR=(Q3−Q1)/(Q3+Q1); and (g) if the confidence-IQR from (f) exceeds a certain threshold (e.g. 30%), raise the flag and the assay result is not trustworthy, wherein the said threshold is derived from the training/evaluation data or from the physical rules that govern the distribution of the analytes.

In some embodiments, the present invention provides a system for assaying a sample with one or more operation conditions un, comprising: (a) load the assay into a sample holding device, e.g. a QMAX device, whose gap is in proportion to the size of the analyte to be analyzed or the analytes form a mono-layer between the gap; (b) take an image of the sample in the sample holding device on the area-of-interest (AoI) for assaying with an imager; (c) perform machine learning based inference with a trained machine learning model for dry texture detection and segmentation—to detect the dry texture areas and determine the area-dry-texture-in-AoI associated with the segmentation contour masks that cover those areas of dry-texture in the AoI of the image of the sample; (d) determine the area ratio between the area-dry-texture-in-AoI and the area-of-the-AoI: ratio-dry-texture-area-in-AoI=area-dry-texture-in-AoI/area-of-AoI; and (e) if the ratio-dry-texture-area-in-AoI from (d) exceeds a certain threshold (e.g. 10%), raise the flag and the assay result is not trustworthy, wherein the said threshold is derived from the training/evaluation data or from the physical rules that govern the distribution of the analytes.

In some embodiments, the present invention provides a system for assaying a sample with one or more operation conditions un, comprising: (a) load the assay into a sample holding device, e.g. a QMAX device, whose gap is in proportion to the size of the analyte to be analyzed or the analytes form a mono-layer between the gap; (b) take an image of the sample in the sample holding device on the area-of-interest (AoI) for assaying with an imager; (c) perform machine learning based inference with a trained machine learning model for aggregated analytes detection and segmentation—to detect the clustered analytes and determine the area (area-aggregated-analytes-in-AoI) associated with the segmentation contour masks that cover them in the AoI thereof; (d) determine the area ratio between the area-aggregated-analytes-in-AoI and the area-of-AoI: ratio-aggregated-analytes-area-in-AoI=area-aggregated-analytes-in-AoI/area-of-AoI; and (e) if the ratio-aggregated-analytes-area-in-AoI from (d) exceeds a certain threshold (e.g. 40%), raise the flag and the assay result is not trustworthy, wherein the said threshold is derived from the training/evaluation data or from the physical rules that govern the distribution of the analytes.

In some embodiments, the present invention provides a system for assaying a sample with one or more operation conditions un, comprising: (a) load the assay into a sample holding device, e.g. a QMAX device, whose gap is in proportion to the size of the analyte to be analyzed or the analytes form a mono-layer between the gap: (b) take an image of the sample in the sample holding device on the area-of-interest (AoI) for assaying with an imager; (c) perform machine learning based inference with a trained machine learning model for detection and segmentation of the defects in the image of the sample, wherein the defects include and not limited to dusts, oil, etc.—to detect the defects and determine the area (area-defects-in-AoI) associated with the segmentation contour masks that cover them in the AoI thereof; (d) determine the ratio between the area-defects-in-AoI and the area-of-AoI: ratio-defects-area-in-AoI=area-defects-in-AoI/area-of-AoI; and e) if the ratio-defects-area-in-AoI from (d) exceeds a certain threshold (e.g. 15%), raise the flag and the assay result is not trustworthy, wherein the said threshold is derived from the training/evaluation data or from the physical rules that govern the distribution of the analytes.

In some embodiments, the present invention provides a system for assaying a sample with one or more operation conditions un, comprising: (a) load the assay into a sample holding device, e.g. a QMAX device, whose gap is in proportion to the size of the analyte to be analyzed or the analytes form a mono-layer between the gap; (b) take an image of the sample in the sample holding device on the area-of-interest (AoI) for assaying with an imager; (c) perform machine learning based inference with a trained machine learning model for air bubble and air gap detection and segmentation—to detect air bubbles and air gaps and determine area-airbubble-gap-in-AoI associated with the segmentation contour masks that cover them in the AoI thereof; (d) determine the area ratio between the areaairbubble-gap-in-AoI and the area-of-AoI: ratio-airbubble-gap-area-in-AoI=area-airbubble-gap-in-AoI/area-of-AoI; and (e) if the ratio-airbubble-gap-area-in_AoI from (d) exceeds a certain threshold (e.g. 10%), raise the flag and the assay result is not trustworthy, wherein the said threshold is derived from the training/evaluation data or from the physical rules that govern the distribution of the analytes.

In some embodiments, the present invention provides a system for assaying a sample with one or more operation conditions un, comprising: (a) load the assay into a sample holding device, e.g. a QMAX device, wherein the said sample holding device has a gap in proportion to the size of the analyte to be analyzed or the analytes form a mono-layer between the gap, and there are monitor marks (e.g. pillars)—residing in the device and not submerged, that can be imaged by an imager on the sample holding device with the sample; (b) take an image of the sample in the sample holding device on the area-of-interest (AoI) for assaying with an imager; (c) perform machine learning based inference with a trained machine learning model to detect and segment the monitor marks (pillars) with analytes on top—to determine the area (area-analytes-on-pillars-in-AoI) associated with the detected monitor marks (pillars) based on their segmentation contour masks in the AoI; (d) determine the area ratio between the area-analytes-on-pillars-in-AoI and the area-of-AoI: ratio-analytes-on-pillars-area-in-AoI=area-analytes-on-pillars-in-AoI/area-of-AoI; and (e) if the ratio-analytes-on-pillars-area-in-AoI from (d) exceeds a certain threshold (e.g. 10%) raise the flag and the assay result is not trustworthy, wherein the said threshold is derived from the training/evaluation data or from the physical rules that govern the distribution of the analytes.

In some embodiments, the present invention provides a system for assaying a sample with one or more operation conditions un, comprising: (a) load the assay into a sample holding device, e.g. a QMAX device; (b) take an image of the sample in the sample holding device on the area-of-interest (AoI) for assaying with an imager; (c) perform machine learning based focus check to detect if the image of the sample taken by the imager is in focus to the sample, wherein the machine learning model for detecting the focus of the said imager is built from the multiple images of the imager with in focus and off focus conditions; and (d) if the image of the sample taken by the said imager is detected off focus from (c), raise the flag and the image-based assay result is not trustworthy.

In some embodiments, the present invention provides a system for assaying a sample with one or more operation conditions un, comprising: (a) load the assay into a sample holding device, e.g. a QMAX device; (b) take an image of the sample in the sample holding device on the area-of-interest (AoI) for assaying with an imager; (c) perform machine learning based analyte detection; and (d) if the analyte count is extremely low beyond a preset acceptable range, raise the flag and the result is not trustworthy, wherein the acceptable range is specified based on physical or biological conditions of the assay.

In some embodiments, the present invention provides a system for assaying a sample with one or more operation conditions un, comprising: (a) load the assay into a sample holding device, e.g. a QMAX device; (b) take an image of the sample in the sample holding device on the area-of-interest (AoI) for assaying with an imager; (c) partition the image of the sample into non-overlapping, equal sized sub-image patches; (d) perform machine learning based analyte detection over each sub-image patch thereof; and (e) if for some sub-image patches, the count of the detected analytes is unrealistically low (e.g. in complete-blood-count, the number of red blood cell in the sample is below human acceptable range), raise the flag and the result is not trustworthy for having not enough samples or non-uniform distribution of the sample in the assay.

In some embodiments, the detection and segmentation of abnormalities from the image of the sample taken by the imager in the image-based assay are based on image processing, machine learning or a combination of image processing and machine learning.

In some embodiments, the estimation of the area covered by segmentation contour masks in the area-of-interest (AoI) of the image of the sample utilizes a per-image or per-sub-image patch based true-lateral-dimension (or Field-of-View (FoV)) estimation to compensate the distortions in microscopic imaging, including and not limited to spherical distortion from the lens, defects at microscopic level, misalignment in focusing, etc.

In some embodiments, the present invention further comprises monitoring marks (e.g. pillars) built in with the sample holding device, e.g. QMAX card; and the said monitor marks (e.g. pillars) are applied as detectable anchors to make the estimation of the true-lateral-dimension (or Field-of-View (FoV)) estimation accurate in face of the distortions in microscopic imaging.

In some embodiments, the monitor marks (e.g. pillars) of the sample holding device have some configurations with a prescribed periodic distribution in the sample holding device, e.g. QMAX card, to make detection and location of the monitor marks as anchors in true-lateral-dimension (TLD) (or Field-of-View (FoV)) estimation reliable and robust.

In some embodiments, the detection and characterization of the outliers in the image-based assay are based on the non-overlapping sub-image patches of the input image of the sample described herein, and the determination of the outliers can be based on non-parametric methods, parametric methods and a combination of both in the assaying process.

In some embodiments, the present invention provides a method, comprising: (a) detecting an analyte in a sample that comprises or is suspected of comprising the analyte, said detecting comprising: (i) depositing the sample into a detection instrument, and (ii) measuring the sample using the detection instrument to detect the analyte, thereby generating a detection result; (b) determining a reliability of the detection result, said determining comprising: (i) taking one or more images of a portion of the sample and/or a portion of the detection instrument adjacent the portion of the sample, wherein the one or more images reflect one or more operation conditions under which the detection result was generated; and (ii) using a computational device with an algorithm to analyze the one or more images to determine a reliability of the detection result in step (a); and (c) reporting the detection result and the reliability of the detection result; wherein the one or more operation conditions are unpredictable and/or random.

In some embodiments, when assaying a sample in a limited resource setting (LRS), a result from the assaying can be unreliable. However, traditionally, there is no checking on the reliability of a particular result during or after a particular testing for a given sample.

In some embodiments, in LRS assaying (or even in the lab testing environment), one or more unpredictable random operation conditions can occur and affect the assaying result. When that happens, it can be substantially different from one particular assaying to next assaying, even using the same sample. However, instead of taking the assaying result as it is, the reliability of a particular result in a particular testing for a given sample can be assessed by analyzing one or more factors that are related to the assay operation conditions in that particular assay.

In some embodiments, in LRS assaying that has one or more unpredictable random operation conditions, the overall accuracy of the assaying can be substantially improved by using an analysis on the reliability of each particular assaying and by rejecting the untrustworthy assay results.

In some embodiments, the assay is performed not only by measuring the analytes in a particular test, but also checking the trustworthy of the measuring result through an analysis of the operation conditions of that particular test.

In some embodiments, the checking of the trustworthy of the measuring result of the assay is modeled in a machine learning framework, and machine learning algorithms and models are devised and applied to handle unpredictable random operation conditions that occur and affect the assay result.

In some embodiments, the innovative use of machine learning has the advantage of automating the process of determining the trustworthy of the assay result in face of unpredictable random operation conditions in assaying—directly from the data without making explicit assumptions on the unpredictable conditions which can be complex, hard to predict, and error prone.

In some embodiments, the machine learning framework in the present invention involves a process that comprises: (a) gather training data of the task; (b) prepare the data with labeling; (c) select a machine learning model; (d) train the selected machine learning model with the training data; (e) tune the hyper-parameters and model structure with the training and evaluation data until the model reaches a satisfactory performance on the evaluation and test data; and (f) perform the inference on the test data using the trained machine learning model from (e).

BRIEF DESCRIPTION OF THE DRAWINGS

The skilled artisan will understand that the drawings, described below, are for illustration purposes only. The drawings are not intended to limit the scope of the present teachings in any way. The drawings are not entirely in scale. In the figures that present experimental data points, the lines that connect the data points are for guiding a viewing of the data only and have no other means.

FIGS. 5A and 5B show side views of the device for use in an imaging-based assay. FIG. 5A illustrates a solid-phase surface with protrusion-type monitoring marks. FIG. 5B illustrates a solid-phase surface with trench-type monitoring marks. Characteristics corresponding to the monitoring marks, e.g., pitch and distance, can be used, in an algorithm, to determine a property of an analyte in a sample.

FIGS. 6A and 6B show side views of the device for use in an imaging-based assay. FIG. 6A illustrates how the monitoring marks (e.g., protrusion-type) can be separate structures from the spacers. FIG. 6B illustrates how the monitoring marks can be the same structures as the spacers. Characteristics corresponding to the monitoring marks can be used, in an algorithm, to determine a property of an analyte in a sample.

FIG. 6C illustrates how the monitoring marks (e.g., trench-type) can be separate structures from the spacers. Characteristics corresponding to the monitoring marks can be used, in an algorithm, to determine a property of an analyte in a sample.

FIGS. 6D and 6E show side views of the device for use in an imaging-based assay. FIGS. 6D and 6E illustrate how the monitoring marks can be separate structures from the spacers and disposed on both sample contact areas of the device. Characteristics corresponding to the monitoring marks can be used, in an algorithm, to determine a property of an analyte in a sample.

DETAILED DESCRIPTION OF EXEMPLARY EMBODIMENTS

Figure 1:
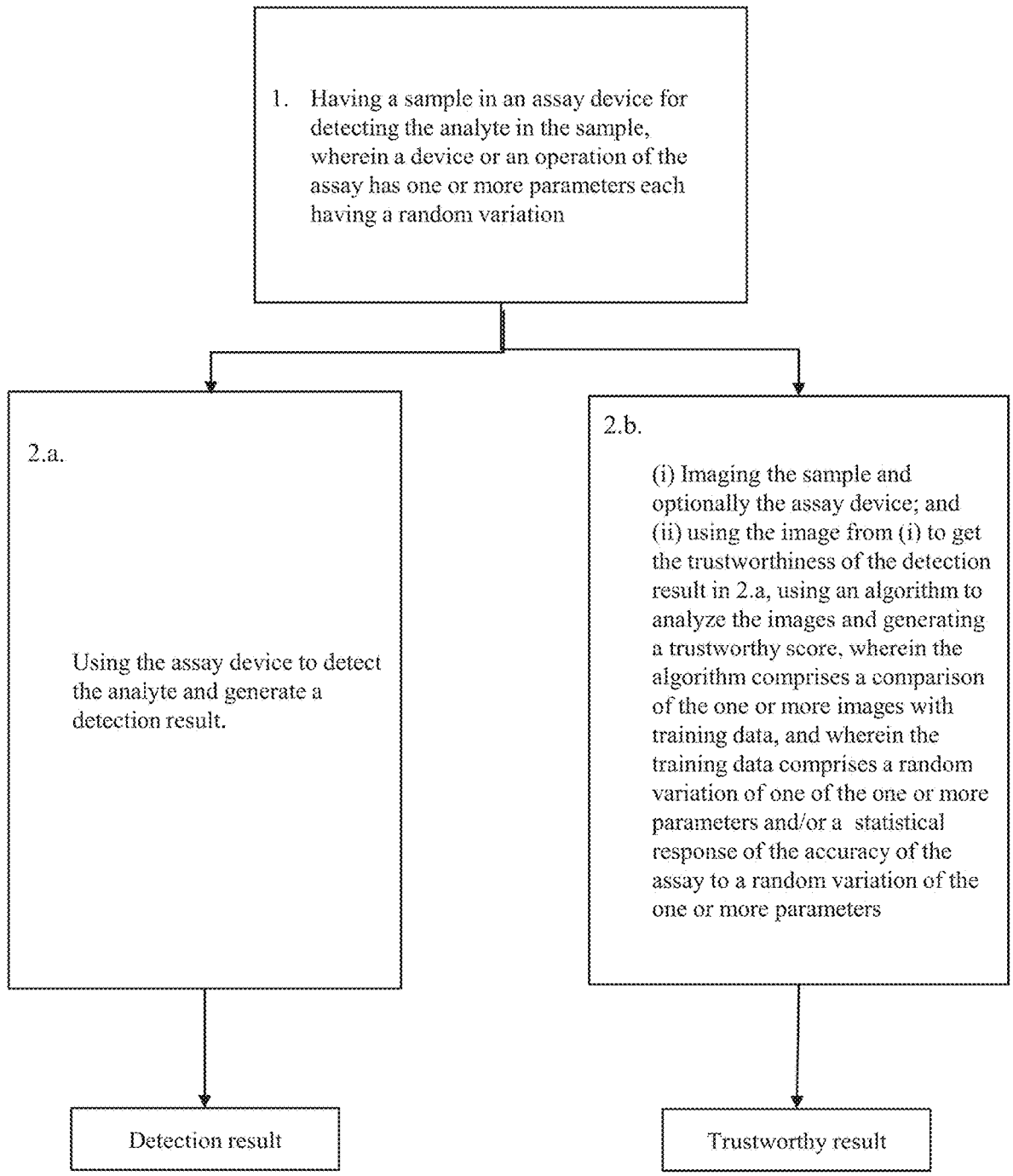
FIG. 1 illustrates a block diagram of embodiment of improving assay accuracy by measuring the trustworthy of the assay device and/or assay operation. In some embodiments, it check the trustworthy of the sample.
Figure 2:
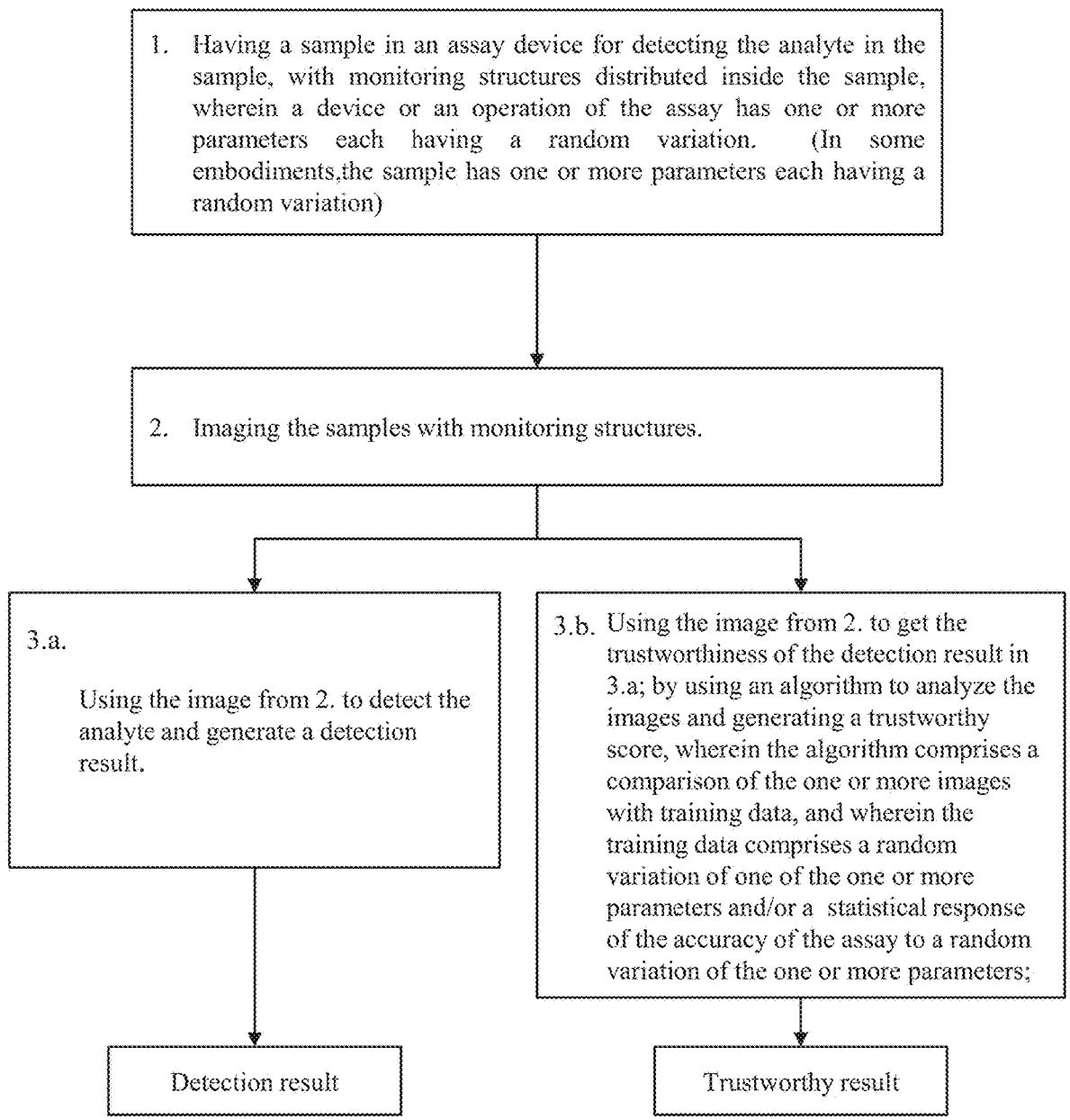
FIG. 2 illustrates a block diagram of embodiment of improving assay accuracy by measuring the trustworthy of the assay device and/or assay operation, wherein monitoring structures are embodied inside the sample. In some embodiments, it check the trustworthy of the sample.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The term "sample" as used herein relates to a material or mixture of materials containing one or more analytes or entity of interest. In certain embodiments, the samples are a bodily fluid sample from the subject. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, exhaled condensates (e.g. breath), hair, finger nails, skin, biopsy, placental fluid, amniotic fluid, cord blood, lymphatic fluids, cavity fluids, sputum, pus, microbiota, meconium, breast milk and/or other excretions. The samples may include nasopharyngeal wash. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient. The samples also can be the sample of food, environments, and others.

The term "analyte" refers to any substance that is suitable for testing in the present invention. An analyte includes, but limited to, atoms, molecules (e.g., a protein, peptides, DNA, RNA, nucleic acid, or other molecule), cells, tissues, viruses, bacteria, and nanoparticles with different shapes. A biomarker is an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemiluminescence. An external excitation can be a combination of the above.

The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The term "spacer" and "optical calibration marks" and "optical calibration marks" and "pillars" are interchangeable.

The term "assay" refers to an investigative (analytic) procedure in and not limited to laboratory, medicine, pharmacology, environmental biology, healthcare, and molecular biology—for and not limited to qualitatively assessing or quantitatively measuring the presence, amount, concentration, or functional activity of a target entity (i.e. the analyte). The analyte can be a drug, a biochemical substance, or a cell in an organism or organic sample such as human blood.

The term "image-based assay" refers to an assaying procedure that utilizes the image of the sample taken by an imager, wherein the sample can be and not limited to medical, biological and chemical sample, The term "imager" refers to any device that can take image of the objects. It includes and not limited to cameras in the microscope, smartphone, or special device that can take image at various wavelength.

The term "sample feature" refers to some property of the sample that represents a potentially interesting condition. In certain embodiments, a sample feature is a feature that appears in an image of a sample and can be segmented and classified by a machine learning model or some other algorithms. Examples of sample features include and not limited to analyte types in the sample, e.g. red blood cells, white blood cells, and tumor cells, and it includes analyte shape, count, size, volume, concentration and the like.

The term "micro-feature in a sample" refers to analytes, microstructures, and/or micro-variations of a matter in a sample. Analytes include particles, cells, macromolecules, such as proteins, nucleic acids and other moieties. Microstructures can refer to microscale difference in different materials. Micro-variation refers to microscale variation of a local property of the sample. Example of micro-variation is a variation of local optical index and/or local mass. Examples of cells are blood cells, such as white blood cells, red blood cells, and platelets.

The term "defects in the sample" refers to foreign objects and artifacts that should not exist in an ideal sample condition or should not be considered in the sample. They can come from and not limited to pollutants, e.g. dusts, air bobbles, etc., and from the peripheral objects, including structural objects in the sample, e.g. monitor marks (such as pillars) in the sample holding device. Defects in the sample can be of significant size and take significant amount of volume in the sample for assaying, e.g. air bubbles, wherein they can appear in different shapes, sizes, amounts, and concentrations in the sample, and they also sample dependent varying from sample to sample.

The term "morphological feature" of the analytes refers to the appearance (e.g. shape, color, size, etc.) and the structure of the analyte.

The term "homographic transform" refers to a class of collineation transforms induced by an isomorphism of the projective spaces. It is known in the field of image processing and it is applied in camera models to characterize the image plane and the corresponding physical plane in the real world.

The term "machine learning" refers to algorithms, systems and apparatus in the field of artificial intelligence that often use statistical techniques and artificial neural networks to give computer the ability to "learn" (i.e., progressively improve performance on a specific task) from data without being explicitly programmed.

The term "artificial neural network" refers to a layered connectionist system inspired by the biological networks that can "learn" to perform tasks by considering examples, generally without being programmed with any task-specific rules.

The term "convolutional neural network" refers to a class of multilayer feed-forward artificial neural networks most commonly applied to analyzing visual images.

The term "deep learning" refers to a broad class of machine learning methods in artificial intelligence (AI) that learn from data with some deep network structures.

The term "machine learning model" refers to a trained computational model that is built from a training process in the machine learning from the data. The trained machine learning model is applied during the inference stage by the computer that gives computer the capability to perform certain tasks (e.g. detect and classify the objects) on its own. Examples of machine learning models include ResNet, DenseNet, etc. which are also named as "deep learning models" because of the depth in their layered network structure.

The term "image segmentation" refers to an image analysis process that partitions a digital image into multiple image patch segments (sets of pixels, often with a set of bit-map masks that cover the image segments enclosed by their segment boundary contours). Image segmentation can be achieved through the image segmentation algorithms in image processing, such as watershed, grabcuts, mean-shift, etc., and it can also be achieved through dedicated machine learning algorithms, such as MaskRCNN, etc.

The term of "unreliable" in an assay's result means that for assaying a given sample, the results of the assay are not always accurate: sometimes the results of the assay are accurate, but other times the results are inaccurate, wherein the inaccurate results are substantially different from accurate results. Such inaccurate result is termed "erroneous result". In some literatures, the erroneous results are also termed "outliers".

The term of "accurate" in an assay's result means that the result of the assay agrees, within an allowed arrange, with the result of the same sample assayed by a gold standard instrument, operated by a trained professional, under an ideal environment.

Traditionally, diagnostic assays usually are performed using sophisticated (often expensive) instruments and require highly trained personnel and sophisticated infrastructures, which are not available in limited resource settings.

The term "a limited resource setting" or "LRS" for assaying a sample refers to a setting in performing an assay, wherein it uses a simplified/low cost assay process or a simplified/low cost instrument, is performed by an untrained person, is used in an adverse environment (e.g. open and non-lab environment with dusts), or any combination of thereof.

The term "LRS assay" refers to an assay performed under LRS.

The term "trustworthy" in describing a reliability of a particular assay result (or data) refers to a reliability analysis of the particular assay result determines that the result has a low probability of being inaccurate.

The term "untrustworthy" in describing a reliability of a particular assay result (or data) refers to a reliability analysis of the particular assay result determines that the result has a high probability of being inaccurate.

The terms "worthiness" and "trustworthy" are interchangeable.

The terms "monitoring structure" means a structure of an optical property that is used to monitor the operation and/or assay device quality of the assay.

The "monitoring structure" comprises monitoring marks, spacers, location marks, imaging marks, or scale marks.

The term "operation conditions" in performing an assay refers to the conditions under which an assay is performed. The operation conditions include, but not limited to, at least three classes: (1) defects related to sample, (2) defects related to the sample holder, and (3) defects related to measurement process. The term "defects" means deviate from an ideal condition.

A1: Sample Defects in the Image-Based Assaying

In the image-based assay, it involves the sample preparation, the sample holding device for imaging, and the image of the sample taken by the imager on the sample holding device for assaying. In the assaying process, defects can occur in all operation actions and components, and they affect the accuracy of the assaying and the trustworthy of the assaying results.

For example, defects from sample preparation include but not limited to, air bubbles, dusts, foreign objects (i.e. objects should not be in the sample, but get into the sample), dry-texture of the sample where certain part of the sample dried out in the sample holding device, insufficient amount of sample for assaying in the sample holding device, sample with incorrect matrix (e.g. blood, saliva), the incorrect reaction of reagents with the sample, the non-uniform distribution of the sample, wrong sample position with the sample holder (e.g. blood cells under spacer), and so forth.

Examples of defects related to the sample holding device include but not limited to, missing spacers in the sample holder, device not closed properly, placed in an improper position, re-opened after being sealed, surface being contaminated, incorrect spacer height, large surface roughness, incorrect transparence, incorrect absorptance, missing monitoring marks, incorrect optical properties, incorrect electrical properties, incorrect geometric (size, thickness) properties, and so forth.

Further examples include defects from the measurement process, including but not limited to, improper light intensity, sample not in focus in the image for assaying, wrong color of the light, the leakage of ambient light, uneven lighting intensity, improper lens conditions, filter conditions, optical component conditions, electrical component conditions, assembling conditions of the instrument, the relative position of sample holding device with the image plan of the imager, and so forth.

Moreover, many defects in the image-based assay, such as air bubbles and dusts, can occur unpredictably, depending on the operation environment, analyte, reagent being used, temperature, and so forth—making it extremely difficult to completely eliminate them in the image-based assaying process. As such, there is a critical need for method and apparatus to detect, remove, and eliminate the negative impacts of defects in the image-based assaying, and to make the assaying results accurate and trustworthy.

Figure 7:
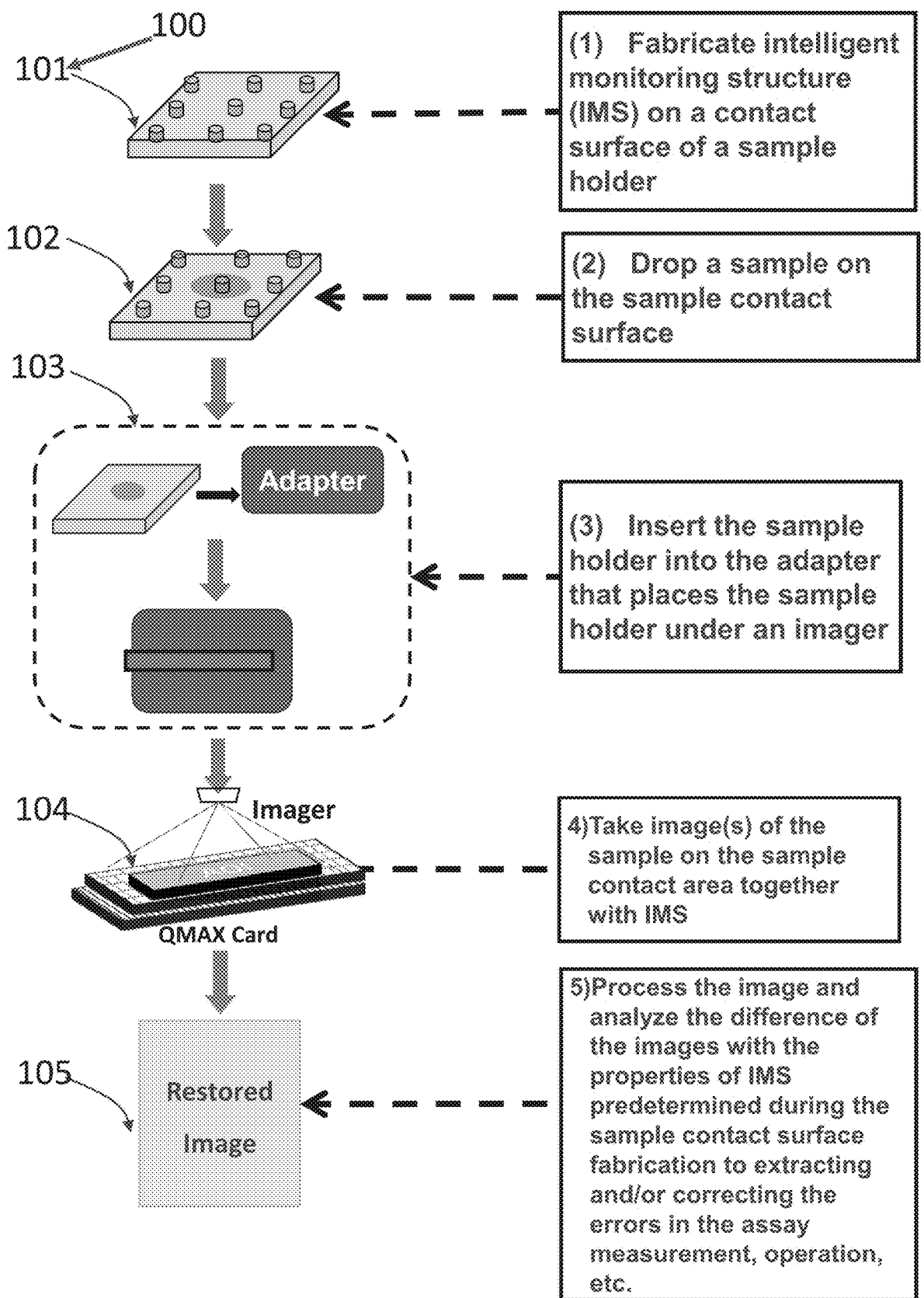
FIG. 7 shows a block diagram of embodiment of sample preparation and imaging using a sample holding device of QMAX card in the image-based assaying

FIG. 7 is a block diagram of process 100 to prepare the sample for assaying in a sample holding device that has some intelligent monitoring structure for image-based assaying. In various implementation of the process 100, actions may be removed, combined, or broken up into sub-actions. The process begins at the action module 101, where the sample holding device is fabricated with high precision using nano imprint, in which it has intelligent monitoring structure (IMS) for monitoring the image-based assaying operations.

As illustrated in FIG. 7, the IMS in the sample holding device comprises of pillars fabricated on the base plate of the device. In some embodiment, these pillars are of uniform height and size, and they distributed in a predesigned periodic pattern. In the action module 102, the sample for assaying is dropped to the sample contact area. The sample contact area may contain reagents, antibodies, antigens, chemicals, and so forth that interacts with the sample and preparing the sample for assaying. In action module 103, the sample holding device of the action module 102 is closed with a transparent cover and the sample holding device containing the sample is sealed with the surrounding walls and its two plates, wherein the sample for assaying is sandwiched between the two plates of the sample holding device. In action module 103, the sealed sample holding device is inserted into an adaptor for imaging. The imager in the action module 104 takes image(s) of the sample holding device, e.g. QMAX card, in the adaptor from the action module 103 on the sample holding contact area together with the intelligent monitoring structure.

Figure 8:
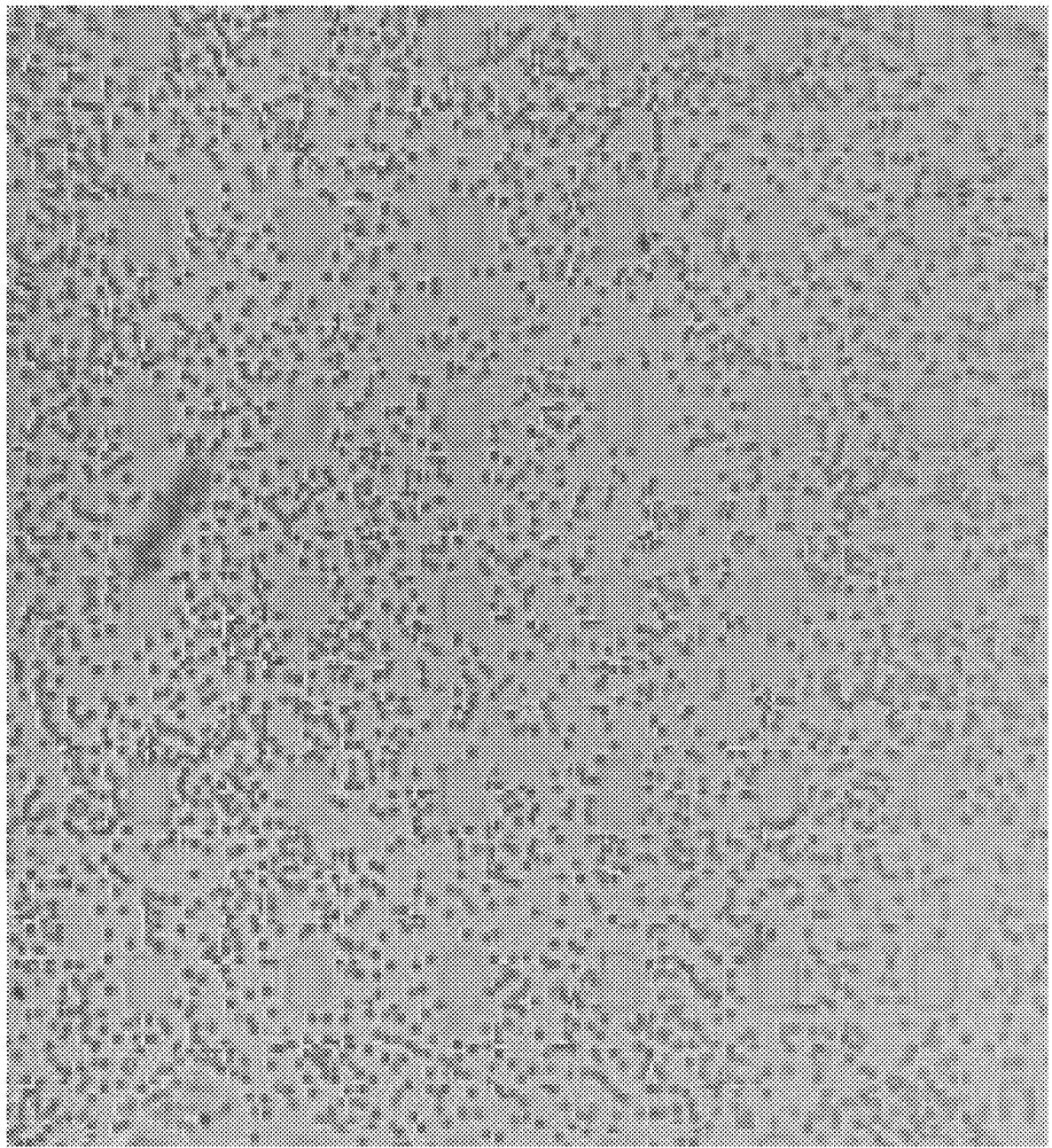
FIG. 8 shows an image of red blood cell taken on the sample holding device of QMAX card for assaying

In the action module 105, the image (s) of the sample for assaying is saved for subsequent image-based assaying operations to analyze the properties of the analytes from the image of the sample. FIG. 8 is an image taken by the imager for the complete-blood-count (CBC) of red blood cells in the image-based assay.

A2: Segmentation of Defects for Image-Based Assay

In some embodiments for verifying the quality and trustworthy of the assaying results, it needs to segment the objects of interest from the image of the sample for assaying. Although machine learning based image segmentation algorithms, such as Mask RCNN, can be applied, they require precise contour labeling of the shape of the objects to be assayed in the microscopic image of the sample in order to train the machine learning model, which is a bottleneck for many applications. For image-based assay, such labeling of the shape contour of the objects can be costly and difficult to come by, because objects in the sample can be very small, their occurrences are random, and moreover, there are huge variations among them in shape, size and colorations (e.g. dusts, air bubbles, etc.).

In some embodiments, a fine-grinned image segmentation algorithm is devised based on a combination of a machine learning based coarse bonding box segmentation and an image processing based fine grind shape determination. It is applied to the image segmentation in the image-based assay, wherein each object only needs to be labeled in a rough bounding box—independent of shape and shape contour details. By which, it eliminates the need of the fine grind labeling of the shape dependent contour of the objects in the image of the sample, which is difficult, complex, costly and hard to be accurate. This fine-grinned image segmentation algorithm comprises:
  a) collecting a plurality of sample images taken by the imager for training which contains the objects to be detected in the image of the sample for assaying;
  b) labeling each object in the collected images with a rough bonding box that contains the said object for model training;
  c) training a machine learning model (e.g. FRCNN) to detect the said objects in the image of the sample with bounding boxes containing them;
  d) in the inference stage; taking the image of the sample for assaying as input;
  e) applying the trained machine learning model to detect the said objects and locate them with bounding boxes in the image of the sample;
  f) transforming each image patch corresponding to a bonding box containing the detected object into gray color and then transforming it to binary with an adaptive thresholding;
  g) performing morphological dilation (7×7) and erosion (3×3) to enhance the contour of the shape from the background noise;
  h) performing convex contour analysis on each said image patch and using the longest connected contour find in the patch as the contour of the object shape to determine the image mask of the object (e.g. binary bit map that covers the object in the image of the sample); and
  i) completing the image segmentation by collecting all image masks from (h).

In some embodiment, it applies segmentation masks on the detected objects with an extra margin Δ to reduce the negative effects of the defects on the local neighboring areas in image-based assaying. As such, the fine-grinned image segmentation described herein further comprises:
  1) dilating each detected contour in (h) with margin Δ as new masks; and
  2) completing the image segmentation with A margin by collecting all enlarged image masks from (1).

FIGS. 9-12 are application examples of applying the described fine-grinned image segmentation algorithm to the image-based assaying for red blood cells. As shown in the images, the described fine-grinned image segmentation method can handle objects with different size and shape and produce segmentation with very tight masks covering the objects in the image of the sample, while even the general form of the shape and size of defects in the image of the sample are unknown. This is quite different from the segmentation of analytes or cells in the sample, e.g. red blood cells in complete-blood-count, where the general form of the shape or size of the analytes or cells are known or known within a certain degree of variations from their basic formations.

Another aspect of the method of image segmentation for defects described herein can not only remove the detected defects in the image of the sample but also remove the defects in the image of the sample by a controlled extra margin Δ. This capability is very important for assaying, because defects in the sample for assaying can change the evenness of the analyte distribution in the sample, change the local sample layer height, and so forth—leading to large variations and inaccuracies in assaying results.

A3: Imaging-Based Assaying Using Monitoring Marks

In image-based assay, an imager of the sample taken by an imager is used for the determination of at least one property of the analyte for assaying. And in some embodiment, the image is taken on the sample in a sample holding device with monitoring marks, such as QMAX card described herein. Many factors can make the image of the sample distorted (i.e. different from a real sample or an image at a perfect condition). The image distortion can lead to inaccuracy and errors in a determination of a property of the analyte. For example, one distortion is the change in the true-lateral-dimension (TLD) in the image of the sample taken by the imager.

The term "lateral dimension" refers to the linear dimension in the plane of a thin sample layer that is being imaged. The term "true lateral dimension (TLD)" and "Field of view (FoV)" are interchangeable in this document.

Determining the TLD of the image of the sample is critical in the image-based assay because it maps the size of the object in the image of the sample described in pixels to its actual size of micrometers in the physical sample plan that is being imaged upon by the imager. Once the TLD of the image of the sample is known, the actual size of the object, such as actual length, area, and so forth, can be determined in the image-based assaying.

Methods of estimating TLD using monitoring marks in the image-based assay are described in PCT/US19/46971, wherein, it utilizes the structural properties of the monitoring marks and machine learning to obtain reliable TLD estimation under the advertise conditions of spherical and barrel lens distortion, strong light scattering and diffractions from particles in the sample, focus conditions by the imager, and so forth.

In addition, methods are also described in PCT/US19/46971 on how to determine the remaining sample volume after certain objects are removed from the image of the sample taken by the imager, utilizing the structure of monitoring marks and properties of the sample holding device, e.g. QMAX card, and machine learning. These methods are applied in the embodiments of the present invention to improve the accuracy of the image-based assaying and the trustworthy of the assaying results in the embodiments described herein.

A4: Removing Defects in the Sample in the Image-Based Assaying

Figure 9:
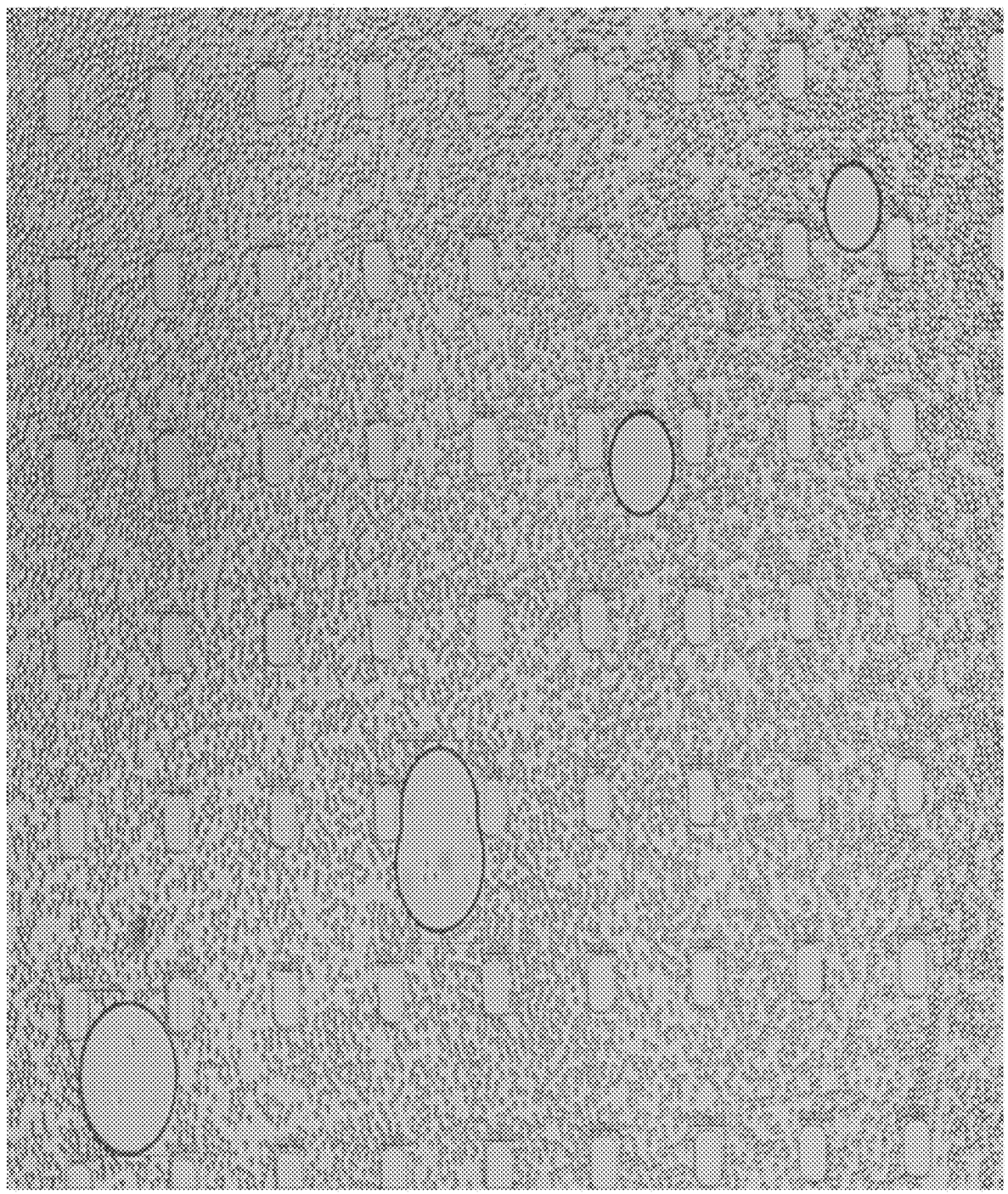
FIG. 9 shows an image of sample for assaying that has air bubbles in the sample for assaying
Figure 11:
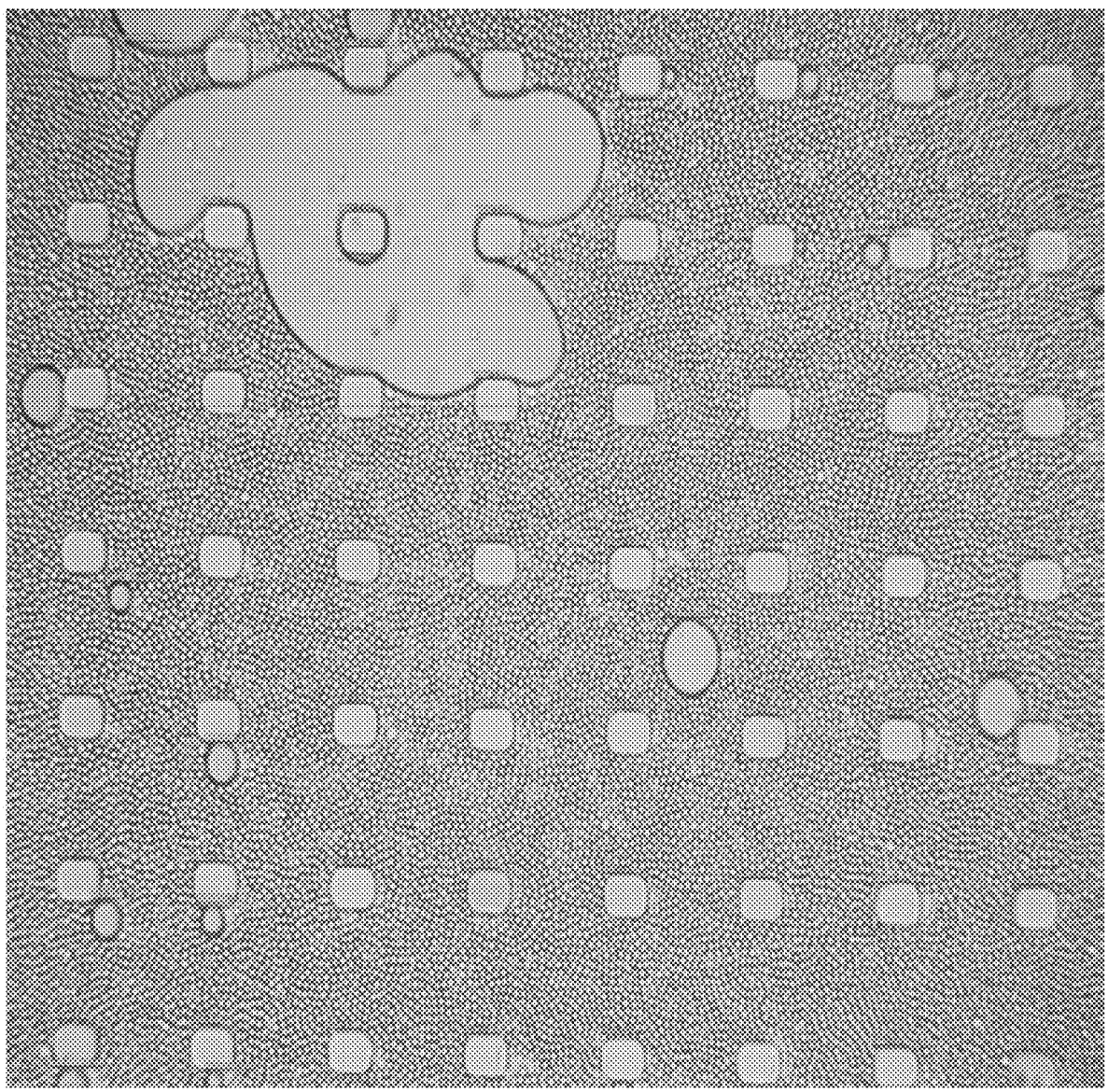
FIG. 11 shows another red cell image of sample for assaying that contains multiple defects
Figure 12:
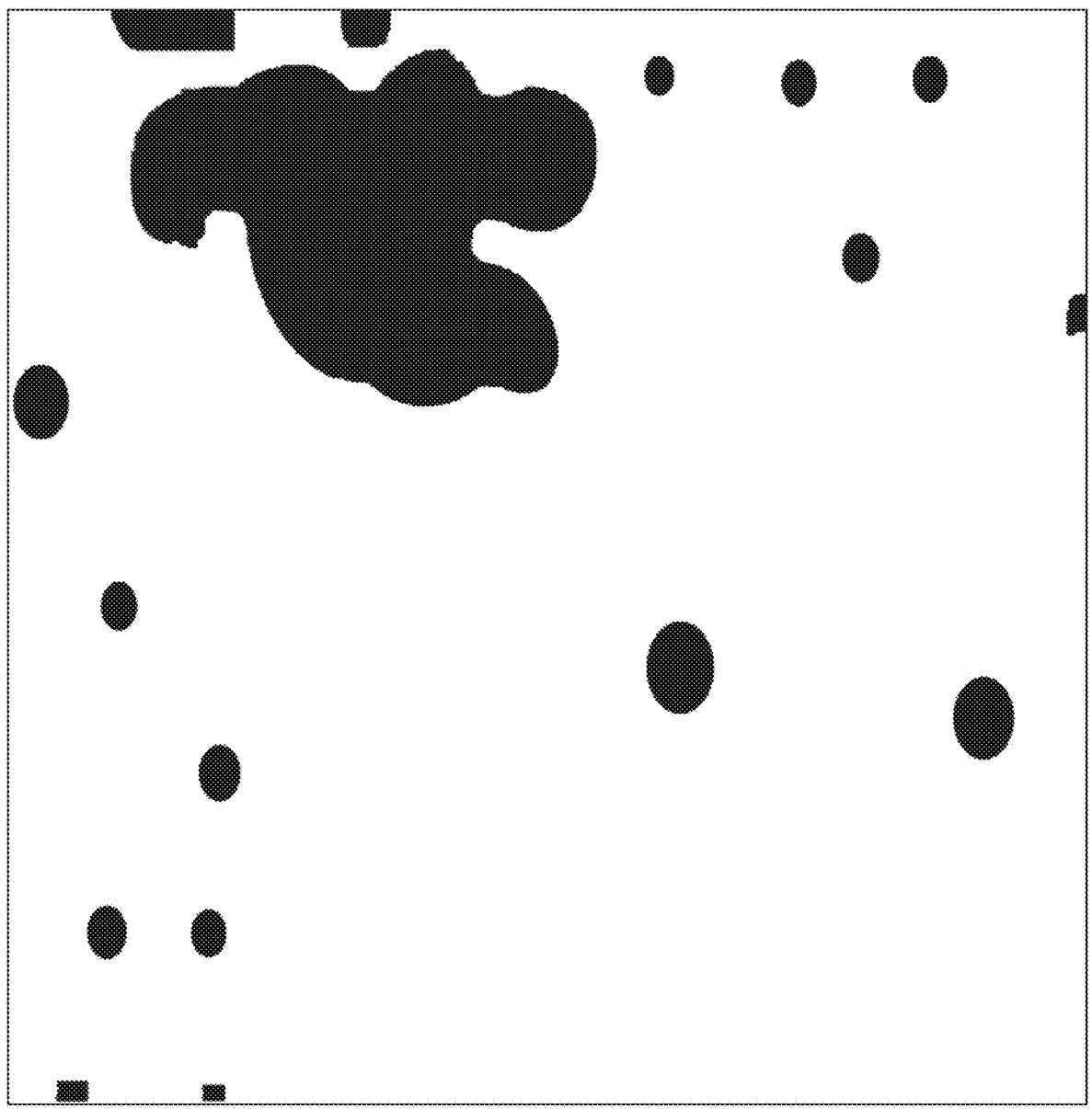
FIG. 12 shows the detected and segmented defects in the image of the sample for assaying from FIG. 12
Figure 13:
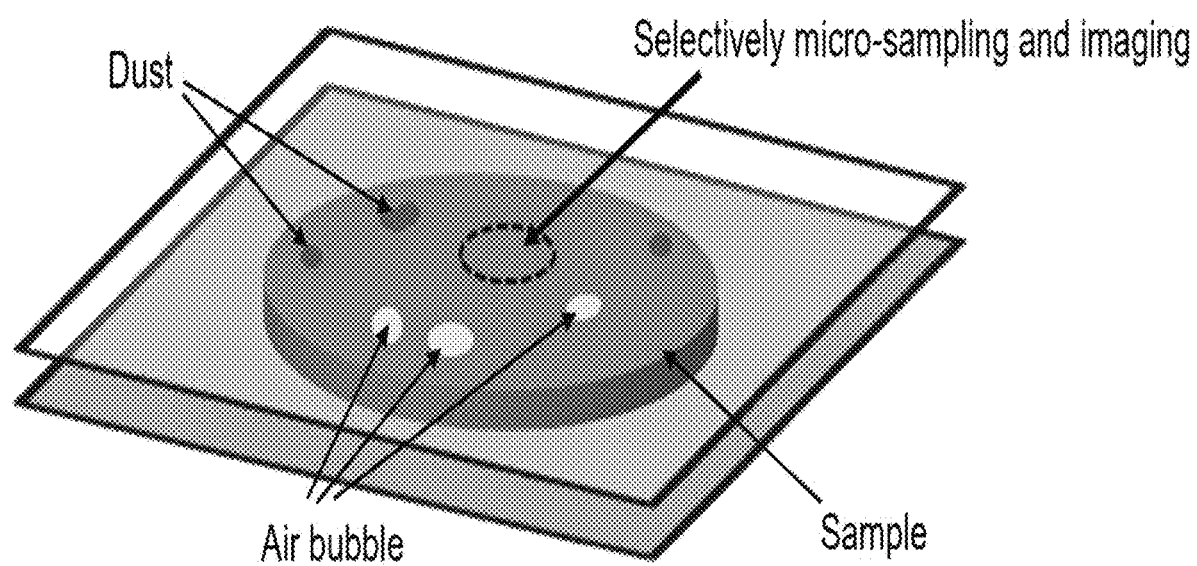
FIG. 13 illustrates the defects in the sample holding device for assaying
Figure 14:
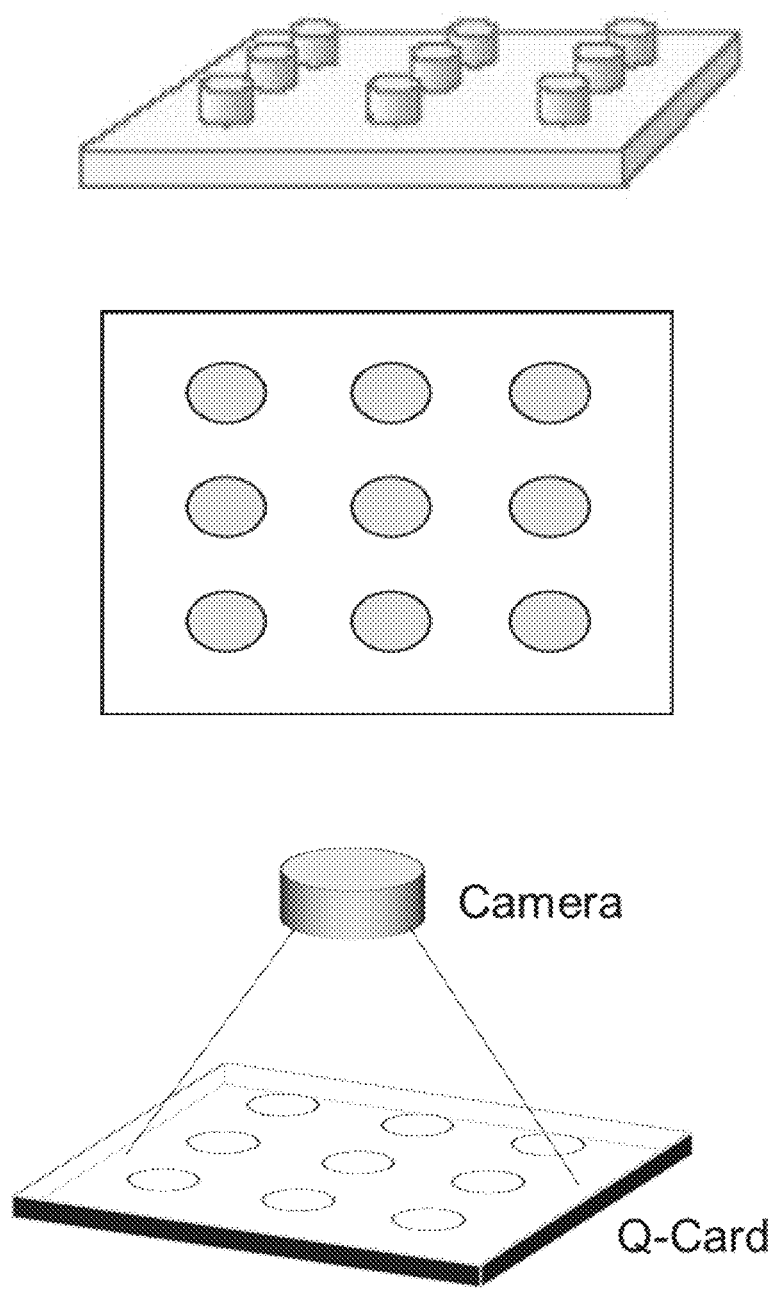
FIG. 14 is a 3 way view of the sample holding device, QMAX card, with monitoring marks and the imaging of the sample holding device in the image-based assay.

Defects in the sample can seriously affect the accuracy and trustworthy of the assaying results, wherein these defects can be any unwanted objects in the sample, including and not limited to dusts, oil, etc. as shown in FIG. 9 and FIG. 11. They are hard to handle once they get into the sample for assaying, because their occurrences and shapes in the sample are all random.

Figure 10:
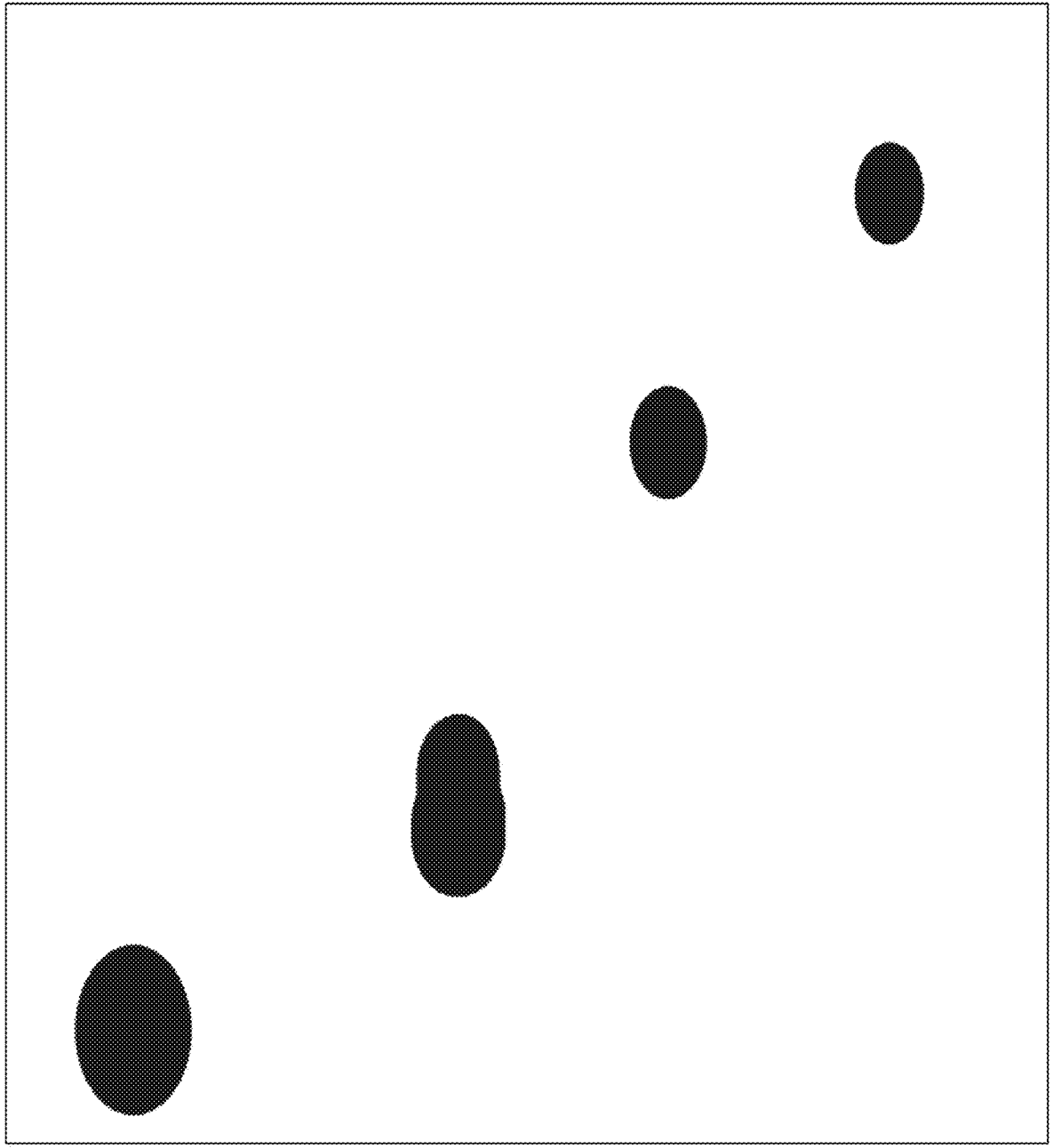
FIG. 10 shows the detected and segmented sample defects in the red blood cell image of the sample of FIG. 9 with covering masks in an embodiment of the described approach

In some embodiment, a dedicated process for defects detection is devised and applied to image-based assay, wherein images of good samples without the defects and images of samples with various degree of defects in the sample are collected as training data—from which defect areas in the image are labeled by a bonding box, A machine learning model (e.g. Fast RCNN) is selected and trained with the labeled training images—to detect the defects in the image of the sample in bonding boxes, and following that, the described fine-grinned image segmentation method described in previous section A2 is applied to determine the segmentation contour masks that covering them. FIG. 10 and FIG. 11 are images of the segmented defects from the image of the sample of FIGS. 9 and 12 in the complete-blood-count for red blood cell using the described fine-grind segmentation method described in section A2.

During the image-based assaying process, defects detection and area determination are performed to verify the trustworthy of the assaying results, comprising:

a) taking the image of the sample from the imager as input;
b) applying the trained defect detection machine learning model (e.g. Fast RCNN) to the image of the sample for assaying to detect the defects and locating them in bonding boxes;
c) determining segmentation contour masks of the detected defects using the fine-grinned image segmentation method described in section A2;
d) estimating the TLD of the image of the sample utilizing the monitoring marks and sample holding device described in section A3;
e) utilizing the estimated TLD from (d) to determine the total areas occupied by the defects, i.e. defects-area-in-AoI, in the area-of-interest (AoI) for assaying by summing up all areas of segmentation masks covering the detected defects;
f) determining the area ratio between the defects-area-in-AoI and area-of-AoI for assaying in the image of the sample: ratio-defects-area-in-AoI=defects-area-in-AoI/area-of-Ao-for-assayingI; and
g) raising the flag on the trustworthy of the assaying results, if the ratio-defects-area-in-AoI exceeding a certain threshold.

In some embodiment, the training of the machine learning model in (b) comprises:

i. collecting a plurality of image of assaying samples for model training;
ii. labeling the defects in the image from the training image of the sample from (i) by bounding boxes;
iii. selecting a machine learning model in the form of a convolutional neural network, such as FastRCNN;
iv. adjusting the parameters of the selected machine learning model against a loss function in the training to classify the training samples to their correct identity, by iterating through the said plurality of samples with bounding box labeled defects for training; and
v. outputting the machine learning model from (iv) when certain stopping conditions are met.

In some embodiment, the threshold of determining the threshold in (g) based on the ratio-defects-area-in-AoI is around 15%, wherein this threshold depends on the remaining sample volume after removing the sample volume corresponding to the area influenced by defects and wherein the volume of sample after defects removal can be obtained using the method of sample volume estimation from the image of the sample described in section A2, A3, and the constant height property of the said sample holding device.

In some embodiment, the removed objects are air bubbles that occur in the sample for assaying. In some embodiment, the removed objects are dusts, hairs, etc., that get into the sample in the operation of image-based assaying.

In some embodiment, the removed objects and related volume can be the monitoring marks and volume they took in the sample holder, such as pillars, which take part in the image of the sample for assaying but should not be counted in the actual sample volume for assaying. Otherwise, the assaying results are not accurate or trustworthy, because of the incorrect sample volume used.

A5: Removing Aggregated Analytes in the Sample

In assaying, one troublesome situation is analytes aggregation in the sample for assaying, and this can affect the assaying results and accuracy, such as counting, segmentation, and so forth.

Moreover, analytes aggregation can be caused by operations in sample preparation, the type of analytes, time duration of the sample in the sample holding device, the freshness of the sample, the reagents being used, and so forth. Further, analytes aggression is a moving process. It can get worse with the time and should be checked step-by-step in assaying.

For example, in complete blood count, certain part of the red blood cells in the sample for assaying can be aggregated, especially if they are exposed in the open air for certain period of time. Aggregated analyte clusters in the sample have some random size and shape depending on how they are aggregated together. If the portion of the aggregated analytes exceeds a certain percentage in the sample, the sample should not be used for assaying.

In some embodiment, a process using machine learning for analyte aggregation detection and removal is devised. It treats the analyte aggregation/clusters as special defects in the sample for assaying, that are dynamic and varying with time. As such, it checks the image of the sample taken by the imager at each step of the assaying to determine if analytes are aggregated/clustered in the sample for assaying.

In some embodiment, a plurality of image of samples are collected for training a machine learning model to detect and segment the analyte aggregation/clusters in the image of the sample. The collected training image set includes images of samples without analyte clustering and images of samples with various degrees of clustering. It follows a similar machine learning model training procedure described in section A4 by labeling the analyte aggregation/clusters in the image of the sample by bounding boxes. It trains a machine learning model based on the bounding box labeling of the training data to detect the analyte aggregation/clusters in the image of the sample during the inference process. And after that, it applies the fine grinned image segmentation method described in section A2 on the detected bounding boxes that contain analyte aggregation/clustering in the image of the sample.

During the assaying, analyte aggregation/clusters detection and removal comprises:
a) taking the image of the sample from the imager as input;
b) applying the trained machine learning model for analytes aggregation/clusters detection to detect the aggregated analytes in the image of the sample for assaying in bonding boxes;
c) determining the fine-grinned segmentation contour masks of the detected analyte aggregation/clusters from (b) by applying the fine grinned image segmentation method described in section A2;
d) determining the total area (area-aggregated-analytes-in-AoI) occupied by the aggregated analytes in the area-of-interest (AraI) in the image of the sample, by summing up all areas associated with the segmentation contour masks that cover them from (c);
e) determining the area ratio between the area-aggregated-analytes-in-AoI and the area-of-AraI in the image of the sample:
ratio-aggregated-analytes-area-in-AoI=area-aggregated-analytes-in-AoI/area-of-AoI; and
f) raising flag on the trustworthy of the assaying results, if the ratio-aggregated-analytes-area-in-AoI exceeds a certain threshold.

In some embodiment, the threshold is set to 10-20%, wherein the threshold depends on the influence of the aggregated analytes area to the final estimation, which can be estimated from the training and evaluation data.

A6: Removing Air Bubbles in the Sample for Image-Based Assaying

Air bubbles in the sample for assaying is a special type of defects and they occur quite frequently in assaying. Their occurrences are random—which can come from the operation procedures in sample preparation, reactions between the analytes and reagents in the sample, and so forth.

In some embodiment of the present invention, it uses a dedicated process to treat air bubbles as a special defect for removing them in assaying. In some other embodiment, it adds air bubbles as a new type of defects in the procedure of removing defects described in Section A4. The described fine-grinned image segmentation method described in Section A2 is applied to do fine grinned segmentation and segmentation of the defects with an enlarged margin Δ to make the assaying results accurate and trustworthy.

In some embodiment, it follows the process described in A4 and determine the total area of air bubbles in the image of the sample and calculate the ratio of the air bubbles area in the area of interest for assaying: ratio-air-bubbles-in-AoI. It raises the flag on the trustworthy of the assaying results, if the ratio-air-bubbles-in-AoI exceeds a certain threshold. In some embodiment, the threshold for air bubbles is set around 10%, wherein the threshold depends on the influence of air bubble areas to the final estimation, which can be estimated from the training and evaluation data.

In some embodiment, a tighter threshold on air bubbles is applied, because a large amount of areas occupied by air bubbles is an indication of some chemical or biological reactions happened among the components in the sample for assaying or some defects/issues in the sample holding device that deserve special attention, A7: Removing Dry-Texture in the Sample for Image-Based Assaying Dry-texture in the image of the sample for assaying can affect the accuracy and trustworthy of the assaying results in image-based assay. This happens when the amount of the sample for assaying is below the required amount or certain portion of the sample in the image holding device dried out due to some unpredictable factors.

In some embodiment, a process based on machine learning is devised and applied to detect dry-texture areas in the image of the sample taken by the imager in the image-based assay. It treats the dry-texture in the sample for image-based assaying as a special type of defects in the sample, and follows the procedure described in section A4 for its detection and removal. A plurality of samples is collected for training the machine learning model for detecting dry-texture in the sample for assaying that contains images of the sample with various degrees of dry-texture areas.

During the image-based assaying, the image of the sample is checked for dry-texture following the procedure described in Section A4. The machine learning based dry-texture detection is applied to check the image of the sample for assaying. The detected dry-textures by the pre-trained machine learning model is used to locate the dry-textures into bounding boxes. The fine-grinned image segmentation method described in Section A2 is applied to generate the fine grinned segmentation of the detected dry-texture. The total area of the detected dry-texture is estimated using the estimated TLD (true-lateral-dimension) described in Section A3 and summing up all mask areas of the detected dry-texture.

In some embodiment, it calculates the ratio between the area-dry-texture-in-AoI and the area-of-AoI for assaying: ratio-dry-texture-area-in-AoI=area-dry-texture-area-in-AoI/area-of-AoI. And it raises the flag on the trustworthy of the assaying results, if the ratio-dry-texture-area-in-AoI exceeds a certain threshold.

In some embodiment, the threshold is set around 10%, wherein the threshold depends on the influence of dry-texture area to the final estimation result, which can be estimated from the training and evaluation data.

A8: Detecting Objects on Pillars in the Image-Based Assaying

As described previously, in some embodiment, the monitoring marks in the form of pillars are used in the sample holding device to make the gap between two plates uniform in the image-based assaying. This uniformness of the gap in the sample holding device is critical to control the sample volume for assaying. But this can be disturbed if some analytes or foreign objects get on top of the pillar and between the pillar and the top plate of the sample holding device. If this happens, the gap of the sample holding device will not be of uniform height and has an increased height around the pillar with analytes or foreign objects on top.

In some embodiment, it detects the pillars in the image of the sample as in Section A4, but it also detects other defects and analytes in the image using separately trained machine learning model. In some embodiment, it builds one large machine learning model that covers pillars, analytes, air bubbles, dusts, etc. as different object class. In the inference stage; it detects all objects belongs to each class. It applies the method of Section A2 to segment out the pillars from the image of the sample. Then it applies the method of Section A2 to segment out other detected objects of analytes, dusts, and air bubbles. The method of detecting analytes, dusts, and air bubbles on top of the pillars further comprises:
  a) intersecting the segmentation masks of detected analytes, dusts, and air bubbles with the segmentation masks of pillars in the image of the sample;
  b) identifying the affected pillars whose segmentation masks having non-empty intersection with the segmentation masks of analytes, dusts, and air bubbles;
  c) discarding the image of the sample for assaying if the number of the affected pillars exceeding a preset threshold;
  d) removing the effected pillars with a margin Δ in the image of the sample for assaying following the method described in Section A4 if only the affected pillars are few in the image of the sample;
  e) updating the sample volume by excluding the sample volume corresponding to the removed affected pillars with a margin Δ in the image of the sample; and
  f) updating sample volume according to (d) and (e) and performing the image-based assaying based on the updated assaying samples.

A9: Detecting Missing Pillars in the Sample Holding Device

In some cases, the sample holding device can have its own defects. In particular, the monitoring marks, e.g. pillars in the sample holding device such as AMAX card, can be missing or broken in the assaying operation. When this happens, it can change the gap or the sample thickness in the sample holding device, and the actual sample volume for assaying will be different.

In some embodiment of the present invention, it treats monitoring marks, such as pillars, as a special type of defects in the sample for assaying. It uses the method described in Section A4 to detect the pillars in the image of the sample, and determine if some pillars are missing in the sample holding device—an indication that the device itself has defects. Furthermore, it uses the fine-grinned segmentation of Section A2 to identify the shape of the detected pillars, and based on that, it detects the broken pillars in the sample holding device that are also from defects in the sample holding device.

In some embodiment, it combines the detection of objects on top pillars, the missed pillars in the sample holding device and the broken pillars in the sample holding device in one process, following the method and process described in Section A4. In some embodiment; this becomes an important verification process to determine if the sample holding device in assaying is properly closed (e.g. no objects on top of pillars), and the sample holding device is not defective (e.g. no missing pillars, or broken pillars).

A10: Evenness of Analyte Distribution in the Sample

One factor that affects the trustworthy of the assaying results is the evenness of the analytes distribution in the sample, and this is hard to detect by eyeball checking even with the experienced technicians.

In some embodiment, a method to determine the evenness of the analyte distribution in the sample for assaying is devised and applied based on the image of the sample for assaying. It collects a plurality of images of samples taken by the imager in assaying for training an analyte detection machine learning model such as F-RCNN.

During the assaying, the method of determining the evenness of analytes in the sample for assaying comprises:
  a) taking the image of the sample for assaying as input;
  b) partition the image of the sample from (a) into equal-sized and non-overlapping image patches (e.g. 8×8 equal-sized small image patches);
  c) applying the trained machine learning model for analyte detection to each partitioned image patch from (b);
  d) determining the analyte concentration in each patch;
  e) sorting the analyte concentration of the image patches based on (d) in ascending order and determining its 25% quantile Q1 and its 75% quantile Q3 in the sorted concentration sequence of the portioned image patches of (b);
  f) applying an inter-quantile-range (IQR) based confidence measure on the concentration sequence from (e) and calculating the IQR based confidence measure $$\text{confidence-IQR} = (Q3 - Q1)/(Q3 + Q1); \text{ and}$$

if the confidence-IQR exceeds a certain preset threshold, raise the flag that analytes are unevenly distributed in the image of the sample for assaying, and the assay result may not be reliable. In some embodiment, the threshold is set at 30%, wherein the threshold depends on the tolerance of the assaying to the uneven distribution of the analytes in the sample. Such tolerance of the assaying to the uneven distribution of analytes can be estimated from the training and evaluation assaying data.

A12: Detecting Operation Faults in the Image-based Assay

Operation fault is another source for inaccuracy and unreliable assaying results. One such fault is not enough sample in the sample holding device or overflow of samples in the sample holding device for assaying.

In some embodiment, it uses the special sample holding device, such as QMAX card, to hold the sample for assaying, wherein the sample for assaying is sandwiched in the gap of two parallel plates of the sample holding device, and the gap between the two plates in the sample holding device is known and relative to the analytes to be assayed.

In some embodiment, it detects the contour of sample for assaying in the image of the sample, and estimate the total area enclosed by the sample contour in the image, wherein the total sample volume can be determined by the actual sample area in the image of the sample and the uniform height of the gap of the sample holding device characterized by the monitoring marks such as pillars in QMAX card. The actual area of the sample contour can be determined by the TLD (true-lateral-dimension) of the image of the sample with the method described in Section A3. If the actual sample volume calculated from the image of the sample by removing monitoring masks, pillars, air bubbles, dusts, and so forth, is below the required volume for assaying, it will abort the assaying process with an error message indicating not enough sample for assaying.

Another operation fault causing the assaying accuracy is re-open a closed sample holding device such as QMAX card and re-close it again. One observation is that when a closed sample holding QMAX card is closed with the blood sample being opened again and then closed, it will leave an identifiable blood contour mark on the bottom plate of the QMAX card, wherein a significant amount of sample blood tends to redistributed on both piece of the QMAX card when the top and bottom plates of the sample holding device are separate and close again.

When the sample holding device is closed again, part of the blood sample will redistribute and cover a slightly different area leaving a contour mark visually identifiable. In addition, the newly generated sample area is not going to be identical to the original covered area.

In some embodiment, it detects the double borders in the image of the sample to determine if the sample holding device has been re-opened after the first closure and then being closed again.

In addition, sample overflow in the sample holding device is another type of operation fault in the image-based assaying. In some embodiment, it uses the sample border detection in the image of the sample for assaying to determine the sample overflow in the sample holding device. The sample border detection in the image of the sample is determined by the image contour analysis using method described in Section A2 that treats the entire image of the sample as one special large bounding box.

In the image-based assaying, one type of faults happened in assaying operation is using a wrong sample holding device with incorrect specification for the analysis. In some embodiment, it puts a special code on the upper side of the plate of the sample holding device, e.g. QMAX card, to specify the property of the device and the intended assaying use of this card, which can be imaged with the sample in sample holding device by the imager. This special code can be recognized from the image of the sample to determine if correct sample holding device is used for assaying and the assaying process will stop if wrong card is used in the assaying process.

In some embodiment, it encodes the property of the sample holding device, e.g. QMAX card, using the shape and distribution of the monitoring marks, e.g. pillars, in the sample holding device. In embodiment, methods in Section A4 is applied to detect the pillars in the image of the sample, determine their size and distribution pattern by which the property of the sample holding device and its intended assaying application is determined to eliminate the operation fault of using wrong sample holding device for assaying.

A12: Focus Checking in Image-Based Assay

In image-based assay, the image of the sample taken by the imager needs to be in focus on the sample by the imager for assaying, and off focus in the image of the sample taken by the imager blurs analytes in the image of the sample. And consequently, the assaying results become unreliable. However, there are many factors that can cause the image of the sample being partially or even totally off focus, including and not limited to vibrations and hand-shaking during the image taken process, the mis-placement of the sample holding device to the image sensor plane, and so forth. Moreover, prior art mostly relies on certain edge content-based measure, e.g. Tenengrad measure, etc., with some preset content dependent thresholds, which can be unreliable, fragile, and falls short for the requirements of the image-based assay.

In some embodiment, a verification process based on machine learning is devised and applied to determine if an image of the sample taken by an imager is in or off focus in the image-based assay. It collects a plurality of images of the sample for assaying taken by the imager under both in focus and off focus conditions and use it as the training data. The images in the collected training data are labeled based on their known focus conditions. A machine learning model such as DenseNet is selected and it is trained with the labeled training data. During the assaying process, the trained machine learning model for classifying the focus condition in the image of the sample is applied, and it is to detect if the image of the sample taken by the imager is in focus in its inference process. From which, it can determine if the image of the sample should be retaken to make the assaying result more reliable.

In some embodiments, the predesigned monitor marks on the sample holding device, such as QMAX card, is utilized to serve as reference or anchors to assist the determination of the focus quality in the image-based assay.

B1: Embodiments of Improving the Trustworthy of the Image-Based Assay

In an imaging based assay for assaying an analyte in a sample, an imager is used to create an image of the sample which is on a sample holder, and the image is used in a determination of a property of the analyte.

However, many factors can make the image distorted (i.e. different from a real sample or an image in a perfect condition). The image distortion can lead to inaccuracy in a determination of a property of the analyte. For example, one fact is poor focusing, since a biological sample itself does not have a sharp edge that is preferred in a focusing. When the focusing is poor, the object dimension will be different from the real object, and other object (e.g. blood cells) can become unidentifiable. Another example is that a lens might be perfect, causing different location of the sample having different distortion. And another example is the sample holder is not in the same plane as the optical imaging system, causing a good focus in one area and poor focusing in other area.

The present invention is related to the devices and methods that can get a "true" image from a distorted image, hence improving the accuracy of an assay.

One aspect of the present invention is the devices and methods that use monitoring marks that has an optical observable flat surface that is parallel to neighboring surface Another aspect of the present invention is the devices and methods that use a QMAX card to make at least a part of the sample forming a uniform layer and use monitoring marks on the card to improve the assay accuracy Another aspect of the present invention is the devices and methods that use monitoring marks to together with computational imaging, artificial intelligence, and/or machine learning.

The term "lateral dimension" refers to the linear dimension in the plane of a thin sample layer that is being imaged.

The term "true lateral dimension (TLD)" and "Field of view (FoV)" are interchangeable.

The term "micro-feature in a sample" can refer to analytes, microstructures, and/or micro-variations of a matter in a sample. Analytes refer to particles, cells, macromolecules, such as proteins, nucleic acids and other moieties. Microstructures can refer to microscale difference in different materials. Micro-variation refers to microscale variation of a local property of the sample. Example of micro-variation is a variation of local optical index and/or local mass. Examples of cells are blood cells, such as white blood cells, red blood cells, and platelets.

A. Monitoring Marks on a Solid-Phase Surface

A1-1. A device for assaying a micro-feature in a sample using an imager, the device comprising:
 (a) a solid-phase surface comprising a sample contact area for contacting a sample which contains a micro-feature; and (b) one or more monitoring marks, wherein the monitoring marks:
  i. are made of a different material from the sample;
  ii. are inside the sample during an assaying the microstructure, wherein the sample forms, on the sample contact area, a thin layer of a thickness less than 200 um;
  iii. have their lateral linear dimension of about 1 um (micron) or larger, and
  iv. have at least one lateral linear dimension of 300 um or less; and
wherein during the assaying at least one monitoring mark is imaged by the imager wherein used during assaying the analyte; and a geometric parameter (e.g. shape and size) of the monitoring mark, and/or a pitch between monitoring marks are (a) predetermined and known prior to assaying of the analyte, and (b) used as a parameter in an algorithm that determines a property related to the micro-feature.

A1-2. A device for assaying a micro-feature in a sample using an imager, the device comprising:
  a solid-phase surface comprising a sample contact area for contacting a sample which contains a micro-feature; and
  one or more monitoring marks, wherein each monitoring mark comprises either a protrusion or a trench from the solid-phase surface, wherein:
    v. the protrusion or the trench comprises a flat surface that is substantially parallel to a neighbor surface that is a portion of the solid-phase surface adjacent the protrusion or the trench;
    vi. a distance between the flat surface and the neighboring surface is about 200 micron (um) or less;
    vii. the flat surface an area that has (a) a linear dimension is at least about 1 um or larger, and (b) at least one linear dimension 150 um or less;
    viii. the flat surface of at least one monitoring mark is imaged by an imager used during assaying the micro-feature; and
    ix. a shape of the flat surface, a dimension of the flat surface, a distance between the flat surface and the neighboring surface, and/or a pitch between monitoring marks are (a) predetermined and known prior to assaying of the micro-feature, and (b) used as a parameter in an algorithm that determines a property related to the micro-feature.

B. Monitoring Marks on QMAX Card

A2-1. A device for assaying a micro-feature in a sample using an imager, the device comprising:
  a first plate, a second plate, spacers, and one or more monitoring marks, wherein:
    i. the first plate and the second plate are movable relative to each other into different configurations;
    ii. each of the first plate and the second plate comprises an inner surface comprising a sample contact area for contacting a sample that contains a micro-feature;
    iii. one or both of the first plate and the second plate comprises the spacers that are permanently fixed on the inner surface of a respective plate,
    iv. the spacers have a substantially uniform height that is equal to or less than 200 microns, and a fixed inter-spacer-distance (ISD);
    v. the monitoring marks are made of a different material from the sample;
    vi. the monitoring marks are inside the sample during an assaying the microstructure, wherein the sample forms, on the sample contact area, a thin layer of a thickness less than 200 um; and
    vii. the monitoring marks have their lateral linear dimension of about 1 um (micron) or larger, and have at least one lateral linear dimension of 300 um or less;
wherein during the assaying at least one monitoring mark is imaged by the imager wherein used during assaying the micro-feature; and a shape of the flat surface, a dimension of the flat surface, a distance between the flat surface and the neighboring surface, and/or a pitch between monitoring marks are (a) predetermined and known prior to assaying of the micro-feature, and (b) used as a parameter in an algorithm that determines a property related to the micro-feature;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and
wherein a monitoring mark is (i) a different structure from the spacers, or (ii) the same structure that is used as a spacer.

A2-2. A device for assaying a micro-feature in a sample using an imager, the device comprising:
  a first plate, a second plate, spacers, and one or more monitoring marks, wherein:
    viii. the first plate and the second plate are movable relative to each other into different configurations;
    ix. each of the first plate and the second plate comprises an inner surface comprising a sample contact area for contacting a sample that contains a micro-feature;
    x. one or both of the first plate and the second plate comprises the spacers that are permanently fixed on the inner surface of a respective plate,
    xi. the spacers have a substantially uniform height that is equal to or less than 200 microns, and a fixed inter-spacer-distance (ISD);
    xii. each monitoring mark comprises either a protrusion or a trench on one or both of the sample contact areas;
    xiii. the protrusion or the trench comprises a flat surface that is substantially parallel to a neighbor surface that is a portion of the solid-phase surface adjacent the protrusion or the trench;
    xiv. a distance between the flat surface and the neighboring surface is about 200 micron (um) or less;
    xv. the flat surface an area that has (a) a linear dimension is at least about 1 um or larger, and (b) at least one linear dimension 150 um or less;
    xvi. the flat surface of at least one monitoring mark is imaged by an imager used during assaying the micro-feature; and
    xvii. a shape of the flat surface, a dimension of the flat surface, a distance between the flat surface and the neighboring surface, and/or a pitch between monitoring marks are (a) predetermined and known prior to assaying the micro-feature, and (b) used as a parameter in an algorithm that determines a property related to the micro-feature.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein a monitoring mark is (i) a different structure from the spacers, or (ii) the same structure that is used as a spacer.

A3. A device for imaging based assay, comprising:
a device of any prior device embodiment, wherein the device has at least five monitoring marks wherein at least three of the monitoring marks are not aligned on a linear line.

A4. An apparatus for assaying an analyte in a sample using an imager, the system comprising:
(a) a device of any prior device embodiment; and
(b) an imager that is used in assaying a sample of containing an analyte.

A5. A system for performing an imaging-based assay, the system comprising:
(a) a device of any prior device embodiment;
(b) an imager that is used in assaying a sample of containing an analyte; and
(c) An algorithm that utilizes the monitoring marks of the device to determine a property related to the analyte.

In some embodiments, the thickness of the thin layer is configured, so that for a given analyte concentration there are monolayer of analytes in the thin layer. The term "monolayer" means that in the thin sample layer, there is no substantial overlap between two neighboring analyte in the direction normal to the plane of the sample layer.

C. Monitoring Marks with Computation Imaging Artificial Intelligence and/or Machine Learning Another aspect of the present invention is to combining the monitoring marks with computational imaging, artificial intelligence and/or machine learning. It utilizes a process of forming the images from measurements, using algorithms to process the image and map the objects in the image to their physical dimensions in real world. Machine learning (ML) is applied in the present invention to learn the salient features of the objects in the sample, embedded in the ML models built and trained from the images of the sample taken by the imager. Intelligent decision logic is built into and applied in the inference process of the present invention to detect and classify the target objects in the sample according to the knowledge embedded in the ML models. Computational Imaging is the process of indirectly forming images from measurements using algorithms that rely on a significant amount of computing.

A6. A system for assaying an analyte in a sample using an imager, the system comprising:
(a) a device of any prior device embodiment;
(b) an imager that is used in assaying a sample of containing an analyte; and
(c) An algorithm that utilizes monitoring marks of the device to assay a property related to the analyte, wherein the algorithm uses machine learning.

A7. A method for assaying an analyte in a sample using an imager, comprising:
(a) obtaining a device, apparatus, or a system of any prior embodiment;
(b) obtaining a sample and depositing the sample on a sample contact area in the device, apparatus, or system in (a), wherein the sample contains an analyte; and
(c) assaying the analyte.

8. A method for assaying an analyte in a sample using an imager, comprising:
(a) obtaining a device, apparatus, or a system of any prior embodiment;
(b) obtaining a sample and depositing the sample on a sample contact area in the device, apparatus, or system in (a), wherein the sample contains an analyte;
(c) assaying the analyte, wherein the assaying comprise a step of using machine learning.

One key idea of the present invention is to use pillars in the sample holding device, e.g. QMAX device, as detectable anchors for calibration and improving the accuracy of image-based assay. In QMAX device, pillars are monitor marks to keep the gap between the two plates that holds the sample in the sample holding device uniform. However, detecting pillars accurately in the sample holding device as anchors for calibration and improving the accuracy of the assay is a challenge, because pillars are permeated and surrounded by the analytes inside the sample holding device. And moreover, their images are distorted and blurred in microscopic imaging from the spherical (barrel) distortion of the lens, light diffraction from microscopic objects, defects at microscopic level, mis-alignment in focusing, noise in the sample image, etc. And it becomes more difficult if imaging is taken by commodity devices (e.g. cameras from smart phones), because those cameras are not calibrated by the dedicated hardware once they left the manufacture.

In the present invention, the pillar detection is formulated into a machine learning framework—to detect pillars in the sample holding device (e.g. QMAX device)—with an accuracy suitable for calibration and accuracy improvement in image-based assay. Since the distribution and physical configuration of the pillars are known priori and controlled by fine nanoscale fabrication, e.g. QMAX device, it makes this innovative approach of using detectable monitor marks, e.g. pillars, as anchors in image-based assay not only feasible but also effective.

In some embodiments, the algorithm of any prior embodiment comprises an algorithm of computational imaging, artificial intelligence and/or machine learning.

In some embodiments, the algorithm of any prior embodiment comprises an algorithm of machine learning.

In some embodiments, the algorithm of any prior embodiment comprises an algorithm of artificial intelligence and/or machine learning.

In some embodiments, the algorithm of any prior embodiment comprises an algorithm of computational imaging, and/or machine learning.

An embodiment of the present invention comprises:
(1) Using a sample loading device in image-based assay, e.g. QMAX device, wherein there are monitor marks with known configuration residing in the device that are not submerged in the sample and can be imaged from the top by an imager in the image-based assay;
(2) take the image of the sample in the sample loading device including analytes and monitor marks;
(3) build and train a machine learning (ML) model for detecting the monitor marks in the sample holding device from the images taken by the imager;

(4) detect and locate the monitor marks in the sample loading device from the sample image taken by the imager using the said ML detection model from (3);
(5) generate a marker grid from the detected monitor marks in (4);
(6) calculate a homographic transform based on the generated monitor mark grid; and
(7) estimate the TLD, and determine the area, size, and concentration of the imaged analytes in the image-based assay.

The present invention can be further refined to perform region based TLD estimation and calibration to improve the accuracy of the image-based assay. An embodiment of such an approach comprises:
(1) Use a sample loading device in image-based assay, e.g. QMAX device, wherein there are monitor marks—not submerged in the sample and residing in the device that can be imaged from the top by an imager in the image-based assay;
(2) take an image of the sample in the sample holding device including analytes and monitor marks;
(3) build and train a machine learning (ML) model for detecting the monitor marks in the sample holding device from the images taken by the imager;
(4) partition the image of the sample taken by the imager into non-overlapping regions;
(5) detect and locate monitor marks from the sample image taken by the imager using the ML model of (3);
(6) generate a region-based mark grid for each of the region with more than 5 non-colinear monitor marks detected in the local region;
(7) generate a mark grid for all regions not in (6) based on detected monitor marks from the image of the sample taken by the imager;
(8) calculate a region-specific homographic transform for each region in (6) based on its own region-based mark grid generated in (6);
(9) calculate a homographic transform for all other regions based on the mark grid generated in (7);
(10) estimate the region based TLD for each region in (6) based on the region based homographic transform generated in (8);
(11) estimate the TLD for other regions based on the homographic transform from (9); and
(12) apply the estimated TLDs from (10) and (12) to determine the area and concentration of the imaged analytes in each partition in the image-based assay.

In some embodiments, the monitoring mark has a sharp edge and a flat surface.

In some embodiments, the monitoring mark is used to determine the local properties of an image and/or local operating conditions (e.g. gap size, plate qualities)

In some embodiments, the monitoring mark has the same shape as the spacers.

Monitoring Assay Operation Using Monitoring Marks

One aspect of the present invention is that for assaying with a QMAX card that have two moveable plates, monitoring marks placed inside a thin sample can be used to monitor the operating conditions for the QMAX card. The operating conditions can include whether the sample is loaded properly, whether the two plates are closed properly, whether the gap between the two plates is the same or approximately the same as a predetermined value.

In some embodiments, for a QMAX card that comprise two movable plates and has, in a closed configuration, a predetermined gap between the two plates, the operating conditions of the QMAX assay is monitored by taking the images of the monitoring mark in a closed configuration. For example, if the two plates are not closed properly, the monitoring marks will appear differently in an image than if the two plates are closed properly. A monitoring mark surrounded by a sample will have a different appearance than a monitoring mark not surrounded by the sample. Hence, it can provide information on the sample loading conditions.

Z-1.1 A device for using a monitoring mark to monitor an operating condition of the device, the device comprising:
a first plate, a second plate, spacers, and one or more monitoring marks, wherein:
  i. the first plate and the second plate are movable relative to each other into different configurations;
  ii. each of the first plate and the second plate comprises an inner surface comprising a sample contact area for contacting a sample being analyzed;
  iii. one or both of the first plate and the second plate comprises the spacers that are permanently fixed on the inner surface of a respective plate,
  iv. the monitoring mark has at least one of its dimensions that (a) is predetermined and known, and (b) is observable by an imager;
  v. the monitoring mark is a microstructure that has at least one lateral linear dimension of 300 um or less; and
  vi. the monitoring mark is inside the sample;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and
wherein, after a force is used in making the two plates reach a close configuration, the monitoring mark is imaged to determine (i) whether the two plates have reached the intended closed configuration thereby regulating the sample thickness to be approximately a predetermined thickness, and/or (ii) to determine whether a sample has been loaded as desired.

In some embodiments, the image of the monitoring mark is used to determine whether the two plates have reached the intended closed configuration, wherein the sample is regulated to have a thickness of approximately a predetermined thickness.

In some embodiments, the image of the monitoring mark is used to determine whether a sample has been loaded as desired.

In some embodiments, the monitoring mark is imaged to determine whether the two plates have reached the intended closed configuration wherein the sample thickness is regulated to be a predetermined thickness, and to determine whether a sample has been loaded as desired.

In some embodiments, the spacers serve as the monitoring marks.

In some embodiments, the system comprises the device and a computational device and a non-transitory computer readable medium having instructions that, when executed, it perform the determination.

In some embodiments, a non-transitory computer readable medium having instructions that, when executed, perform a method comprising using one or more images of a thin sample layer together with monitoring marks to determine (i) whether the two plates have reached the intended closed configuration thereby regulating the sample thickness to be approximately a predetermined thickness, or (ii) whether a sample has been loaded as desired.

In some embodiments, the system comprises a non-transitory computer readable medium having instructions that, when executed, perform any method of the present disclosure.

W-1. A method for using a monitoring mark to monitor an operating condition of the device, the method comprising:
- (a) obtaining a device of any prior embodiment, wherein the device comprises two movable plates, spacers, and one or more monitoring marks where the monitoring marks are in the sample contact area;
- (b) obtaining an imager;
- (c) depositing a sample in the sample contact area of the device of (a), and forcing the two plates into a closed configuration;
- (d) taking, using the imager, one or more images of the thin sample layer together with the monitoring marks; and
- (e) using the image of the monitoring marks to determine (i) whether the two plates have reached the intended closed configuration thereby regulating the sample thickness to be approximately a predetermined thickness, or (ii) whether a sample has been loaded as desired.

In some embodiments, the image of the monitoring mark is used to determine whether the two plates have reached the intended closed configuration, wherein the sample is regulated to have a thickness of approximately a predetermined thickness.

In some embodiments, the image of the monitoring mark is used to determine whether a sample has been loaded as desired.

In some embodiments, the monitoring mark is imaged to determine whether the two plates have reached the intended closed configuration wherein the sample thickness is regulated to be a predetermined thickness, and to determine whether a sample has been loaded as desired.

In some embodiments, the system comprising the device and a computational device and a non-transitory computer readable medium having instructions that, when executed, it performs the determination.

Selecting Area of Interest and/or Removing Defect Image Area

In some embodiments, the sample has defects, a method of removing the effect of the defects to assay, comprising: identifying the defects in the image, taking the defect image our or selecting good area of the image that does not have the image caused by defects.

In some embodiments, the area of taking removed from the image is larger than the area of the defect image area.

In some embodiments, the thickness of the sample is configured to a thin thickness, so that the objects (e.g. cells) of interests forming a monolayer (i.e. there is no significant overlap between the object in the direction normal to the sample layer.

A method for determining a fabrication quality of a QMAX card using an imager, the method comprising:
- (f) obtaining a device of any prior embodiment, wherein the device comprises two movable plates, spacers, and one or more monitoring marks where the monitoring marks are in the sample contact area;
- (g) obtaining an imager;
- (h) depositing a sample in the sample contact area of the device of (a), and forcing the two plates into a closed configuration;
- (i) taking, using the imager, one or more images of the thin sample layer; and
- (j) using the image of the monitoring marks to determine a fabrication quality of the QMAX card.

A method for determining a fabrication quality of a QMAX card using an imager, the method comprising:
- (a) obtaining a device of any prior embodiment, wherein the device comprises two movable plates, spacers, and one or more monitoring marks where the monitoring marks are in the sample contact area;
- (b) obtaining an imager;
- (c) depositing a sample in the sample contact area of the device of (a), and forcing the two plates into a closed configuration;
- (d) taking, using the imager, one or more images of the thin sample layer together with the monitoring marks; and
- (e) using the image of the monitoring marks to determine a fabrication quality of the QMAX card.

The method of any prior embodiment, wherein determining the fabrication quality comprises measuring a characteristic (e.g., a length, width, pitch, webbing) of one or more monitoring marks, and comparing the measured characteristic with a reference value to determine a fabrication quality of the QMAX card.

The method of any prior embodiment, wherein determining the fabrication quality comprises measuring a first characteristic (e.g., an amount, a length, width, pitch, webbing) of one or more first monitoring marks, and comparing the measured first characteristic with a second characteristic (e.g., a number, a length, width, pitch, webbing) of one or more second monitoring marks to determine a fabrication quality of the QMAX card.

The method of any prior embodiments, wherein the determining is performed during use of the device of any prior embodiment to analyze a sample.

Another aspect of the present invention is to make the monitor marks have a periodic pattern in the sample holding device, such as in QMAX device, such that they occur periodically with a certain pitch in the image of the sample taken by an imager. Based on this periodic property, the monitor mark detection can become very reliable, since all monitor marks can be identified and derived from just few detected ones as they are positioned periodically in prespecified configuration, and moreover, such configuration can be made precise with nanofabrication technologies such as nanoimprint. And from there, both sample image based and image region based TLD estimation can become more accurate and robust, because of the periodic pattern of the monitor marks.

Some Examples

Single Plate

AA-1.1 A device for assaying a micro-feature in a thin sample using an imager, the device comprising:
- (a) a solid-phase surface comprising a sample contact area for contacting a thin sample having a thickness of 200 um or less, and comprising or is suspected to comprise a micro-feature; and
- (b) one or more marks, wherein the mark:
  - x. has a sharp edge that (i) has predetermined and known shape and dimension, and (ii) is observable by an imager that images the micro-feature;
  - xi. is a microstructure that at least one lateral linear dimension of 300 um or less; and
  - xii. is inside the sample;

wherein at least one of the marks is imaged by the imager during the assaying.

AA-1.2 A device for assaying a micro-feature in a thin sample using an imager, the device comprising:
- (a) a solid-phase surface comprising a sample contact area for contacting a thin sample having a thickness of 200 um or less, and comprises or is suspected to comprise a micro-feature; and
- (b) one or more marks, wherein the mark:
  - i. comprises either a protrusion or a trench from the solid-phase surface
  - ii. has a sharp edge that (i) has predetermined and known shape and dimension, and (ii) is observable by an imager that images the micro-feature;
  - iii. is a microstructure that at least one lateral linear dimension of 300 um or less; and
  - iv. is inside the sample;

wherein at least one of the marks is imaged by the imager during the assaying.

Two Plates with a Constant Spacing

AA-2.1 A device for assaying a micro-feature in a thin sample using an imager, the device comprising:
a first plate, a second plate, and one or more monitoring marks, wherein:
- xviii. each of the first plate and the second plate comprises an inner surface comprising a sample contact area for contacting a sample that comprises or is suspected to comprise a micro-feature;
- xix. at least a portion of the sample is confined by the first and second plates into a thin layer of substantial constant thickness that 200 um or less;
- xx. the monitoring mark has a sharp edge that (a) has predetermined and known shape and dimension, and (b) is observable by an imager that images the micro-feature;
- xxi. the monitoring mark is a microstructure that at least one lateral linear dimension of 300 um or less; and
- xxii. the monitoring mark is inside the sample;

wherein at least one of the marks is imaged by the imager during the assaying.

Two Movable Plates

AA-3 A device for assaying a micro-feature in a thin sample using an imager, the device comprising:
a first plate, a second plate, spacers, and one or more monitoring marks, wherein:
- vii. the first plate and the second plate are movable relative to each other into different configurations;
- viii. each of the first plate and the second plate comprises an inner surface comprising a sample contact area for contacting a sample that comprises or is suspected to comprise a micro-feature;
- ix. one or both of the first plate and the second plate comprises the spacers that are permanently fixed on the inner surface of a respective plate,
- x. the monitoring mark has a sharp edge that (a) has predetermined and known shape and dimension, and (b) is observable by an imager that images the micro-feature;
- xi. the monitoring mark is a microstructure that at least one lateral linear dimension of 300 um or less; and
- xii. the monitoring mark is inside the sample;

wherein at least one of the marks is imaged by the imager during the assaying.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein a monitoring mark is (i) a different structure from the spacers, or (ii) the same structure that is used as a spacer.

B. Image Taking Improvement Using Sample Holder Having Micro-Marks

BB-1. An apparatus for improving image-taking of a micro-feature in a sample, the apparatus comprising:
- (c) a device of any prior device embodiment; and
- (d) an imager being used in assaying a sample that comprises or is suspected to comprise a micro-feature;

wherein the imager takes images, wherein at least one image comprises both a portion of sample and the monitoring.

CB-2. A system for improving image-taking of a micro-feature in a sample, the system comprising:
- (d) a device of any prior device embodiment;
- (e) an imager being used in assaying a sample of comprises or is suspected to comprise a micro-feature; and
- (f) An algorithm that utilizes the mark as a parameter together with an imaging processing method to adjust the setting of the imager for the next image.

C. Imaging Analysis Using Sample Holder Having Micro-Marks

CC-1 An apparatus for improving analysis of an image of a micro-feature in a sample, the apparatus comprising:
- (a) a device of any prior device embodiment; and
- (b) a computation device being used in receiving an image of a mark and a sample that comprises or is suspected to comprise a micro-feature;

wherein the computation device runs an algorithm that utilizes the mark as a parameter together with an imaging processing method to improve the image quality in the image.

CC-2. A system for improving analysis of images of a micro-feature in a sample, the system comprising:
  (a) a device of any prior device embodiment;
  (b) an imager being used in assaying a sample of comprises or is suspected to comprise a micro-feature by taking one or multiple images of the sample and the mark; and
  (c) An algorithm that utilizes the mark as a parameter together with an imaging processing method to improve the image quality in at least one image taken in (c).

CC-3 A computer program product for assaying a micro-feature in a sample, the program comprising computer program code means applied and adapted for, in at least one image:
  (a) receiving an image of a sample and the monitoring mark(s), wherein the sample is loaded into device of any prior device claim, and wherein the image is taken by an imager; and
  (b) processing and analyzing the image to calculate the amount of the micro-feature, wherein the analyzing uses a detection model that is based on machine learning and the information provided by the image of the monitoring mark(s).

CC-4 A computing devices for assaying a micro-feature in a sample, the computation device comprising a computing devices that operate the algorithms in any of embodiments of the present invention.

CC-5 The method, device, computer program product, or system of any prior embodiment, wherein the improvement of the image quality comprises at least one selected from the group consisting of denoising, image normalization, image sharpening, image scaling, alignment (e.g., for face detection), super resolution, deblurring, and any combination of thereof.

CC-6 The method, device, computer program product, or system of any prior embodiment, wherein the imaging processing method comprises at least one selected from the group consisting of a histogram-based operation, a mathematics-based operation, a convolution-based operation, a smoothing operation, derivative-based operation, a morphology-based operation, shading correction, image enhancement and/or restoration, segmentation, feature extraction and/or matching, object detection and/or classification and/or localization, image understanding, and any combination of thereof.

CC-6.1 The method, device, computer program product, or system of any prior embodiment, wherein the histogram-based operation comprises at least one selected from the group consisting of contrast stretching, equalization, minimum filtering, median filtering, maximum filtering, and any combination thereof.

CC-6.2 The method, device, computer program product, or system of any prior embodiment, wherein the mathematics-based operation comprises at least one selected from the group consisting of binary operation (e.g., NOT, OR, AND, XOR, and SUB) arithmetic-based operations (e.g., ADD, SUB, MUL, DIV, LOG, EXP, SQRT, TRIG, and INVERT), and any combination thereof.

CC-6.3 The method, device, computer program product, or system of any prior embodiment, wherein the convolution-based operation comprises at least one selected from the group consisting of an operation in the spatial domain, Fourier transform, DCT, integer transform, an operation in the frequency domain, and any combination thereof.

CC-6.4 The method, device, computer program product, or system of any prior embodiment, wherein the smoothing operation comprises at least one selected from the group consisting of a linear filter, a uniform filter, a triangular filter, a Gaussian filter, a non-linear filter, a medial filter a kuwahara filter, and any combination thereof.

CC-6.5 The method, device, computer program product, or system of any prior embodiment, wherein the derivative-based operation comprises at least one selected from the group consisting of a first-derivative operation, a gradient filter, a basic derivative filter, a Prewitt gradient filters, a Sobel gradient filter, an alternative gradient filter, a Gaussian gradient filter, a second derivative filter, a basic second derivative filter, a frequency domain Laplacian, a Gaussian second derivative filter, an Alternative Laplacian filter, a Second-Derivative-in-the-Gradient-Direction (SDGD) filter, a third derivative filter, a higher derivative filter (e.g., a greater than third derivative filter), and any combination thereof.

CC-6.6 The method, device, computer program product, or system of any prior embodiment, wherein the morphology-based operation comprises at least one selected from the group consisting of dilation, erosion, Boolean convolution, opening and/or closing, hit-and-miss operation, contour, skeleton, propagation, gray-value morphological processing, Gray-level dilation, gray-level erosion, gray-level opening, gray-level closing, morphological smoothing, morphological gradient, morphological Laplacian, and any combination thereof.

CC-6.7 The method, device, computer program product, or system of any prior embodiment, wherein the image enhancement and/or restoration comprises at least one selected from the group consisting of sharpening, unsharpening, noise suppression, distortion suppression, and any combination thereof.

CC-6.8 The method, device, computer program product, or system of any prior embodiment, wherein the segmentation comprises at least one selected from the group consisting of thresholding, fixed thresholding, Histogram-derived thresholding, Isodata algorithm, background-symmetry algorithm, Triangle algorithm, Edge finding, Gradient-based procedure, zero-crossing based procedure, PLUS-based procedure, Binary mathematical morphology, salt-or-pepper filtering, Isolate objects with holes, filling holes in objects, removing border-touching objects, Exo-skeleton, Touching objects, Gray-value mathematical morphology, Top-hat transform, thresholding, Local contrast stretching, and any combination thereof.

CC-6.9 The method, device, computer program product, or system of any prior embodiment, wherein the feature extraction and/or matching comprises at least one selected from the group consisting of Independent component analysis, Isomap, Kernel Principal Component Analysis, Latent semantic analysis, Partial least squares, Principal component analysis, Multifactor dimensionality reduction, Nonlinear dimensionality reduction, Multilinear principal component Analysis, Multilinear subspace learning, Semidefinite embedding, Autoencoder, and any combination thereof.

A. Sample Holder Having Micro-Marks
Single Plate
AA-1.1 A device for assaying a micro-feature in a thin sample using an imager, the device comprising:
  (a) a solid-phase surface comprising a sample contact area for contacting a thin sample having a thickness of 200 um or less, and comprising or is suspected to comprise a micro-feature; and (b) one or more marks, wherein the mark:
  xiii. has a sharp edge that (i) has predetermined and known shape and dimension, and (ii) is observable by an imager that images the micro-feature;
  xiv. is a microstructure that at least one lateral linear dimension of 300 um or less; and
  xv. is inside the sample;
wherein at least one of the marks is imaged by the imager during the assaying.

AA-1.2 A device for assaying a micro-feature in a thin sample using an imager, the device comprising:
  (a) a solid-phase surface comprising a sample contact area for contacting a thin sample having a thickness of 200 um or less, and comprises or is suspected to comprise a micro-feature; and
  (b) one or more marks, wherein the mark:
    v. comprises either a protrusion or a trench from the solid-phase surface
    vi. has a sharp edge that (i) has predetermined and known shape and dimension, and (ii) is observable by an imager that images the micro-feature;
    vii. is a microstructure that at least one lateral linear dimension of 300 um or less; and
    viii. is inside the sample;
wherein at least one of the marks is imaged by the imager during the assaying.

Two Plates with a Constant Spacing

AA-2.1 A device for assaying a micro-feature in a thin sample using an imager, the device comprising:
  a first plate, a second plate, and one or more monitoring marks, wherein:
    xxiii. each of the first plate and the second plate comprises an inner surface comprising a sample contact area for contacting a sample that comprises or is suspected to comprise a micro-feature;
    xxiv. at least a portion of the sample is confined by the first and second plates into a thin layer of substantial constant thickness that 200 um or less;
    xxv. the monitoring mark has a sharp edge that (a) has predetermined and known shape and dimension, and (b) is observable by an imager that images the micro-feature;
    xxvi. the monitoring mark is a microstructure that at least one lateral linear dimension of 300 um or less; and
    xxvii. the monitoring mark is inside the sample;
wherein at least one of the marks is imaged by the imager during the assaying.

Two Movable Plates

AA-3 A device for assaying a micro-feature in a thin sample using an imager, the device comprising:
  a first plate, a second plate, spacers, and one or more monitoring marks, wherein:
    xiii. the first plate and the second plate are movable relative to each other into different configurations;
    xiv. each of the first plate and the second plate comprises an inner surface comprising a sample contact area for contacting a sample that comprises or is suspected to comprise a micro-feature;
    xv. one or both of the first plate and the second plate comprises the spacers that are permanently fixed on the inner surface of a respective plate,
    xvi. the monitoring mark has a sharp edge that (a) has predetermined and known shape and dimension, and (b) is observable by an imager that images the micro-feature;
    xvii. the monitoring mark is a microstructure that at least one lateral linear dimension of 300 um or less; and
    xviii. the monitoring mark is inside the sample;
wherein at least one of the marks is imaged by the imager during the assaying.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein a monitoring mark is (i) a different structure from the spacers, or (ii) the same structure that is used as a spacer.

B. Image Taking Improvement Using Sample Holder Having Micro-Marks

BB-1. An apparatus for improving image-taking of a micro-feature in a sample, the apparatus comprising:
  (e) a device of any prior device embodiment; and
  (f) an imager being used in assaying a sample that comprises or is suspected to comprise a micro-feature;
wherein the imager takes images, wherein at least one image comprises both a portion of sample and the monitoring.

CB-2. A system for improving image-taking of a micro-feature in a sample, the system comprising:
  (g) a device of any prior device embodiment;
  (h) an imager being used in assaying a sample of comprises or is suspected to comprise a micro-feature; and
  (i) a non-transitory computer readable medium having instructions that, when executed, utilize the mark as a parameter together with an imaging processing method to adjust the setting of the imager for the next image.

C. Imaging Analysis Using Sample Holder Having Micro-Marks

CC-1 An apparatus for improving analysis of an image of a micro-feature in a sample, the apparatus comprising:
  (c) a device of any prior device embodiment; and
  (d) a computation device being used in receiving an image of a mark and a sample that comprises or is suspected to comprise a micro-feature;
wherein the computation device runs an algorithm that utilizes the mark as a parameter together with an imaging processing method to improve the image quality in the image.

CC-2. A system for improving analysis of images of a micro-feature in a sample, the system comprising:
  (d) a device of any prior device embodiment;
  (e) an imager being used in assaying a sample of comprises or is suspected to comprise a micro-feature by taking one or multiple images of the sample and the mark; and
  (f) a non-transitory computer readable medium having instructions that, when executed, utilize the mark as a parameter together with an imaging processing method to improve the image quality in at least one image taken in (c).

CC-3 A computer program product for assaying a micro-feature in a sample, the program comprising computer program code means applied and adapted for, in at least one image:
(a) receiving an image of a sample and the monitoring mark(s), wherein the sample is loaded into device of any prior device claim, and wherein the image is taken by an imager; and
(b) processing and analyzing the image to calculate the amount of the micro-feature, wherein the analyzing uses a detection model that is based on machine learning and the information provided by the image of the monitoring mark(s).

CC-4 A computing devices for assaying a micro-feature in a sample, the computation device comprising a computing devices that operate the algorithms in any of embodiments of the present invention.

CC-5 The method, device, computer program product, or system of any prior embodiment, wherein the improvement of the image quality comprises at least one selected from the group consisting of denoising, image normalization, image sharpening, image scaling, alignment (e.g., for face detection), super resolution, deblurring, and any combination of thereof.

CC-6 The method, device, computer program product, or system of any prior embodiment, wherein the imaging processing method comprises at least one selected from the group consisting of a histogram-based operation, a mathematics-based operation, a convolution-based operation, a smoothing operation, derivative-based operation, a morphology-based operation, shading correction, image enhancement and/or restoration, segmentation, feature extraction and/or matching, object detection and/or classification and/or localization, image understanding, and any combination of thereof.

CC-6.1 The method, device, computer program product, or system of any prior embodiment, wherein the histogram-based operation comprises at least one selected from the group consisting of contrast stretching, equalization, minimum filtering, median filtering, maximum filtering, and any combination thereof.

CC-6.2 The method, device, computer program product, or system of any prior embodiment, wherein the mathematics-based operation comprises at least one selected from the group consisting of binary operation (e.g., NOT, OR, AND, XOR, and SUB) arithmetic-based operations (e.g., ADD, SUB, MUL, DIV, LOG, EXP, SQRT, TRIG, and INVERT), and any combination thereof.

CC-6.3 The method, device, computer program product, or system of any prior embodiment, wherein the convolution-based operation comprises at least one selected from the group consisting of an operation in the spatial domain, Fourier transform, DCT, integer transform, an operation in the frequency domain, and any combination thereof.

CC-6.4 The method, device, computer program product, or system of any prior embodiment, wherein the smoothing operation comprises at least one selected from the group consisting of a linear filter, a uniform filter, a triangular filter, a Gaussian filter, a non-linear filter, a medial filter a kuwahara filter, and any combination thereof.

CC-6.5 The method, device, computer program product, or system of any prior embodiment, wherein the derivative-based operation comprises at least one selected from the group consisting of a first-derivative operation, a gradient filter, a basic derivative filter, a Prewitt gradient filters, a Sobel gradient filter, an alternative gradient filter, a Gaussian gradient filter, a second derivative filter, a basic second derivative filter, a frequency domain Laplacian, a Gaussian second derivative filter, an Alternative Laplacian filter, a Second-Derivative-in-the-Gradient-Direction (SDGD) filter, a third derivative filter, a higher derivative filter (e.g., a greater than third derivative filter), and any combination thereof.

CC-6.6 The method, device, computer program product, or system of any prior embodiment, wherein the morphology-based operation comprises at least one selected from the group consisting of dilation, erosion, Boolean convolution, opening and/or closing, hit-and-miss operation, contour, skeleton, propagation, gray-value morphological processing, Gray-level dilation, gray-level erosion, gray-level opening, gray-level closing, morphological smoothing, morphological gradient, morphological Laplacian, and any combination thereof.

CC-6.7 The method, device, computer program product, or system of any prior embodiment, wherein the image enhancement and/or restoration comprises at least one selected from the group consisting of sharpening, unsharpening, noise suppression, distortion suppression, and any combination thereof.

CC-6.8 The method, device, computer program product, or system of any prior embodiment, wherein the segmentation comprises at least one selected from the group consisting of thresholding, fixed thresholding, Histogram-derived thresholding, Isodata algorithm, background-symmetry algorithm, Triangle algorithm, Edge finding, Gradient-based procedure, zero-crossing based procedure, PLUS-based procedure, Binary mathematical morphology, salt-or-pepper filtering, Isolate objects with holes, filling holes in objects, removing border-touching objects, Exo-skeleton, Touching objects, Gray-value mathematical morphology, Top-hat transform, thresholding, Local contrast stretching, and any combination thereof.

CC-6.9 The method, device, computer program product, or system of any prior embodiment, wherein the feature extraction and/or matching comprises at least one selected from the group consisting of Independent component analysis, Isomap, Kernel Principal Component Analysis, Latent semantic analysis, Partial least squares, Principal component analysis, Multifactor dimensionality reduction, Nonlinear dimensionality reduction, Multilinear principal component Analysis, Multilinear subspace learning, Semidefinite embedding, Autoencoder, and any combination thereof.

T1. A method for determining, from a distorted image, a true-lateral-dimension (TLD) of a sample on a sample holder, the method comprising:
(a) obtaining a device of any prior embodiment, wherein the device comprises one or more monitoring marks in the sample contact area;
(b) obtaining an imager, a computation hardware, and a non-transitory computer readable medium comprising an algorithm;
(c) depositing, in the sample contact area of the device of (a), a thin sample layer comprising a micro-feature;
(d) taking, using the imager, one or more images of the thin sample layer together with the monitoring marks, wherein the imager is positioned above the thin sample layer; and
(e) determining the true-lateral-dimension of the sample using the algorithm;

wherein
(i) the algorithm is a computer code that is executed on a computer system; and (ii) the algorithm uses an image of the monitoring marks as parameters.

T2. The method, device, computer program product, or system of any prior embodiment, wherein each monitoring mark comprises either a protrusion or a trench from the solid-phase surface.

T3. The method, device, computer program product, or system of any prior embodiment, wherein the microstructure does not have a sharp edge.

T4. The method, device, computer program product, or system of any prior embodiment, wherein the sample is selected from the group consisting of a biological sample, a chemical sample, and a sample that does not have a sharp edge.

T5. The method, device, computer program product, or system of any prior embodiment, wherein the monitoring mark is used as a parameter together with an imaging processing method in an algorithm that (i) adjusting the imagine, (ii) processing an image of the sample, (iii) determining a property related to the micro-feature, or (iv) any combination of the above.

T6. The method, device, computer program product, or system of any prior embodiment, wherein the spacers have a substantially uniform height that is equal to or less than 200 microns, and a fixed inter-spacer-distance (ISD);

AA. Method and Device for Improving an Imaging of a Thin Layer of Sample.

AA1. A method for improving an imaging of a thin layer of sample, the method comprising:
(f) obtaining a marked sample holder, wherein the sample comprises one or more monitoring marks in the sample contact area;
(g) obtaining an imager, a computation hardware, and a non-transitory computer readable medium comprising an algorithm;
(h) depositing, in the sample contact area of the device of (a), a thin sample layer comprising a micro-feature;
(i) taking, using the imager, one or more images of the thin sample layer together with the monitoring marks, wherein the imager is positioned above the thin sample layer; and
(j) determining the true-lateral-dimension of the sample using the algorithm;
wherein
(i) the algorithm is a computer code that is executed on a computer system; and
(ii) the algorithm uses an image of the monitoring marks as parameters.

A-1

T1. A method for determining, from a distorted image, a true-lateral-dimension (TLD) of a sample on a sample holder, the method comprising:
(k) obtaining a device of any prior embodiment, wherein the device comprises one or more monitoring marks in the sample contact area;
(l) obtaining an imager, a computation hardware, and a non-transitory computer readable medium comprising an algorithm;
(m) depositing, in the sample contact area of the device of (a), a thin sample layer comprising a micro-feature;
(n) taking, using the imager, one or more images of the thin sample layer together with the monitoring marks, wherein the imager is positioned above the thin sample layer; and
(o) determining the true-lateral-dimension of the sample using the algorithm;
wherein
(i) the algorithm is a computer code that is executed on a computer system; and
(ii) the algorithm uses an image of the monitoring marks as parameters.

14. A device for assaying a micro-feature in a sample using an imager, the device comprising:
(a) a solid-phase surface comprising a sample contact area for contacting a sample which comprises a micro-feature; and
(b) one or more monitoring marks, wherein the monitoring marks:
ix. are made of a different material from the sample;
x. are inside the sample during an assaying the microstructure, wherein the sample forms, on the sample contact area, a thin layer of a thickness less than 200 um;
xi. have their lateral linear dimension of about 1 um (micron) or larger, and
xii. have at least one lateral linear dimension of 300 um or less; and
wherein during the assaying at least one monitoring mark is imaged by the imager wherein used during assaying the analyte; and a geometric parameter (e.g. shape and size) of the monitoring mark, and/or a pitch between monitoring marks are (a) predetermined and known prior to assaying of the analyte, and (b) used as a parameter in an algorithm that determines a property related to the micro-feature.

N8. A device for assaying a micro-feature in a sample using an imager, the device comprising:
a solid-phase surface comprising a sample contact area for contacting a sample which comprises a micro-feature; and
one or more monitoring marks, wherein each monitoring mark comprises either a protrusion or a trench from the solid-phase surface, wherein:
xiii. the protrusion or the trench comprises a flat surface that is substantially parallel to a neighbor surface that is a portion of the solid-phase surface adjacent the protrusion or the trench;
xiv. a distance between the flat surface and the neighboring surface is about 200 micron (um) or less;
xv. the flat surface an area that has (a) a linear dimension is at least about 1 um or larger, and (b) at least one linear dimension 150 um or less;
xvi. the flat surface of at least one monitoring mark is imaged by an imager used during assaying the micro-feature; and
xvii. a shape of the flat surface, a dimension of the flat surface, a distance between the flat surface and the neighboring surface, and/or a pitch between monitoring marks are (a) predetermined and known prior to assaying of the micro-feature, and (b) used as a parameter in an algorithm that determines a property related to the micro-feature.

N9. A device for assaying a micro-feature in a sample using an imager, the device comprising:
a first plate, a second plate, spacers, and one or more monitoring marks, wherein:
xix. the first plate and the second plate are movable relative to each other into different configurations;
xx. each of the first plate and the second plate comprises an inner surface comprising a sample contact area for contacting a sample that comprises a micro-feature;

xxi. one or both of the first plate and the second plate comprises the spacers that are permanently fixed on the inner surface of a respective plate, xxii. the spacers have a substantially uniform height that is equal to or less than 200 microns, and a fixed inter-spacer-distance (ISD);

xxiii. the monitoring marks are made of a different material from the sample;

xxiv. the monitoring marks are inside the sample during an assaying the microstructure, wherein the sample forms, on the sample contact area, a thin layer of a thickness less than 200 um; and xxv. the monitoring marks have their lateral linear dimension of about 1 um (micron) or larger, and have at least one lateral linear dimension of 300 um or less;

wherein during the assaying at least one monitoring mark is imaged by the imager wherein used during assaying the micro-feature; and a shape of the flat surface, a dimension of the flat surface, a distance between the flat surface and the neighboring surface, and/or a pitch between monitoring marks are (a) predetermined and known prior to assaying of the micro-feature, and (b) used as a parameter in an algorithm that determines a property related to the micro-feature;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein a monitoring mark is (i) a different structure from the spacers, or (ii) the same structure that is used as a spacer.

N10. A device for assaying a micro-feature in a sample using an imager, the device comprising:
a first plate, a second plate, spacers, and one or more monitoring marks, wherein:
xxvi. the first plate and the second plate are movable relative to each other into different configurations;
xxvii. each of the first plate and the second plate comprises an inner surface comprising a sample contact area for contacting a sample that comprises a micro-feature;
xxviii. one or both of the first plate and the second plate comprises the spacers that are permanently fixed on the inner surface of a respective plate,
xxix. the spacers have a substantially uniform height that is equal to or less than 200 microns, and a fixed inter-spacer-distance (ISD);
xxx. each monitoring mark comprises either a protrusion or a trench on one or both of the sample contact areas;
xxxi. the protrusion or the trench comprises a flat surface that is substantially parallel to a neighbor surface that is a portion of the solid-phase surface adjacent the protrusion or the trench;
xxxii. a distance between the flat surface and the neighboring surface is about 200 micron (um) or less;
xxxiii. the flat surface an area that has (a) a linear dimension is at least about 1 um or larger, and (b) at least one linear dimension 150 um or less;
xxxiv. the flat surface of at least one monitoring mark is imaged by an imager used during assaying the micro-feature; and
xxxv. a shape of the flat surface, a dimension of the flat surface, a distance between the flat surface and the neighboring surface, and/or a pitch between monitoring marks are (a) predetermined and known prior to assaying the micro-feature, and (b) used as a parameter in an algorithm that determines a property related to the micro-feature.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration and the plates are forced to the closed configuration by applying the imprecise pressing force on the force area; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers; and wherein a monitoring mark is (i) a different structure from the spacers, or (ii) the same structure that is used as a spacer.

N12. A device for imaging based assay, comprising:
a device of any prior device embodiment, wherein the device has at least five monitoring marks wherein at least three of the monitoring marks are not aligned on a linear line.

N12. An apparatus for assaying a micro-feature in a sample using an imager, the system comprising:
(e) a device of any prior device embodiment; and
(f) an imager that is used in assaying a sample of comprising a micro-feature.

N14. A system for performing an imaging-based assay, the system comprising:
(d) a device of any prior device embodiment;
(e) an imager that is used in assaying a sample of comprising a micro-feature; and
(f) a non-transitory computer readable medium comprising instructions that, when executed, utilize the monitoring marks of the device to determine a property related to the micro-feature.

NN8. A system for assaying a micro-feature in a sample using an imager, the system comprising:
(j) a device of any prior device embodiment;
(k) an imager that is used in assaying a sample of comprising a micro-feature; and
(l) a non-transitory computer readable medium comprising instructions that, when executed, utilize monitoring marks of the device to assay a property related to the micro-feature, wherein the instructions comprise machine learning.

NN9. A method for assaying a micro-feature in a sample using an imager, comprising:
(d) obtaining a device, apparatus, or a system of any prior embodiment;
(e) obtaining a sample and depositing the sample on a sample contact area in the device, apparatus, or system in (a), wherein the sample comprises a micro-feature; and (f) assaying the micro-feature.
140. A method for assaying a micro-feature in a sample using an imager, comprising:
(d) obtaining a device, apparatus, or system of any prior embodiment;
(e) obtaining a sample and depositing the sample on a sample contact area in the device, apparatus, or system in (a), wherein the sample comprises a micro-feature;
(f) assaying the micro-feature, wherein the assaying comprise a step of using machine learning.
T1. A method for determining, from a distorted image, a true-lateral-dimension (TLD) of a sample on a sample holder, the method comprising:
(p) obtaining a device of any prior embodiment, wherein the device comprises one or more monitoring marks in the sample contact area;
(q) obtaining an imager, a computation hardware, and a non-transitory computer readable medium comprising an algorithm;
(r) depositing, in the sample contact area of the device of (a), a thin sample layer comprising a micro-feature;
(s) taking, using the imager, one or more images of the thin sample layer together with the monitoring marks, wherein the imager is positioned above the thin sample layer; and
(t) determining the true-lateral-dimension of the sample using the algorithm;
wherein
(i) the algorithm is a computer code that is executed on a computer system; and
(ii) the algorithm uses an image of the monitoring marks as parameters.
T2. A method for determining, from a distorted image, the true-lateral-dimension (TLD) of a sample on a sample holder, the method comprising:
(a) obtaining a device of any prior embodiment, wherein the device comprises the one or more monitoring marks in the sample contact area;
(b) obtaining an imager, a computation hardware, and a non-transitory computer readable medium comprising an algorithm;
(c) depositing, in the sample contact area of the device in (a), a thin sample layer comprising a micro-feature;
(d) taking, using the imager, one or more images of the thin sample layer together with the monitoring marks, wherein the imager is positioned above the thin sample layer; and
(e) determining the true-lateral-dimension and the coordinates of the imaged sample in real world by physical metrics (e.g. micrometers) using the algorithm;
wherein
(i) the algorithm is a computer code that is executed on a computer system; and
(ii) the algorithm uses an image of the monitoring marks as parameters.
T3. The device, method, or system of any prior embodiment, wherein micro-features from the sample and monitoring marks are disposed within the sample holding device.
T4. The device, method, or system of any prior embodiment, wherein the determining comprises detecting and locating the monitoring marks in the image of the sample taken by the imager.
T5. The device, method, or system of any prior embodiment, wherein the determining comprises generating a monitoring mark grid based on the monitoring marks detected from the image of the sample taken by the imager.

T6. The device, method, or system of any prior embodiment, wherein the determining comprises calculating a homographic transform from the generated monitoring mark grid.
T7. The device, method, or system of any prior embodiment, wherein the determining comprises estimating the TLD from the homographic transform, and determining the area, size, and concentration of the detected micro-features in the image-based assay.
T8. The method, device or system of any prior embodiment, wherein the TLD estimation is based on regions in a sample image taken by the imager, comprising:
(a) obtaining a sample;
(b) loading the sample into a sample holding device, e.g. QMAX device, wherein there are monitoring marks, wherein the monitoring marks are not submerged in the sample and reside in the device that can be imaged from the top by an imager in the image-based assay;
(c) taking an image of the sample in the sample loading device including micro-features and monitoring marks;
(d) detecting the monitoring marks in the sample image taken by the imager;
(e) partitioning the sample image into non-overlapping regions;
(f) generating a region-based mark grid for each of the non-overlapping regions with more than 5 non-colinear monitoring marks detected in the local region;
(g) generating a mark grid for all other regions not in (f) based on the monitoring marks detected from the sample image taken by the imager;
(h) calculating a region-specific homographic transform for each region in (f) based on its own region-based mark grid generated from (f);
(i) calculating a homographic transform for all other regions not in (f) based on the mark grid generated in (g);
(j) estimating the region-based TLD for each region in (f) based on the region-based homographic transform of (g);
(k) estimating the TLD for other regions not in (f) based on the homographic transform of (i); and
(l) applying the estimated TLDs from (j) and (k) to determine the area and concentration of the imaged micro-features in each image partition in the image-based assay.
T9. The method, device or system of any prior embodiment, wherein the monitoring marks in the sample holding device are distributed according to a periodic pattern with a defined pitch period.
T10. The method, device or system of any prior embodiment, wherein the said monitoring marks are detected and applied as detectable anchors for calibration and improving the measurement accuracy in the image-based assay.
T12. The method, device or system of any prior embodiment, wherein the detection of the monitoring marks in the sample image taken by the imager utilizes the periodicity of the monitoring mark distribution in the sample holding device for error correction and/or the reliability of the detection.
T12. The method, device or system of any prior embodiment, wherein the detection, identification, area and/or shape contour estimation of the said monitoring marks in image-based assay are through machine learning (ML) with ML based monitoring mark detection models and apparatus built or trained from the image taken by the imager on the said device in the image-based assay.

T14. The method, device or system of any prior embodiment, wherein the detection, identification, area and/or shape contour estimation of the said monitoring marks in image-based assay are through image processing or image processing combined with machine learning.

T14. The method, device or system of any prior embodiment, wherein the detected monitoring marks are applied to TLD estimation in the image-based assay to calibrate the system and/or improve the measurement accuracy in the imaged-based assay.

T15. The method, device or system of any prior embodiment, wherein the detected monitoring marks are applied and not limited to micro-feature size, volume and/or concentration estimation in image-based assay to calibrate the system and/or improve the measurement accuracy.

T16. The method, device or system of any prior embodiment, wherein the detection of the monitoring marks and/or TLD estimation are applied to the fault detection in image-based assay, including and not limited to detecting defects in the sample holding device, mis-placement of the sample holding device in the imager, and/or the focusing fault of the imager.

T17. The method, device or system of any prior embodiment, wherein the said monitoring marks are detected as anchors to apply in a system to estimate the area of an object in image-based assay, comprising:
  i. loading the sample to a sample holding device having monitoring marks residing in said device in image-based assay;
  ii. taking the image of the sample in the sample holding device including the micro-features and the monitoring marks; and
  iii. detecting the monitoring marks in the image of the sample taken by the imager on the sample holding device, determine the TLD and calculate the area estimation in the image-based assay to determine the size of the imaged object from pixels in the image to its physical size of micrometers in the real world.

T18. The method, device or system of any prior embodiment, wherein the system comprises:
  i. detecting the monitoring mark in a digital image;
  ii. generating a monitoring mark grid;
  iii. calculating the image transform based on the monitoring mark grid; and
  iv. estimating the area of the object in image of the sample and its physical size in the real world in image-based assay.

T19. The method, device or system of any prior embodiment, wherein the generated monitoring mark grid from the detected monitoring marks is used to calculate a homographic transform to estimate TLD, the area of the object in the image of the sample taken by the imager, and the physical size of the object in the real world.

T20. The method, device or system of any prior embodiment, wherein the method comprises:
  i. partitioning the image of the sample taken by the imager in image-based assay into nonoverlapping regions;
  ii. detecting and local monitoring marks in the image;
  iii. generating a region-based mark grid for that region if more than 5 non-colinear monitoring marks are detected in the region;
  iv. generating a mark grid for all other regions based on the monitoring marks detected in the image of the sample taken by the imager;
  v. calculating a region-based homographic transform from the generated region-based mark grid for each region in (iii);
  vi. calculating a homographic transform for all other regions not in (iii) based on the mark grid generated in (iv); and
  vii. estimating the TLDs for each region based on the homographic transforms generated from (v) and (vi), determine the area of the objects in the image of the sample at each region and their size in the real world in the image-based assay.

T21. The method, device or system of any prior embodiment, wherein the assay is a medical, a diagnostic, a chemical or a biological test.

T22. The method, device or system of any prior embodiment, wherein said micro-feature is a cell.

T23. The method, device or system of any prior embodiment, wherein said micro-features is a blood cells.

T24. The method, device or system of any prior embodiment, wherein said micro-feature is a protein, peptide, DNA, RNA, nucleic acid, small molecule, cell, or nanoparticle.

T25. The method, device or system of any prior embodiment, wherein said micro-feature comprises a label.

T26. The method, device or system of any prior embodiment, wherein said algorithm comprises a computer program product comprising computer program code means adapted for, in at least one image:
  (a) receiving an image of a sample, wherein the sample is loaded into a QMAX device and the image is taken by an imager connected to the QMAX device, wherein the image includes both the sample and monitoring marks;
  (b) analyzing the image with a detection model and generating a 2-D data array of the image, wherein the 2-D data array includes probability data of the micro-feature for each location in the image, and the detection model is established through a training process that comprises:
    i. feeding an annotated data set to a convolutional neural network, wherein the annotated data set is from samples that are the same type as the test sample and for the same micro-feature; and
    ii. training and establishing the detection model by convolution; and
  (c) analyzing the 2-D data array to detect local signal peaks with:
    i. signal list process, or
    ii. local searching process; and
  (d) calculating the amount of the micro-feature based on local signal peak information.

T27. The method, device or system of any prior embodiment, wherein said algorithm comprises a computer program product comprising computer program code means applied and adapted for, in at least one image:
  (a) representing a pattern of inference between an object in the sample and a pixel contour map of the said object in the image of the sample taken by the imager on the sample holding device,
  (b) numerically reconstructing an image of at least one object detected from the inference pattern in the image of the sample and generate the contour masks enclosing the object identified by inference module where the object is in focus,
  (c) identifying at least one portion of the image of the sample for at least one object in the selected portion of the image of the sample, and (d) calculating, from said at least one portion, at least one feature of the object to identify the objects in the selected portion of the image of the sample taken by the imager, (e) calculating, from the selected portion of the image of the sample, the count of the detected objects in the selected portion and its concentration, when said program is run on a computing device, or in a computing Cloud by means of network connection.

T28. The method, device or system of any prior embodiment, wherein said algorithm comprises a computer program product comprising computer program code means adapted for, in at least one image:

(a) receiving an image of a sample, wherein the sample is loaded into a QMAX device and the image is taken by an imager connected to the QMAX device, wherein the image includes both the sample and monitoring marks; and (b) analyzing the image to calculate the amount of the micro-feature, wherein the analyzing uses a detection model that is based on machine learning and the information provided by the image of the monitoring marks.

The method, device or system of any prior embodiment further comprises computer readable storage medium or memory storage unit comprising a computer program of any prior embodiment.

The method, device or system of any prior embodiment further comprises a computing arrangement or mobile apparatus comprising the calculation device of any prior embodiment.

The method, device or system of any prior embodiment further comprises a computing arrangement or mobile apparatus comprising the computer program product of any prior embodiment.

The method, device or system of any prior embodiment further comprises a computing arrangement or mobile apparatus comprising the computer readable storage medium or storage unit of any prior embodiment.

A device for analyzing a sample comprising:
a first plate, a second plate, a surface amplification layer, and a capture agent, wherein
(a) the first and second plats are movable relative to each other into different configurations, and have, on its respective surface, a sample contact area for contacting a sample that comprises a target analyte,
(b) the surface amplification layer is on one of the sample contact areas, (c) the capture agent is immobilized on the surface amplification layer, wherein the capture agent specifically binds the target analyte, wherein the surface amplification layer amplifies an optical signal from the target analyte or a label attached to the target analyte when they are is in proximity of the surface amplification layer much stronger than that when they are micron or more away, wherein one of the configurations is an open configuration, in which the average spacing between the inner surfaces of the two plates is at least 200 um; and wherein another of the configurations is a close configuration, in which, at least part of the sample is between the two plates and the average spacing between the inner surfaces of the plates is less than 200 um.

A device for analyzing a sample comprising:
a first plate, a second plate, a surface amplification layer, and a capture agent, wherein
(d) the first and second plats are movable relative to each other into different configurations, and have, on its respective surface, a sample contact area for contacting a sample that comprises a target analyte,
(e) the surface amplification layer is on one of the sample contact areas,
(f) the capture agent is immobilized on the surface amplification layer, wherein the capture agent specifically binds the target analyte, wherein the surface amplification layer amplifies an optical signal from a label attached to the target analyte when it is in proximity of the surface amplification layer much stronger than that when it is micron or more away, wherein one of the configurations is an open configuration, in which the average spacing between the inner surfaces of the two plates is at least 200 um;

wherein another of the configurations is a close configuration, in which, at least part of the sample is between the two plates and the average spacing between the inner surfaces of the plates is less than 200 um;

wherein the thickness of the sample in the closed configuration, the concentration of the labels dissolved in the sample in the closed configuration, and the amplification factor of the surface amplification layer are configured such that any the labels that are bound directly or indirectly to the capture agents are visible in the closed configuration without washing away of the unbound labels.

An apparatus comprising a device of any prior embodiment and a reader for reading the device.

A homogeneous assay method using a device of any prior embodiment, wherein the thickness of the sample in a closed configuration, the concentration of labels, and amplification factor of the amplification surface are configured to make the label(s) bound on the amplification surface visible without washing away of the unbound labels.

The method of any prior embodiment, wherein the method is performed by:
obtaining a device of any of any prior embodiment
depositing a sample on one or both of the plates when the plates are in an open configuration;
closing the plates to the closed configuration; and
reading the sample contact area with a reading device to produce an image of signals.

The device or method of any prior embodiment, wherein the labels bound to the amplification surface are visible in less than 60 seconds.

The device or method of any prior embodiment, wherein the method is a homogeneous assay in which the signal is read without using a wash step to remove any biological materials or labels that are not bound to the amplification surface.

The device or method of any prior embodiment, wherein the labels bound to the amplification surface are read by a pixelated reading method.

The device or method of any prior embodiment, wherein the labels bound to the amplification surface are read by a lump-sum reading method.

The device or method of any prior embodiment, wherein the assay has a detection sensitivity of 0.1 nM or less.

The device or method of any prior embodiment, wherein the method biological materials or labels that are not bound to the amplification surface are removed by a sponge prior to reading.

The device or method of any prior embodiment, wherein the signal amplification layer comprises a D2PA.

The device or method of any prior embodiment, wherein the signal amplification layer comprises a layer of metallic material.

The device or method of any prior embodiment, wherein the signal amplification layer comprises a continuous metallic film that is made of a material selected from the group consisting of gold, silver, copper, aluminum, alloys thereof, and combinations thereof.

The device or method of any prior embodiment, wherein the different metals layers either locally enhance or act as a reflector, or both, to enhance an optical signal.

The device or method of any prior embodiment, wherein the signal amplification layer comprises a layer of metallic material and a dielectric material on top of the metallic material layer, wherein the capture agent is on the dielectric material.

The device or method of any prior embodiment, wherein the metallic material layer is a uniform metallic layer, nanostructured metallic layer, or a combination.

The device or method of any prior embodiment, wherein the amplifies signals by plasmonic enhancement.

The device or method of any prior embodiment, wherein assay comprises detecting the labels by Raman scattering.

The device or method of any prior embodiment, wherein the capture agent is an antibody.

The device or method of any prior embodiment, wherein the capture agent is a polynucleotide.

The device or method of any prior embodiment, wherein the device further comprise spacers fixed on one of the plate, wherein the spacers regulate the spacing between the first plate and the second plate in the closed configuration.

The device or method of any prior embodiment, wherein the amplification factor of the surface amplification layer is adjusted to make the optical signal from a single label that is bound directly or indirectly to the capture agents visible.

The device or method of any prior embodiment, wherein the amplification factor of the surface amplification layer is adjusted to make the optical signal from a single label that is bound directly or indirectly to the capture agents visible, wherein the visible single labels bound to the capture agents are counted individually.

The device or method of any prior embodiment, wherein the spacing between the first plate and the second plate in the closed configuration is configured to make saturation binding time of the target analyte to the capture agents 300 sec or less.

The device or method of any prior embodiment, wherein the spacing between the first plate and the second plate in the closed configuration is configured to make saturation binding time of the target analyte to the capture agents 60 sec or less.

The device or method of any prior embodiment, wherein the amplification factor of the surface amplification layer is adjusted to make the optical signal from a single label visible.

The device or method of any prior embodiment, wherein the capture agent is a nucleic acid.

The device or method of any prior embodiment, wherein the capture agent is a protein.

The device or method of any prior embodiment, wherein the capture agent is an antibody.

The device or method of any prior embodiment, wherein the sample contact area of the second plate has a reagent storage site, and the storage site is approximately above the binding site on the first plate in the closed configuration.

The device or method of any prior embodiment, wherein the reagent storage site comprises a detection agent that binds to the target analyte.

The device or method of any prior embodiment, wherein the detection agent comprises the label.

The device or method of any prior embodiment, wherein the capture agent and detection agent both bind to the target analyte to form a sandwich that comprises the label.

The device or method of any prior embodiment, wherein the signal amplification layer comprises a layer of metallic material.

The device or method of any prior embodiment, wherein the signal amplification layer comprises a layer of metallic material and a dielectric material on top of the metallic material layer, wherein the capture agent is on the dielectric material.

The device or method of any prior embodiment, wherein the metallic material layer is a uniform metallic layer, nanostructured metallic layer, or a combination.

The device or method of any prior embodiment, wherein the amplification layer comprises a layer of metallic material and a dielectric material on top of the metallic material layer, wherein the capture agent is on the dielectric material, and the dielectric material layer has a thickness of 0.5 nm, 1 nm, 5 nm, 10 nm, 20 nm, 50 nm, 00 nm, 200 nm, 500 nm, 1000 nm, 2 um, 3 um, 5 um, 10 urn, 20 urn, 30 um, 50 urn, 100 urn, 200 urn, 500 urn, or in a range of any two values.

The device or method of any prior embodiment, wherein the method further comprises quantifying a signal in an area of the image to providing an estimate of the amount of one or more analytes in the sample.

The device or method of any prior embodiment, wherein the method comprises identifying and counting individual binding events between an analyte with the capture agent in an area of the image, thereby providing an estimate of the amount of one or more analytes in the sample.

The device or method of any prior embodiment, wherein the identifying and counting steps comprise: (1) determining the local intensity of background signal, (2) determining local signal intensity for one label, two labels, three labels, and four or more labels; and (3) determining the total number of labels in the imaged area.

The device or method of any prior embodiment, wherein the identifying and counting steps comprises: (1) determining the local spectrum of background signal, (2) determining local signal spectrum for one label, two labels, three labels, and four or more labels; and (3) determining the total number of labels in the imaged area.

The device or method of any prior embodiment, wherein the identifying and counting steps comprise: (1) determining the local Raman signature of background signal, (2) determining local signal Raman signature for one label, two labels, three labels, and four or more labels; and (3) determining the total number of labels in the imaged area.

The device or method of any prior embodiment, wherein the identifying and counting step comprises determining one or more of the local intensity, spectrum, and Raman signatures.

The device or method of any prior embodiment, wherein the method comprises quantifying a lump-sum signal in an area of the image, thereby providing an estimate of the amount of one or more analytes in the sample.

The device or method of any prior embodiment, wherein the sample contact area of the second plate has a reagent storage site, and the storage site is, in a closed configuration, approximately above the binding site on the first plate.

The device or method of any prior embodiment, wherein the method further comprises a step of labeling the target analyte with a detection agent.

The device or method of any prior embodiment, wherein the detection agent comprises a label.

The device or method of any prior embodiment, wherein the capture agent and detection agent both bind to the target analyte to form a sandwich.

The device or method of any prior embodiment, wherein the method further comprises measuring the volume of the sample in the area imaged by the reading device.

The device or method of any prior embodiment, wherein the target analyte is a protein, peptide, DNA, RNA, nucleic acid, small molecule, cell, or nanoparticle.

The device or method of any prior embodiment, wherein the image shows the position, local intensity, and local spectrum of the signals.

The device or method of any prior embodiment, wherein the signals are luminescence signals selected from the group consisting of fluorescence, electroluminescence, chemiluminescence, and electrochemiluminescence signals.

The device or method of any prior embodiment, wherein the signals are Raman scattering signals.

The device or method of any prior embodiment, wherein the signals are the forces due to local electrical, local mechanical, local biological, or local optical interaction between the plate and the reading device.

The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The method or device of any prior embodiment, wherein the fourth power of the inter-spacer-distance (ISD) divided by the thickness (h) and the Young's modulus (E) of the flexible plate ($ISD^4/(hE)$) is $5 \times 10^5$ um$^3$/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The method or device of any prior embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the analytes is proteins, peptides, nucleic acids, synthetic compounds, or inorganic compounds.

The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior embodiment, wherein the spacers have a shape of pillars and a ratio of the width to the height of the pillar is equal or larger than one.

The method or device of any prior embodiment, wherein the sample that is deposited on one or both of the plates has an unknown volume.

The method or device of any prior embodiment, wherein the spacers have a shape of pillar, and the pillar has substantially uniform cross-section.

The method or device of any prior embodiment, wherein the samples is for the detection, purification and quantification of chemical compounds or biomolecules that correlates with the stage of certain diseases.

The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

The method or device of any prior embodiment, wherein the samples is related to the detection, purification and quantification of microorganism.

The method or device of any prior embodiment, wherein the samples is related to virus, fungus and bacteria from environment, e.g., water, soil, or biological samples.

The method or device of any prior embodiment, wherein the samples is related to the detection, quantification of chemical compounds or biological samples that pose hazard to food safety or national security, e.g. toxic waste, anthrax.

The method or device of any prior embodiment, wherein the samples is related to quantification of vital parameters in medical or physiological monitor.

The method or device of any prior embodiment, wherein the samples is related to glucose, blood, oxygen level, total blood count.

The method or device of any prior embodiment, wherein the samples is related to the detection and quantification of specific DNA or RNA from biosamples.

The method or device of any prior embodiment, wherein the samples is related to the sequencing and comparing of genetic sequences in DNA in the chromosomes and mitochondria for genome analysis.

The method or device of any prior embodiment, wherein the samples is related to detect reaction products, e.g., during synthesis or purification of pharmaceuticals.

The method or device of any prior embodiment, wherein the samples is cells, tissues, bodily fluids, and stool.

The method or device of any prior embodiment, wherein the sample is the sample in the fields of human, veterinary, agriculture, foods, environments, and drug testing.

The method or device of any prior embodiment, wherein the sample is a biological sample is selected from hair, finger nail, ear wax, breath, connective tissue, muscle tissue, nervous tissue, epithelial tissue, cartilage, cancerous sample, or bone.

The method or device of any prior embodiment, wherein the inter-spacer distance is in the range of 5 um to 120 um.

The method or device of any prior embodiment, wherein the inter-spacer distance is in the range of 120 um to 200 um.

The method or device of any prior embodiment, wherein the flexible plates have a thickness in the range of 20 um to 250 um and Young's modulus in the range 0.1 to 5 GPa.

The method or device of any prior embodiment, wherein for a flexible plate, the thickness of the flexible plate times the Young's modulus of the flexible plate is in the range 60 to 750 GPa-um.

The method or device of any prior embodiment, wherein the layer of uniform thickness sample is uniform over a lateral area that is at least 1 mm$^2$.

The method or device of any prior embodiment, wherein the layer of uniform thickness sample is uniform over a lateral area that is at least 3 mm$^2$.

The method or device of any prior embodiment, wherein the layer of uniform thickness sample is uniform over a lateral area that is at least 5 mm$^2$.

The method or device of any prior embodiment, wherein the layer of uniform thickness sample is uniform over a lateral area that is at least 10 mm$^2$.

The method or device of any prior embodiment, wherein the layer of uniform thickness sample is uniform over a lateral area that is at least 20 mm$^2$.

The method or device of any prior embodiment, wherein the layer of uniform thickness sample is uniform over a lateral area that is in a range of 20 mm$^2$ to 100 mm$^2$.

The method or device of any prior embodiment, wherein the layer of uniform thickness sample has a thickness uniformity of up to +/−5% or better.

The method or device of any prior embodiment, wherein the layer of uniform thickness sample has a thickness uniformity of up to +/−10% or better.

The method or device of any prior embodiment, wherein the layer of uniform thickness sample has a thickness uniformity of up to +/−20% or better.

The method or device of any prior embodiment, wherein the layer of uniform thickness sample has a thickness uniformity of up to +/−30% or better.

The method, device, computer program product, or system of any prior embodiment having five or more monitoring marks, wherein at least three of the monitoring marks are not in a straight line.

The method, device, computer program product, or system of any prior embodiment, wherein each of the plates comprises, on its respective outer surface, a force area for applying an imprecise pressing force that forces the plates together;

The method, device, computer program product, or system of any prior embodiment, wherein one or both plates are flexible;

The method, device, computer program product, or system of any prior embodiment, wherein the fourth power of the inter-spacer-distance (IDS) divided by the thickness (h) and the Young's modulus (E) of the flexible plate (ISD4/(hE)) is 5×106 um3/GPa or less;

The method, device, computer program product, or system of any prior embodiment, wherein at least one of the spacers is inside the sample contact area;

The method, device, computer program product, or system of any prior embodiment, wherein fat specification of analyte The method, device, computer program product, or system of any prior embodiment, wherein fat specification of algorithms The method, device, computer program product, or system of any prior embodiment, wherein fat specification of impression force and press by hands.

The device, system, or method of any prior embodiment, wherein the algorithm is stored on a non-transitory computer-readable medium, and wherein the algorithm comprises instructions that, when executed, perform a method that utilizes monitoring marks of the device to determine a property corresponding to the analyte.

Some Examples of Marks

In the present invention, in some embodiments, the marks have the same shapes as the spacers.

In some embodiments, the marks is periodic or aperiodic.

In some embodiments, the distance between two marks are predetermined and known, but the absolution coordinates on a plate are unknown.

In some embodiments, the marks have predetermined and know shapes.

In some embodiments, the marks is configured to have a distribution in a plate, so that regardless the position of the plate, there are always the marks in the field of the view of the imaging optics.

In some embodiments, the marks is configured to have a distribution in a plate, so that regardless the position of the plate, there are always the marks in the field of the view of the imaging optics and that the number of the marks are sufficient to for local optical information.

In some embodiments, the marks are used to control the optical properties of a local area of the sample, whereas the area size is 1 um"2, 5 um"2, 10 um"2, 20 um"2, 50 um"2, 100 um"2, 200 um"2, 500 um"2, 1000 um"2, 2000 um"2, 5000 um"2, 10000 um"2, 100000 um"2, 500000 um"2, or a range between any of two values.

Use of "Limited Imaging Optics"

In the present invention, in some embodiments, the optical system for imaging the assay have "limited imaging optics". Some embodiments of limited imaging optics include, but not limited to:

1. The limited imaging optics system, comprising:
   imaging lenses;
   an imaging sensor;
   wherein the imaging sensor is a part of the camera of a smartphone;
   wherein at least one of the imaging lenses is a part of the camera of smartphone;

2. The limited imaging optics system of any prior embodiment, wherein: the optical resolution by physics is worse than 1 um, 2 um, 3 um, 5 um, 10 um, 50 um, or in a range between any of the two values.

3. The limited imaging optics system of any prior embodiment, wherein: the optical resolution per physics is worse than 1 um, 2 um, 3 um, 5 um, 10 um, 50 um, or in a range between any of the two values.

4. The limited imaging optics system of any prior embodiment, wherein: the preferred optical resolution per physics is between 1 um and 3 um;

5. The limited imaging optics system of any prior embodiment, wherein: the numerical aperture is less than 0.1, 0.15, 0.2, 0.2, 0.25, 0.3, 0.35, 0.4, 0.45, 0.5, or in a range between any of the two values.

6. The limited imaging optics system of any prior embodiment, wherein: the preferred numerical aperture is between 0.2 and 0.25.

7. The limited imaging optics system of any prior embodiment, wherein: the working distance is 0.2 mm, 0.5 mm, 1 mm, 2 mm, 5 mm, 10 mm, 20 mm, or in a range between any of the two values.

8. The limited imaging optics system of any prior embodiment, wherein: the working distance is 0.2 mm, 0.5 mm, 1 mm, 2 mm, 5 mm, 10 mm, 20 mm, or in a range between any of the two values.
9. The limited imaging optics system of any prior embodiment, wherein: the preferred working distance is between 0.5 mm to 1 mm.
10. The limited imaging optics system of any prior embodiment, wherein: the focal depth is 100 nm, 500 nm, 1 um, 2 um, 10 um, 100 um, 1 mm, or in a range between any of the two values.
11. The limited imaging optics system of any prior embodiment, wherein: the focal depth is 100 nm, 500 nm, 1 um, 2 um, 10 um, 100 um, 1 mm, or in a range between any of the two values.
12. The limited imaging optics system of any prior embodiment, wherein: the image sensor is a part of the smartphone camera module.
13. The limited imaging optics system of any prior embodiment, wherein: the diagonal length of the image sensor is less than 1 inch, ½ inch, ⅓ inch, ¼ inch, or in a range between any of the two values;
14. The limited imaging optics system of any prior embodiment, wherein: the imaging lenses comprises at least two lenses, and one lens is a part of the camera module of a smartphone.
15. The limited imaging optics system of any prior embodiment, wherein: at least one external lens is paired with the internal lens of smartphone.
16. The limited imaging optics system of any prior embodiment, wherein: the optical axis of external lens is aligned with the with the internal lens of smartphone, the alignment tolerance is less than 0.1 mm, 0.2 mm, 0.5 mm, 1 mm, or in a range between any of the two values.
17. The limited imaging optics system of any prior embodiment, wherein: the height of the external lens is less than 2 mm, 5 mm, 10 mm, 15 mm, 20 m, or in a range between any of the two values.
18. The limited imaging optics system of any prior embodiment, wherein: the preferred height of the external lens is between 3 mm to 8 mm.
19. The limited imaging optics system of any prior embodiment, wherein: the preferred height of the external lens is between 3 mm to 8 mm.
20. The limited imaging optics system of any prior embodiment, wherein: the diameter of the external lens is less than 2 mm, 4 mm, 8 mm, 10 mm, 15 mm, 20 mm, or in a range between any of the two values.
21. The limited imaging optics system of any prior embodiment, wherein: the optical magnification per physics is less than 0.1×, 0.5×, 1×, 2×, 4×, 5×, 10×, or in a range between any of the two values.
22. The limited imaging optics system of any prior embodiment, wherein: the preferred optical magnification per physics is less than 0.1×, 0.5×, 1×, 2×, 4×, 5×, 10×, or in a range between any of the two values.

The term "image-based assay" refers to an assay procedure that utilizes the image of the sample taken by an imager, where the sample can be and not limited to medical, biological and chemical sample.

The term "imager" refers to any device that can take image of the objects. It includes and not limited to cameras in the microscope, smartphone, or special device that can take image at various wavelength.

The term "sample feature" refers to some property of the sample that represents a potentially interesting condition. In certain embodiments, a sample feature is a feature that appears in an image of a sample and can be segmented and classified by a machine learning model. Examples of sample features include and not limited to analyte types in the sample, e.g. red blood cells, white blood cells, and tumor cells, and it includes analyte count, size, volume, concentration and the like.

The term "machine learning" refers to algorithms, systems and apparatus in the field of artificial intelligence that often use statistical techniques and artificial neural network to give computer the ability to "learn" (i.e., progressively improve performance on a specific task) from data without being explicitly programmed.

The term "artificial neural network" refers to a layered connectionist system inspired by the biological networks that can "learn" to perform tasks by considering examples, generally without being programmed with any task-specific rules.

The term "convolutional neural network" refers to a class of multilayer feed-forward artificial neural networks most commonly applied to analyzing visual images.

The term "deep learning" refers to a broad class of machine learning methods in artificial intelligence (AI) that learn from data with some deep network structures.

The term "machine learning model" refers to a trained computational model that is built from a training process in the machine learning from the data. The trained machine learning model is applied during the inference stage by the computer that gives computer the capability to perform certain tasks (e.g. detect and classify the objects) on its own. Examples of machine learning models include ResNet, DenseNet, etc. which are also named as "deep learning models" because of the layered depth in their network structure.

The term "image segmentation" refers to an image analysis process that partitions a digital image into multiple segments (sets of pixels, often with a set of bit-map masks that cover the image segments enclosed by their segment boundary contours). Image segmentation can be achieved through the image segmentation algorithms in image processing, such as watershed, grabcuts, mean-shift, etc., and through machine learning algorithms, such as MaskRCNN, etc.

The term "defects in the sample" refers to the artifacts that should not exist in an ideal sample condition or should not be considered in the features of the sample. They can come from and not limited to pollutants, e.g. dusts, air bobbles, etc., and from the peripheral objects in the sample, e.g. monitor marks (such as pillars) in the sample holding device. Defects can be of significant size and take significant amount of volume in the sample, e.g. air bubbles. They can be of different shape, in addition to their distribution and amounts in the sample—which are sample dependent.

The term "threshold" herein refers to any number that is used as, e.g., a cutoff to classify a sample feature as particular type of analyte, or a ratio of abnormal to normal cells in the sample. Threshold values can be identified empirically or analytically.

Conventionally, high-quality (in terms of including but not limited to: high resolution, good illumination, low noise-level, low distortion level, good focus, good sharpness, and etc.) microscopy images need to be collected by complicated and very advanced imaging optics which includes high-numeric-aperture and high-magnification compound lens. And we invented a method to reconstruct image(s) with high quality in microscopy imaging using low-cost limited optics with the help of machine learning. In some embodiment, in the training process, we use both high quality images (captured with high quality optics) and low-quality images either captured with limited optics and/or generated by using image processing and/or machine learning from the high-quality images (called virtual images) as training pairs of the same field of view (area) of interest on a sample. Then we use the high-quality and low-quality image pairs to train the machine to let it learn what the low-quality image should be like in a high-quality form. Using the trained model, for a new sample of the same kind of objects, the machine can predict the high-quality form of the image based on the low-quality input.

In some embodiments, the monitoring mark is used in machine learning to achieve a high resolution image using a lower resolution optical system.

Use of "Limited Sample Manipulation"

In the present invention, in some embodiments, the sample position system for imaging the assay have "limited sample manipulation". Some embodiments of limited sample manipulation include, but not limited to:

Description of the Limited Sample Manipulation System:
1. The limited sample manipulation system, comprising: a sample holder; wherein the sample holder has a receptacle for taking in the sample card.
2. The limited sample manipulation system of any prior embodiment, wherein: the accuracy of positioning a sample in the direction along the optical axis is worse than 0.1 um, 1 um, 10 um, 100 um, 1 mm, or in a range between any of the two values.
3. The limited sample manipulation system of any prior embodiment, wherein: the preferred accuracy of positioning a sample in the direction along the optical axis is between 50 um and 200 um.
4. The limited sample manipulation system of any prior embodiment, wherein: the accuracy of positioning a sample in the plane perpendicular to the optical axis is worse than 0.01 um, 0.1 um, 1 um, 10 um, 100 um, 1 mm, or in a range between any of the two values.
5. The limited sample manipulation system of any prior embodiment, wherein: the preferred accuracy of positioning a sample in the plane perpendicular to the optical axis is between 100 um and 1 mm.
6. The limited sample manipulation system of any prior embodiment, wherein, the level error of positioning a sample card is worse than 0.01 degree, 0.1 degree, 0.5 degree, 1 degree, 10 degree, or in a range between any of the two values.
7. The limited sample manipulation system of any prior embodiment, wherein, the preferred level error of positioning a sample card is between 0.5 degree to 10 degree.
8. The limited sample manipulation system of any prior embodiment, wherein, the preferred level error of positioning a sample card is between 0.5 degree to 10 degree.

Sharp Edges of a Monitoring Mark

The term "sharp optical edge" refers to an edge or a boundary of an object in the image take by certain optical system with the following property: at an edge or a boundary of an object in the image, the optical intensity (including but not limit to R, G, B, grey, hue, brightness) changes drastically versus the location. For example, quantitatively, at the boundary, the distance ($X_{90\%}$) in which the normalized intensity decreases from 90% to 10% should be less than 5% of the length of the object in the image by such optical system. In other words, boundary gradient=90%/$X_{90\%}$>1800%/length of object. An example of sharp edge is the edge of a pillar spacer that has a flat top and nearly 90 degree sidewall. An Example of the objects that do not have a sharp edge is spheres.

Examples of TLD and Volume Estimation with Monitor Marks

FIG. 5 shows an embodiment of the sample holding device, QMAX device, and its monitor marks, pillars, used in some embodiments of the present invention. Pillars in QMAX device make the gap between two parallel plates of the sample holding device uniform. The gap is narrow and relevant to the size of the analytes where analytes form a monolayer in the gap. Moreover, the monitor marks in QMAX device are in the special form of pillars, and consequently, they are not submerged by the sample and can be imaged with the sample by the imager in image based assay.

Examples of TLD (True-Lateral-Dimension) Estimation with Monitor Marks

In some embodiments of the present invention for TLD and true volume estimation. the monitor marks (pillars) are used as detectable anchors. However, detecting monitor marks with an accuracy suitable for TLD estimation in image based assay is difficult. This is because these monitor marks are permeated and surrounded by the analytes inside the sample holding device, and they are distorted and blurred in the image due to the distortion from the lens, light diffraction from microscopic objects, defects at microscopic level, mis-alignment in focusing, noise in the image of the sample, etc. And it becomes more difficult if imagers are cameras from commodity devices (e.g. cameras from smart phones), since those cameras are not calibrated by the dedicated hardware once they left the manufacture.

In the present invention, the detection and locating the monitor marks as detectable anchors for TLD estimation is formulated in a machine-learning framework and dedicated machine-learning model is built/trained to detect them in microscopic imaging. Moreover, the distribution of the monitor marks in some embodiments of the present invention is intentionally made to being periodic and distributed in a predefined pattern. This makes the approach in the present invention more robust and reliable.

In particular, an embodiment of the present invention comprises:
(8) load the sample to a sample holding device, e.g. QMAX device, wherein there are monitor marks with known configuration residing in the device that are not submerged in the sample and can be imaged by an imager;
(9) take an image of the sample in the sample holding device including analytes and monitor marks;
(10) build and train a machine learning (ML) model to detect the monitor marks in the image of the sample;
(11) detect and locate the monitor marks in the sample holding device from the image of the sample using the said ML detection model from (3);
(12) generate a mark grid from the detected monitor marks in (4);
(13) calculate a homographic transform based on the generated monitor mark grid;
(14) estimate and save the true-lateral-dimension of the image of the sample from the homographic transform from (6); and
(15) apply the estimated TLD from (7) in subsequent image-based assay to determine area, size, volume and concentration of the analytes.

In some embodiments of the present invention, region based TLD estimation and calibration are employed in image based assay. It comprises:
(13) load the sample to a sample holding device, e.g. QMAX device, wherein there are monitor marks in the device—not submerged in the sample and can be imaged by an imager in the image based assay;
(14) take an image of the sample in the sample holding device including analytes and monitor marks;
(15) build and train a machine learning (ML) model for detecting the monitor marks from the image of the sample taken by the imager;
(16) partition the image of the sample taken by the imager into non-overlapping regions;
(17) detect and locate monitor marks from the image of the sample taken by the imager using the ML model of (3);
(18) generate a region-based mark grid for each of the region with more than 5 non-colinear monitor marks detected in the local region;
(19) generate a mark grid for all regions not in (6) based on detected monitor marks from the image of the sample taken by the imager;
(20) calculate a region-specific homographic transform for each region in (6) based on its own region-based mark grid generated in (6);
(21) calculate a homographic transform for all other regions based on the mark grid generated in (7);
(22) estimate the region based TLD for each region in (6) based on the region based homographic transform generated in (8);
(23) estimate the TLD for other regions based on the homographic transform from (9); and
(24) save and apply the estimated TLDs from (10) and (12) in subsequent image-based assay on partitioned regions.

When the monitor marks are distributed in a pre-defined periodic pattern, such as in QMAX device, they occur and distribute periodically with a certain pitch, and as a result, detection the monitor marks become more robust and reliable in the procedures described above. This is because with periodicity, all monitor marks can be identified and determined from just few detected ones, and detection errors can be corrected and eliminated, should the detected location and configuration do not follow the pre-defined periodic pattern.

Volume Estimation with Monitor Marks

Figure 3:
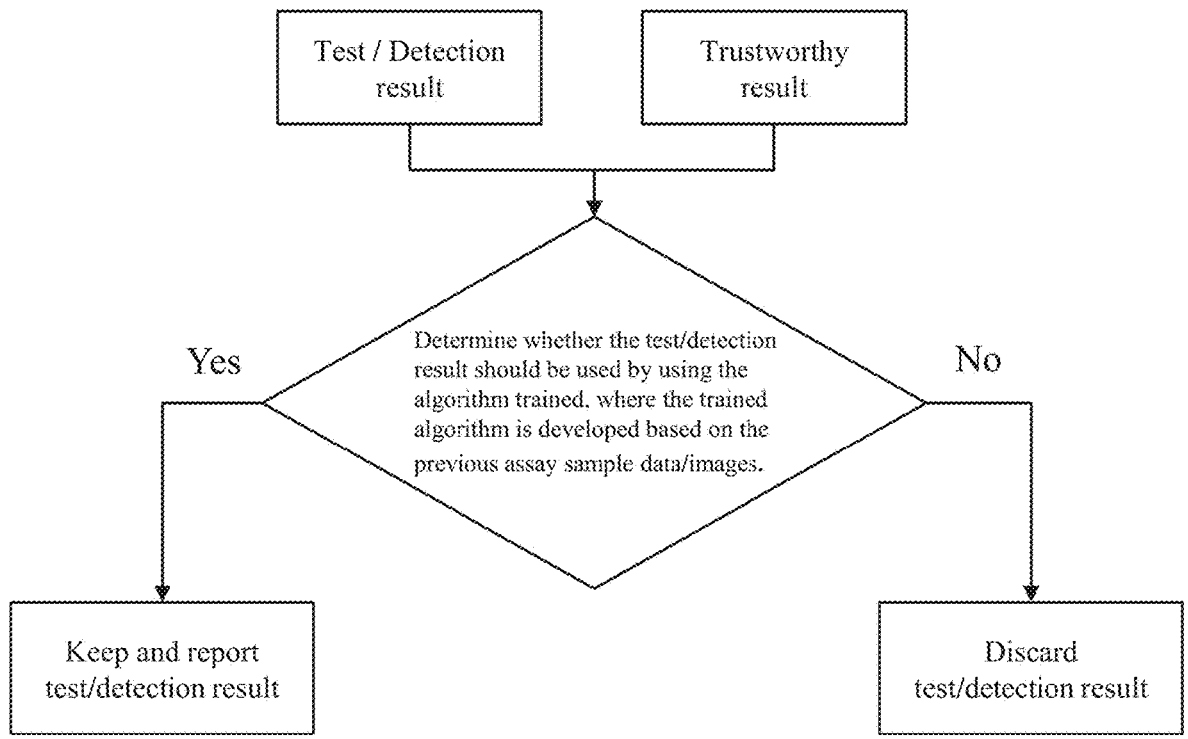
FIG. 3 illustrates a block diagram of embodiment of improving assay accuracy by measuring the trustworthy of the assay device and/or assay operation, wherein a decision is made on reporting or not reporting a detection results.
Figure 4:
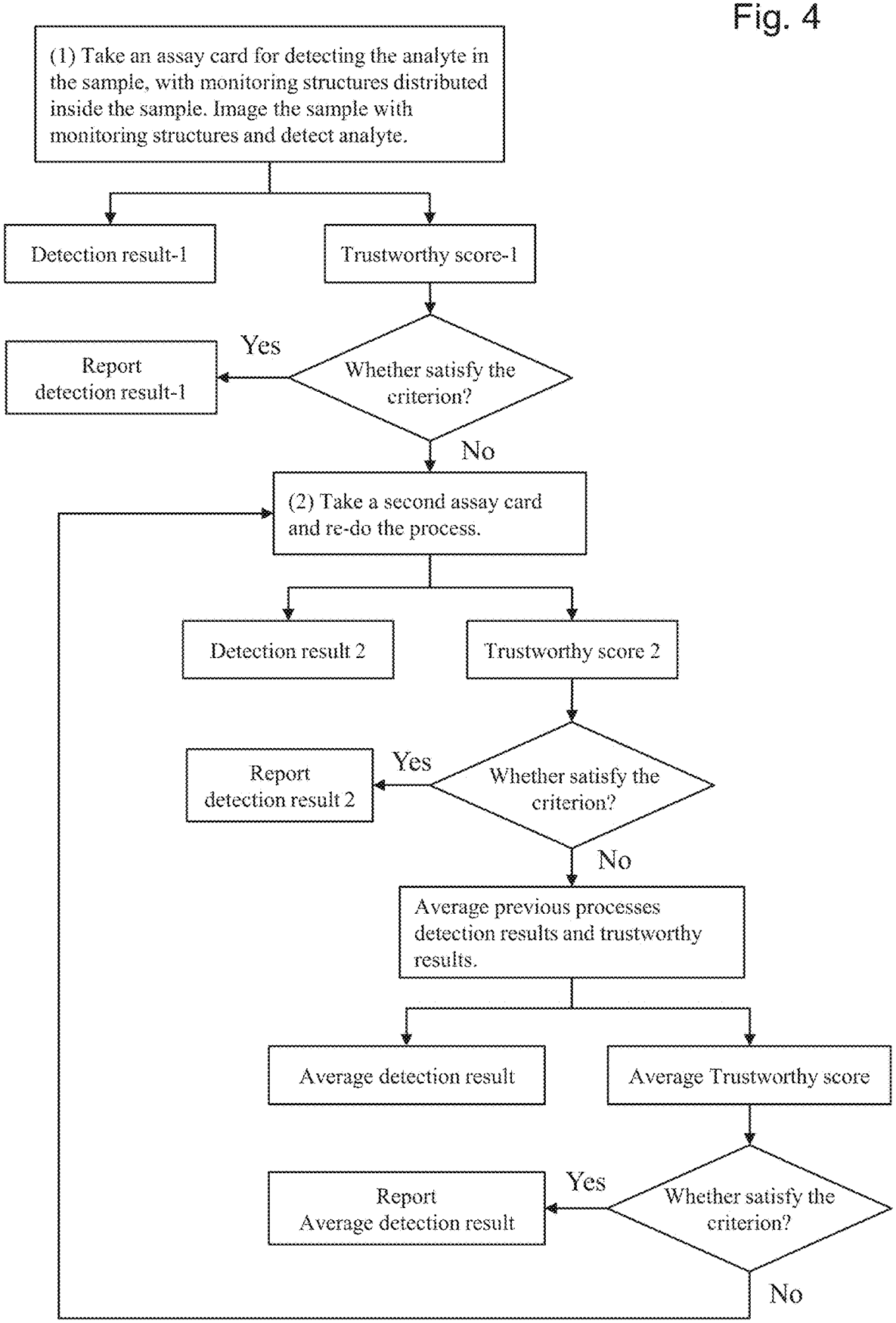
FIG. 4 illustrates a block diagram of embodiment of improving assay accuracy by measuring the trustworthy of the assay device and/or assay operation, by using multiple interactions. In some embodiments, it check the trustworthy of the sample.
Figure 6C:
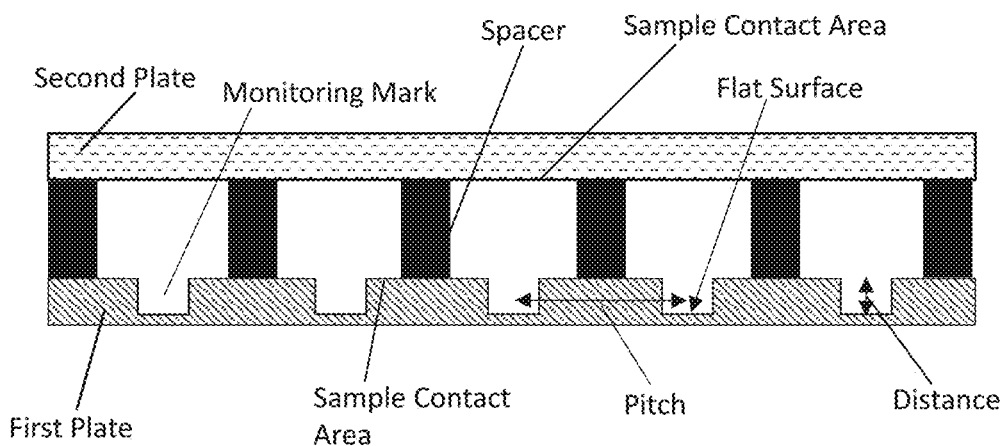
FIG. 6C shows a side view of the device for use in an imaging-based assay.

FIG. 3 is a block diagram of the present invention for volume estimation in image based assay. To estimate the true volume of the sample in the assay, it needs to remove the volume from defects and peripheral objects in the sample, an embodiment of the present invention comprises:
(1) load the sample to a sample holding device with monitor marks, e.g. QMAX device, and take an image of the sample by an imager;
(2) estimate the true-lateral-dimension (TLD) of the image by detecting the monitor marks in the image of the sample as anchors with methods and apparatus described above;
(3) detect and locate the defects, e.g. air bubbles, dusts, monitor marks, etc. in the image of the sample using a machine learning (ML) detection model—built and trained from images of the sample;
(4) determine the covering masks of the said detected defects in the image of the sample using a machine learning (ML) segmentation model—built and trained from images of the sample;
(5) determine a margin distance 4—based on the size of the analytes/objects in the sample and the sample holding device (e.g. 2× max-analyte-diameter);
(6) determine Δ+ masks for all detected defects, i.e. masks with an extra margin extension to their covering masks from (4);
(7) remove the detected defects based on Δ+ masks in (6) in the image of the sample;
(8) save the image from (7) and save the corresponding volume after removal of the volume with the corresponding Δ+ masks of (7) in subsequent image-based assay; and
(9) reject the sample if the area of the removed Δ+ masks or the remaining true volume of the sample exceeds some preset threshold.

In present invention, defects are removed from the image of the sample with an extra margin Δ+ masks. This is important, because defects can impact their surroundings. For example, some defects can alter the height of the gap in the sample holding device, and local volume or concentration distribution around the defects can become different.

The term "monitoring mark", "monitor mark", and "mark" are interchangeable in the description of the present invention.

The term "imager" and "camera" are interchangeable in the description of the present invention.

The term "denoise" refers to a process of removing noise from the received signal. An example is to remove the noise in the image of sample as the image from the imager/camera can pick up noise from various sources, including and not limited to white noise, salt and pepper noise, Gaussian noise, etc. Methods of denoising include and not limited to: linear and non-linear filtering, wavelet transform, statistic methods, deep learning. etc.

The term "image normalization" refers to algorithms, methods and apparatus that change the range of pixel intensity values in the processed image. For example, it includes and not limited to increasing the contrast by histogram stretching, subtract the mean pixel value from each image, etc.

The term "image sharping" refers to the process of enhance the edge contrast and edge content of the image.

The term "image scaling" refers to the process of resizing the image. For example, if an object is too small in the image of the sample, image scaling can be applied to enlarge the image to help the detection. In some embodiments of the present invention, images need to be resized to a specified dimension before input to a deep learning model for training or inference purposes.

The term "alignment" refers to transforming different set of data into one common coordinate system so that they be compared and combined. For example, in image processing, the different set of data are from and not limited to images from multiple imager sensors, and images from the same sensor but at different time, focusing depths, etc.

The term "super resolution" refers to the process of getting a higher resolution image from one or multiple low resolution images.

The term "deblur" refers to the process of removing blurring artifacts from the image, such as removing the blur caused by defocus, shake, motion, etc, in the imaging process.

In some embodiments of the current invention, methods and algorithms are devised to take advantage of the monitor marks in the sample holding device, e.g. QMAX device. This includes and not limited to the estimation and adjustment of the following parameters in the imaging device:
1. shutter speed,
2. ISO,
3. focus (lens position),
4. exposure compensation,
5. white balance: temperature, tint, and
6. zooming (scale factor).

Examples of Image Processing/Analyzing Algorithms Used with Marks

In some embodiments of the present invention, the image processing/analyzing are applied and strengthened with the monitoring marks in the present invention. They include and not limited to the following image processing algorithms and methods:
1. Histogram-based operations include and not limited to:
   a. contrast stretching;
   b. equalization;
   c. minimum filter;
   d. median filter; and
   e. maximum filter.
2. Mathematics-based operations include and not limited to:
   a. binary operations: NOT, OR, AND, XOR, SUB, etc., and
   b. arithmetic-based operations: ADD, SUB, MUL, DIV, LOG, EXP, SQRT, TRIG, INVERT, etc.
3. Convolution-based operations in both spatial and frequency domain, include and not limited to Fourier transform, DCT, Integer transform, wavelet transform, etc.
4. Smoothing operations include and not limited to:
   a. linear filters: uniform filter, triangular filter, gaussian filter, etc., and
   b. non-linear filters: medial filter, kuwahara filter, etc.
5. Derivative-based operations include and not limited to:
   a. first derivatives: gradient filters, basic derivative filters, prewitt gradient filters, sobel gradient filters, alternative gradient filters, gaussian gradient filters, etc.;
   b. second derivatives: basic second derivative filter, frequency domain Laplacian, Gaussian second derivative filter, alternative laplacian filter, second-derivative-in-the-gradient-direction (SDGD) filter, etc., and
   c. other filters with higher derivatives, etc.
6. Morphology-based operations include and not limited to:
   a. dilation and erosion;
   b. boolean convolution;
   c. opening and closing;
   d. hit-and-miss operation;
   e. segmentation and contour;
   f. skeleton;
   g. propagation;
   h. gray-value morphological processing: Gray-level dilation, gray-level erosion, gray-level opening, gray-level closing, etc.; and
   i. morphological smoothing, morphological gradient, morphological Laplacian, etc.

Other Examples of Image Processing/Analyzing Techniques

In some embodiments of the present invention, image processing/analyzing algorithms are used together with and enhanced by the monitoring marks described in this disclosure. They include and not limited to the following:
1. Image enhancement and restoration include and not limited to
   a. sharpen and un-sharpen,
   b. noise suppression, and
   c. distortion suppression.
2. Image segmentation include and not limited to:
   a. thresholding—fixed thresholding, histogram-derived thresholding, Isodata algorithm, background-symmetry algorithm, triangle algorithm, etc.;
   b. edge finding—gradient-based procedure, zero-crossing based procedure, PLUS-based procedure, etc.;
   c. binary mathematical morphology—salt-or-pepper filtering, Isolate objects with holes, filling holes in objects, removing border-touching objects, exo-skeleton, touching objects, etc.; and
   d. gray-value mathematical morphology—top-hat transform, adaptive thresholding, local contrast stretching, etc.
3. Feature extraction and matching include and not limited to:
   a. independent component analysis;
   b. Isomap;
   c. principle component analysis and kernel principal component analysis;
   d. latent semantic analysis;
   e. least squares and partial least squares;
   f. multifactor dimensionality reduction and nonlinear dimensionality reduction;
   g. multilinear principal component analysis;
   h. multilinear subspace learning;
   i. semidefinite embedding; and
   j. autoencoder/decoder.
4. Object detection, classification, and localization
5. Image understanding Example E1. Improvement of Microscopic Imaging Using Monitoring Mark Using monitoring marks in the present invention to improve focus in microscopic imaging:

Marks with sharp edge will provide detectable (visible features) for the focus evaluation algorithm to analyze the focus conditions of certain focus settings especially in low lighting environment and in microscopic imaging. In some embodiments of the present invention, focus evaluation algorithm is at the core part in the auto-focus implementations.

For some diagnostic applications (e.g., colorimetric, absorption-based hemoglobin test, and CBC for samples with very low cell concentrations), detectable features provided by the analyte in the image of the sample is often not enough for the focus evaluation algorithm to run accurately and smoothly. Marks with sharp edges, e.g. the monitor marks in QMAX device, provide additional detectable features for the focus evaluation program to achieve the accuracy and reliability required in the image based assay.

For some diagnostic applications, analytes in the sample are distributed unevenly. Purely relying on features provided by analytes tends to generate some unfair focus setting that gives high weight of focusing on some local high concentration regions and low analyte concentration regions are off target. In some embodiments of the current invention, this effect is controlled with the focusing adjustments from the information of the monitor marks which have strong edges and are distributed evenly with a accurately processed periodic pattern. Using super resolution from single image to generate image with higher resolutions.

Each imager has an imaging resolution limited in part by the number of pixels in its sensor that varies from one million to multimillion pixels. For some microscopic imaging applications, analytes are of small or tiny size in the sample, e.g., the size of platelets in human blood has a dimeter about 1.4 um. The limited resolution in the image sensors put a significant constraint on the capability of the device in the image based assay, in addition to the usable size of FOV, when certain number of pixels is required by the target detection programs.

Single Image Super Resolution (SISR) is a technique to use image processing and/or machine learning techniques to up-sample the original source image to a higher resolution and remove as much blur caused by interpolation as possible, such that the object detection program can run on the newly generated images as well. This will significantly reduce the constraints mentioned above and enable some otherwise impossible applications. Marks with known shape and structure (e.g., the monitor marks in QMAX) can serve as local references to evaluate the SISR algorithm to avoid over-sharpening effect generated with most existing state-of-art algorithms.

In some embodiments o the present invention, image fusion is performed to break the physical SNR (signal-to-noise) limitation in image based assay.

Signal to noise ratio measures the quality of the image of the sample taken by the imager in microscopic imaging. There is a practical limitation for an imaging device due to the cost, technology, fabrication, etc. In some situation, e.g. in mobile healthcare, the application requires higher SNR than the imaging device can provide. In some embodiments of the present invention, multiple images are taken and processed (with same and/or different imaging setting, e.g. an embodiment of a 3D fusion to merge multiple images focused at different focus depth into one super focused image) to generate output image(s) with higher SNR to make such applications possible.

However, images taken by an imager or multiple imagers tend to have some imperfections and defects, caused by physical limitation and implementation constraints. The situation becomes acute in the microscopic imaging of the sample in image based assay, because the analytes in the sample are of tiny size and often without distinct edge features. In some embodiments of the present invention, monitor marks in the image holding device, e.g. the QMAX device, are used for enhanced solutions.

One such embodiment is to handle distortions in the image of the sample taken by the imager. The situation is relatively simple when the distortion parameter is known (most manufacture gives a curve/table for their lens to describe ratio distortion, other distortions can be measured in well-defined experiments). However, when the distortion parameters are unknown (in our cases, it changes with the focus location and even the sample), with the monitoring marks, a new algorithm can iteratively estimate distortion parameters using regularly and even periodically placed monitor marks of the sample holding device (e.g. QMAX device) without requiring a single coordinate references.

In the present invention, in some embodiments, the sample holding device has a flat surface with some special monitor marks for the purpose of analyzing the microfeatures in the image-based assay. Some exemplary embodiments are listed as follows:

A1: True-lateral-dimension (TLD) estimation for the microscopic image of the sample in the image-based assay. True Lateral Dimension (TLD) determines the physical dimension of the imaged analytes in the real would, and it also determines the coordinates of image of the sample in the real world that is related to the concentration estimation in image-based assay. The monitor marks can be used as detectable anchors to determine the TLD and improve the accuracy in the image-based assay. In an embodiment of the present invention, the monitor marks are detected using machine-learning model for the monitor marks, from which the TLD of the image of the sample is derived. Moreover, if the monitor marks have a periodic distribution pattern on the flat surface of the sample holding device, the detection of monitor marks and the per-sample based TLD estimation can become more reliable and robust in image-based assay.

A2: Analyzing the analytes using the measured response from the analyte compound at a specific wavelength of light or at multiple wavelength of light to predict the analyte concentration. Monitor marks that are not submerged in the sample can be used to determine the light absorption of the background corresponding to no analyte compound—to determine the analyte concentration through light absorption, e.g. HgB test in complete-blood-test. In addition, each monitor mark can act as an independent detector for the background absorption to make the concentration estimate robust and reliable.

A3: Focusing in microscopic imagine for image-based assay. Evenly distributed monitor marks can be used to improve the focus accuracy. (a) It can be used to provide minimum amount of vision features for samples with no/less than necessary number of features to do reliable focusing and this can be performed in low light due to the edge contents of the monitor marks. (b) It can be used to provide vision features when features in the sample is unevenly distributed to make the focus decision fairer. (c) It can provide a reference for local illumination conditions that have no/less/different impacts by the content of sample to adjust the weight in focus evaluation algorithms.

A4: Monitor marks can be used as references to detect and/or correct image imperfection caused by but not limited to: unevenly distributed illumination, various types of image distortions, noises, and imperfect image pre-processing operations. (a) For example, positions of the marks can be used to detect and/or correct the ratio distortion when the straight line in 3D world is mapped to the image into a curve. Ratio distribution parameters of the entire image can be estimated based on the position changes of the marks. And the value of ratio distortion parameters can be iteratively estimated by linear testing of horizontal/vertical lines in reproduced images with distortion removal based on assumed ratio distortion parameters.

Examples of Machine Learning (ML) Calculation

B1: One way of using machine learning is to detect the analytes in the image of the sample and calculate the bounding boxes that covering them for their locations, is performed using trained machine-learning models in the inference process of the processing. Another way of using machine learning method to detect and locate analytes in the image of the sample is to build and train a detection and segmentation model which involving the annotation of the analytes in the sample image at pixel level. In this approach, analytes in the image of the sample can be detected and located with a tight binary pixel masks covering them in image-based assay.

B2: When testing hemoglobin in human blood, images are taken at the given narrowband wavelength, and then the average energy pass through the analytes areas and reference areas are analyzed. Based on the known rate of absorption of analytes at the given wavelength and the height of the analyte sample area, the concentration can be estimated. However, this measurement has noises. To cancel out the noise, multiple images can be taken using different wavelength of light, and use machine learning regression to achieve a more accurate and robust estimation. The machine learning based inference takes multiple input images of the sample, taken at different wavelength, and output a single concentration number.

E. Example of Identifying Error Risk to Improve the Measurement Reliability

In some embodiments, a method for improving the reliability of the assay, the method comprising:

(a) imaging the sample on the QMAX card;
(b) analyzing the error risk factor; and
(c) rejecting the card from reporting a measurement result of the card, if the error risk factor is higher than a threshold;

wherein the error risk factor is one of the following factors or any combination thereof. The factors are, but not limited to, (1) edge of blood, (2) air bubble in the blood, (3) too small blood volume or too much blood volume, (4) blood cells under the spacer, (5) aggregated blood cells, (6) lysed blood cells, (7) over exposure image of the sample, (8) under exposure image of the sample, (8) poor focus of the sample, (9) optical system error as wrong lever position, (10) not closed card, (12) wrong card as card without spacer, (12) dust in the card, (14) oil in the card, (14) dirty out of the focus plane one the card, (15) card not in right position inside the reader, (16) empty card, (17) manufacturing error in the card, (18) wrong card for other application, (19) dried blood, (20) expired card, (21) large variation of distribution of blood cells, (22) not blood sample or not target blood sample and others.

In some embodiments, the error risk analyzer is able to detect, distinguish, classify, revise and/or correct following cases in biological and chemical application in device: (1) at the edge of sample, (2) air bubble in the sample, (3) too small sample volume or too much sample volume, (4) sample under the spacer, (5) aggregated sample, (6) lysed sample, (7) over exposure image of the sample, (8) under exposure image of the sample, (8) poor focus of the sample, (9) optical system error as wrong lever, (10) not closed card, (12) wrong card as card without spacer, (12) dust in the card, (14) oil in the card, (14) dirty out of the focus plane one the card, (15) card not in right position inside the reader, (16) empty card, (17) manufacturing error in the card, (18) wrong card for other application, (19) dried sample, (20) expired card, (21) large variation of distribution of blood cells, (22) wrong sample and others.

wherein the threshold is determined from a group test.
wherein the threshold is determined from machine learning.
Wherein the monitoring marks are used as comparison to identify the error risk factor.
Wherein the monitoring marks are used as comparison to assess the threshold of the error risk factor.

Other Embodiments

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

"QMAX" (Q.: quantification; M: magnifying, A. adding reagents, X: acceleration; also termed as self-calibrated compressed open flow (SCOF)) devices, assays, methods, kits, and systems are described in: U.S. Provisional Patent Application No. 62/202,989, which was filed on Aug. 10, 2015, U.S. Provisional Patent Application No. 62/218,455, which was filed on Sep. 14, 2015, U.S. Provisional Patent Application No. 62/293,188, which was filed on Feb. 9, 2016, U.S. Provisional Patent Application No. 62/305,123, which was filed on Mar. 8, 2016, U.S. Provisional Patent Application No. 62/369,181, which was filed on Jul. 31, 2016, U.S. Provisional Patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, all of these disclosures are hereby incorporated by reference for their entirety and for all purposes.

The term "sample" as used herein relates to a material or mixture of materials containing one or more analytes or entity of interest. In some embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled breath condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The term "analyte" refers to a molecule (e.g., a protein, peptides, DNA, RNA, nucleic acid, or other molecule), cells, tissues, viruses, and nanoparticles with different shapes. In some embodiments, an "analyte," as used herein is any substance that is suitable for testing in the present method.

As used herein, a "diagnostic sample" refers to any biological sample that is a bodily byproduct, such as bodily fluids, that has been derived from a subject. The diagnostic sample may be obtained directly from the subject in the form of liquid, or may be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present method.

As used herein, a "foodstuff sample" refers to any sample that is suitable for animal consumption, e.g., human consumption. A foodstuff sample may include raw ingredients, cooked food, plant and animal sources of food, preprocessed food as well as partially or fully processed food, etc. Typically, samples that are not in liquid form are converted to liquid form before analyzing the sample with the present method.

The term "diagnostic," as used herein, refers to the use of a method or an analyte for identifying, predicting the outcome of and/or predicting treatment response of a disease or condition of interest. A diagnosis may include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition may not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc.

ADDITIONAL NOTES

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A method for improving accuracy of an assay in detecting,
   using an assay device, an analyte in or suspected of being in a sample, wherein the assay device or an operation of the assay device has one or more parameters each having a random variation, the method comprising:
   (a) detecting, using the assay device, the analyte, comprising:
      (i) placing the sample into the assay device; and
      (ii) measuring, using the assay device, the analyte in the sample, to generate a detection result; and
   (b) determining trustworthiness of the detection result in step (a), comprising:
      (i) imaging, using an imager, one or more images of at least a part of the sample and/or at least part of the assay device, wherein the images substantially represent the conditions under which the at least a part of the sample is measured in generating the detection result in step (a); and
      (ii) determining a trustworthiness of the detection result in step (a) by using an algorithm to analyze the images and one or more parameters, to generate a trustworthy score.

2. The method of claim 1, wherein the measuring in step (a) comprises an analysis of the one or more images of at least a part of the sample and/or at least part of the assay device, imaged in step (b).

3. The method of claim 1, wherein
   a) the assay device comprises a sample holder that has a sample contact area for contacting the sample
   (b) the sample is placed on the sample contact area;
   (c) the at least one sample contact area comprises one or more monitoring structures;
   (d) the imaging images at least a part of the sample and at least a part of the monitoring structures for trustworthiness determination; and
   (e) the monitoring structures comprises a structure of an optical property that is used to monitor the operation and/or assay device quality of the assay.

4. The method of claim 3, wherein some of the monitoring structures are periodically arranged.

5. The method of claim 3, wherein the assay device comprises a sample holder and the method comprises
   a) taking an image of the sample in the sample holder on the area-of-interest (AoI) for assaying with an imager;
   b) performing machine learning based inference with a trained machine learning model to detect and segment the monitor structures with analytes on top to determine the (area-analytes-on-pillars-in-AoI associated with the detected monitor structures based on their segmentation contour masks in the AoI;

c) determining the area ratio between the area-analytes-on-pillars-in-AoI and the area-of-AoI: ratio-analytes-on-pillars-area-in-AoI=area-analytes-on-pillars-in-AoI/area-of-AoI; and d) reporting if the ratio-analytes-on-pillars-area-in-AoI from (c) exceeds a certain threshold an error or defect and the detection result is not trustworthy, wherein the said threshold is derived from the training/evaluation data or from the physical rules that govern the distribution of the analytes.

6. The method of claim 5, wherein the threshold value of the ratio-analytes-on-pillars-area-in-AoI is 10%, 15%, 30%, 50%, or a value between any two.

7. The method of claim 5, wherein the detection and segmentation from the image of the sample taken by the imager in the image-based assay are based on image processing, machine learning or a combination of image processing and machine learning.

8. The method of claim 1, further comprising, when the trustworthy score is untrustworthy, a step of discarding the detection result and having a second assay device to repeat the steps of (a) and (b).

9. The method of claim 1, wherein the algorithm is machine learning.

10. The method of claim 1, wherein the sample comprises at least one of parameters that has a random variation.

11. The method of claim 1, wherein the sample comprises at least one of parameters that has a random variation, wherein the parameter comprises having dusts, air bubble, non-sample materials, or any combination of thereof.

12. The method of claim 1, further comprising a step of keeping or rejecting the detection result using the trustworthy score.

13. The method of claim 1, wherein the assay is a device that uses a chemical reaction to detect the analyte.

14. The method of claim 1, wherein the assay is an immunoassay, nucleic acid assay, colorimetric assay, luminescence assay, or any combination of thereof.

15. The method of claim 1, wherein the assay device comprises a sample holder comprising two plates facing each other with a gap of 250 um or less, wherein at least a part of the sample is inside of the gap.

16. The method of claim 15, wherein the assay device comprises a sample holder comprising two plates movable to each other and spacers that regulate the spacing between the plates, and wherein at least a part of the sample is inside of the gap.

17. The method of claim 16, wherein:
(i) the device further comprises a monitoring structure;
(ii) the device further comprises a monitoring structure, wherein the monitoring structure is used as a parameter together with an imaging processing method in an algorithm that (i) adjusting the imaging, (ii) processing an image of the sample, (iii) determining a property related to the micro-feature, or (iv) any combination of the above;
(iii) the device further comprises a monitoring structure, wherein the monitoring structure is used as a parameter together with step (b);
(iv) the device further comprises a monitoring structure, wherein the spacers are the monitoring structure, wherein the spacers have a substantially uniform height that is equal to or less than 200 microns, and a fixed inter-spacer-di stance (ISD); or
(v) the device further comprises a monitoring structure, wherein the monitoring structure is used for estimating the TLD (true-lateral-dimension) and true volume estimation.

18. The method of claim 1, wherein the sample is selected from cells, tissues, bodily fluids, and stool.

19. The method of claim 1, wherein the sample is amniotic fluid, aqueous humour, vitreous humour, blood, breast milk, cerebrospinal fluid (CSF), cerumen, chyle, chime, endolymph, perilymph, feces, gastric acid, gastric juice, lymph, mucus, pericardial fluid, peritoneal fluid, pleural fluid, pus, rheum, saliva, sebum, semen, sputum, sweat, synovial fluid, tears, vomit, urine, or exhaled breath condensate, and wherein the blood comprises whole blood, fractionated blood, plasma and serum.

20. The method of claim 1, wherein the analyte comprising a molecule, a cell, a tissue, a virus, and a nanoparticle, and wherein the molecule comprises protein, peptides, DNA, RNA, and nucleic acid.

21. The method of claim 1, wherein the sample is non-flowable but deformable.

22. The method of claim 1, wherein the method further comprises a step of discarding the detection result generated in step (a), if the worthiness determined in the step (b) is below a threshold.

23. The method of claim 1, wherein the algorithm is machine learning, artificial intelligence, statistical methods, or a combination of thereof.

24. The method of claim 1, wherein the assay device comprises a sample holder comprising a first plate, a second plate, and spacers, wherein the first and second plates are movable to each other into different configurations, including an open configuration and a closed configuration,
wherein the open configuration is a configuration, in which the two plates are partially or completely separated apart, the spacing between the plates is not regulated by the spacers, and the sample is deposited on one or both of the plates, and
wherein the closed configuration, which is configured after the sample is deposited in the open configuration, is the configuration, in which, at least part of the sample is compressed by the first and second plates into a layer of uniform thickness and is substantially stagnant relative to the plates, wherein the uniform thickness of the layer confined by the sample contact areas of the two plates and is regulated by the two plates and the spacers.

25. The method of claim 1, wherein in step (b)(i)-(b)(ii), the algorithm uses machine learning with a training set to determine if a result is trustworthy, wherein the training set uses an operational variable with an analyte in the sample.

26. The method of claim 1, wherein in step (b)(i)-(b)(ii), the algorithm uses a lookup table to determine if a result is trustworthy, wherein the lookup table contains an operational variable with an analyte in the sample.

27. The method of claim 1, wherein in step (b)(i)-(b)(ii), the algorithm uses a neural network to determine if a result trustworthy, wherein the neural network is trained using an operational variable with an analyte in the sample.

28. The method of claim 1, wherein in step of (b)(i)-(b)(ii) the algorithm uses machine learning, lookup table or neural work to determine if a result is trustworthy, wherein the machine learning, lookup table or neural work contains operational variables including a condition of air bubble and/or dust in the image of the portion of the sample.

29. The method of claim 1, wherein in step of (b)(i)-(b)(ii), the algorithm uses machine learning, that determines if a result is trustworthy, use machine learning, lookup table or neural network to determine operational variables of air bubble and/or dust in the image of the portion of the sample.

30. The method of claim 1, wherein step (b) further comprises an image segmentation for image-based assay.

31. The method of claim 1, wherein step (b) further comprises a focus checking in image-based assay.

32. The method of claim 1, wherein step (b) further comprises an Evenness of analyte distribution in the sample.

33. The method of claim 1, wherein step (b) further comprises an analyze and detection for aggregated analytes in the sample.

34. The method of claim 1, wherein step (b) further comprises an analyze for Dry-texture in the image of the sample in the sample.

35. The method of claim 1, wherein step (b) further comprises an analyze for Defects in the sample.

36. The method of claim 1, wherein step (b) further comprises a correction of camera parameters and conditions as distortion removal, temperature correction, brightness correction, contrast correction.

37. The method of claim 1, wherein step (b) further comprises methods and operations with Histogram-based operations, Mathematics-based operations, Convolution-based operations, Smoothing operations, Derivative-based operations, Morphology-based operations.

38. The method of claim 1, wherein the assay device comprises a sample holder, and the method comprises:
   a) taking an image of the sample in the sample holder on the area-of-interest (AoI) for assaying with an imager;
   b) segmenting the image of the sample taken by the said imager from (b) into equal-sized and non-overlapping sub-image patches;
   c) performing machine learning based inference with a trained machine learning model for analyte detection and segmentation on each image patch—to determine and not limited to the analyte count and concentration thereof;
   d) sorting the analyte concentration of the constructed sub-image patches in ascending order and determine the 25% quantile Q1 and 75% quantile Q3 thereof;
   e) determining the uniformity of the analytes in the image of the sample with an inter-quantile-range based confidence measure: confidence-IQR=(Q3−Q1)/(Q3+Q1), and
   f) reporting, if the confidence-IQR exceeds a certain threshold, an error or defect and the detection result is not trustworthy, wherein the said threshold is derived from training/evaluation data or from physical rules that govern the distribution of the analyte.

39. The method of claim 38, further comprising detecting and characterizing outliers in the image-based assay based on the non-overlapping sub-image patches of the input image of the sample, and the detecting of the outliers is based on non-parametric methods, parametric methods and a combination of both in the assaying process.

40. The method of claim 1, wherein the assay device comprises a sample holder and the method comprises:
   a) taking an image of the sample in the sample holder on the area-of-interest (AoI) for assaying with an imager;
   b) performing machine learning based inference with a trained machine learning model for dry texture detection and segmentation to detect dry texture areas and determine area-dry-texture-in-AoI associated with segmentation contour masks that cover those-areas of dry-texture in the AoI of the image of the sample;
   c) determining the area ratio between the area-dry-texture-in-AoI and the area-of-AoI: ratio-dry-texture-area-in-AoI; and
   d) reporting, if the ratio-dry-texture-area-in-AoI from (c) exceeds a threshold value, an error or defect and the detection result is not trustworthy, wherein the threshold is derived from training/evaluation data or from physical rules that govern the distribution of the analyte.

41. The method of claim 40, wherein the threshold value of the ratio-dry-texture-area-in-AoI is 10%, 15%, 30%, 50%, or a value between any two.

42. The method of claim 41, wherein a threshold value of an airbubble-gap-area-in-AoI is 10%, 15%, 30%, 50%, or a value between any two.

43. The method of claim 40, further comprising monitoring structures built in with the sample holder; and the said monitor structures are applied as detectable anchors to make the estimation of the true-lateral-dimension or Field-of-View (FoV) estimation accurate in face of the distortions in microscopic imaging.

44. The method of claim 40, wherein the monitoring structures of the sample holder have some configurations with a prescribed periodic distribution in the sample holding device to make detection and location of the monitor marks as anchors in true-lateral-dimension (TLD) or Field-of-View (FoV) estimation reliable and robust.

45. The method of claim 1, wherein the algorithm comprises a machine learning model, wherein training data is used to train the machine learning model; wherein the training comprises (i) tuning the hyper-parameters and model structure with the training and evaluation data until the model reaches a satisfactory performance on the evaluation and test data; and (ii) performing the inference on the test data using the trained machine learning model.

46. The method of claim 1, wherein in step of (b)(i)-(b)(ii), the algorithm uses a threshold for operational variable to determine if a result is trustworthy.

* * * * *